(12) United States Patent
Masuda et al.

(10) Patent No.: US 8,391,581 B2
(45) Date of Patent: *Mar. 5, 2013

(54) X-RAY INSPECTING APPARATUS AND X-RAY INSPECTING METHOD

(75) Inventors: Masayuki Masuda, Nishinomiya (JP); Noriyuki Kato, Kyotanabe (JP); Shinji Sugita, Nara (JP); Tsuyoshi Matsunami, Kyotanabe (JP); Yasushi Sasaki, Nishinomiya (JP)

(73) Assignee: Omron Corporation, Kyoto (JP)

( * ) Notice: Subject to any disclaimer, the term of this patent is extended or adjusted under 35 U.S.C. 154(b) by 416 days.

This patent is subject to a terminal disclaimer.

(21) Appl. No.: 12/810,773

(22) PCT Filed: Dec. 25, 2008

(86) PCT No.: PCT/JP2008/073587

§ 371 (c)(1),
(2), (4) Date: Jun. 25, 2010

(87) PCT Pub. No.: WO2009/084581

PCT Pub. Date: Jul. 9, 2009

(65) Prior Publication Data

US 2010/0329532 A1    Dec. 30, 2010

(30) Foreign Application Priority Data

Dec. 27, 2007 (JP) ................................. 2007-337572
Mar. 14, 2008 (JP) ................................. 2008-065187

(51) Int. Cl.
*G06K 9/00* (2006.01)
*G01B 15/06* (2006.01)

(52) U.S. Cl. ......................................... 382/132; 378/58

(58) Field of Classification Search .................. None
See application file for complete search history.

(56) References Cited

U.S. PATENT DOCUMENTS 5,757,878 A * 5/1998 Dobbs et al. ...................... 378/19
5,841,831 A * 11/1998 Hell et al. .......................... 378/19

(Continued)

FOREIGN PATENT DOCUMENTS

JP    56-138268    10/1981
JP    5-86218      12/1993

(Continued)

OTHER PUBLICATIONS

Office Action issued in Japanese Application No. 2010-057524 dated Sep. 11, 2012.

(Continued)

*Primary Examiner* — Mussa A Shaawat
(74) *Attorney, Agent, or Firm* — Foley & Lardner LLP

(57) ABSTRACT

An X-ray inspecting apparatus capable of high-speed inspection of a prescribed inspection area of an object of inspection is provided. The X-ray inspecting apparatus includes: a scanning X-ray source for outputting X-ray; an X-ray detector driving unit on which a plurality of X-ray detectors are mounted, and capable of driving the plurality of X-ray detectors independently; and an image acquisition control mechanism controlling acquisition of image data by X-ray detector driving unit and X-ray detectors. A scanning X-ray source emits X-ray while moving the X-ray focal point of the X-ray source to each of X-ray emission originating positions set for each X-ray detector such that the X-ray passes through a prescribed inspection area of an object of inspection and enters each X-ray detector. Image pick-up by some of the X-ray detectors and movement of other X-ray detectors to an image pick-up position are executed in parallel and alternately. An image acquisition control unit acquires the image data picked-up by X-ray detectors, and a computing unit reconstructs an image in the inspection area based on the image data.

15 Claims, 62 Drawing Sheets

U.S. PATENT DOCUMENTS

| | | | |
|---|---|---|---|
| 6,480,564 B1 * | 11/2002 | Kim et al. | 378/21 |
| 6,628,745 B1 * | 9/2003 | Annis et al. | 378/21 |
| 6,920,196 B2 * | 7/2005 | Ueno et al. | 378/19 |
| 6,973,159 B2 * | 12/2005 | Amemiya et al. | 378/19 |
| 7,053,376 B2 * | 5/2006 | Amemiya et al. | 250/363.04 |
| 7,127,026 B2 * | 10/2006 | Amemiya et al. | 378/19 |
| 7,355,181 B2 * | 4/2008 | Amemiya et al. | 250/363.04 |
| 7,759,646 B2 * | 7/2010 | Amemiya et al. | 250/363.04 |
| 2003/0012331 A1 * | 1/2003 | Kojima et al. | 378/4 |
| 2003/0058983 A1 * | 3/2003 | Thayer | 378/19 |
| 2003/0076920 A1 | 4/2003 | Shinno et al. | |
| 2003/0109779 A1 | 6/2003 | Ohishi et al. | |
| 2003/0118155 A1 * | 6/2003 | Ueno et al. | 378/177 |
| 2003/0179853 A1 * | 9/2003 | Amemiya et al. | 378/63 |
| 2004/0081277 A1 * | 4/2004 | Amemiya et al. | 378/63 |
| 2004/0081278 A1 * | 4/2004 | Amemiya et al. | 378/63 |
| 2005/0157841 A1 * | 7/2005 | Chopra | 378/22 |
| 2006/0045234 A1 | 3/2006 | Pelc et al. | |
| 2006/0126781 A1 | 6/2006 | Hartung et al. | |
| 2006/0188059 A1 * | 8/2006 | Amemiya et al. | 378/19 |
| 2007/0025497 A1 * | 2/2007 | Fujita | 378/9 |
| 2008/0152074 A1 * | 6/2008 | Amemiya et al. | 378/12 |
| 2008/0267347 A1 * | 10/2008 | Shimono | 378/19 |

FOREIGN PATENT DOCUMENTS

| | | |
|---|---|---|
| JP | 08-055887 A | 2/1996 |
| JP | 11-133200 A | 5/1999 |
| JP | 11-326242 A | 11/1999 |
| JP | 2000-46760 | 2/2000 |
| JP | 2000-217035 A | 8/2000 |
| JP | 2001-273860 | 10/2001 |
| JP | 2002-071587 A | 3/2002 |
| JP | 2003-061946 | 3/2003 |
| JP | 2003-344316 | 12/2003 |
| JP | 2005-347174 | 12/2005 |
| JP | 2006-061692 | 3/2006 |
| JP | 2006-116310 | 5/2006 |
| JP | 2006-162335 | 6/2006 |
| JP | 2007-007217 | 1/2007 |
| JP | 3940579 | 4/2007 |
| WO | WO2007-002927 A2 | 1/2007 |

OTHER PUBLICATIONS

Feldkamp, L.A., et al.; Practical Cone-Beam Algorithm; Journal of the Optical Society of America, pp. 612-619; A/vol. 1, No. 6/Jun. 1984.

Andersen, A.H., et al., Simultaneous Algebraic Reconstruction Technique (SART): A Superior Implementation of the Art Algorithm; pp. 81-94; Ultrasonic Imaging 6 (1984).

Japan Patent Office; Decision to Grant Patent on application 2010-057525 mailed Sep. 18, 2012; pp. 1-2.

* cited by examiner

X-RAY INSPECTING APPARATUS AND X-RAY INSPECTING METHOD

TECHNICAL FIELD

The present invention relates to X-ray inspecting apparatus and X-ray inspecting method. More specifically, the present invention relates to a method for image pick-up for inspecting an object using X-ray, involving a technique applicable to X-ray inspecting method and X-ray inspecting apparatus.

BACKGROUND ART

Recently, thanks to micro-fabrication technique of sub-microns, LSI (Large-Scale Integration) of higher degree of integration has been developed and, as a result, it becomes possible to pack functions that have been conventionally implemented in a plurality of separate packages in one LSI. Conventional QFP (Quad Flat Package) and PGA (Pin Grid Array) can no longer accommodate the increased number of pins resulting from incorporating necessary functions in one package and, therefore, LSIs of BGA (Ball Grid Array) or CSP (Chip Size Package) in particular come to be used these days. Further, for applications requiring micro-miniaturization such as portable telephones, BGA package is used even if the number of pins is not so large.

Though BGA and CSP packages of LSI much contribute to micro-miniaturization, after assembly, soldered portions and the like are not visible from the appearance. Therefore, when printed boards and the like mounting BGA and CSP packages are to be inspected, the object of inspection is irradiated with X-ray, and the acquired fluoroscopic image is analyzed, for determining whether the quality is acceptable or not.

By way of example, Patent Document 1 discloses an X-ray tomographic surface inspection apparatus that can acquire a sharp X-ray image by using an X-ray plane sensor.

Patent Document 2 discloses a method for reconstructing an image in inclined-three-dimensional X-ray CT (Computed Tomography) by arbitrarily selecting an angle of X-ray irradiation.

Patent Document 3 discloses an X-ray inspection device in which two-dimensional inspection is performed based on X-ray images acquired by a parallel X-ray detection device, and three-dimensional inspection is performed based on X-ray images acquired by inclined X-ray detecting means, so that both inspections can be done at high speed. A technique of reconstructing a three-dimensional image of an object of inspection based on a plurality of X-ray images is also mentioned in this reference. As a method for reconstruction, "filtered back-projection method" is suggested.

Further, Patent Document 4 discloses a mechanism that can be driven by a single motor to move an X-ray source on linear orbit, circular orbit and spiral orbit for taking laminography in an X-ray tomographic apparatus. Here, the X-ray source is moved, and since the X-ray source is heavy and only one motor is used for driving, high-speed movement is difficult. Further, in order to realize three different moving modes of rotational, linear and spiral movements by one imaging system, the mechanism is complicated. Since various improvements of the mechanism are required to increase the speed of movement, it is difficult to increase the operation speed of the mechanism.

In a general industrial X-ray fluoroscope, if the object of inspection is of minute size, it is desirable to acquire an X-ray fluoroscopic image enlarged as much as possible. For this purpose, the size of focal point as the area of X-ray generation must be extremely small. Thus, a micro-focus X-ray source, which is a transmission type X-ray source having the focal point dimension of a few μm, is used. If an electron beam current (X-ray source current) for generating the X-ray is increased in such a micro-focus X-ray source in order to improve image quality of the fluoroscope, heat builds up at a portion of the target where the electrons impinge (focal point) and the target melts locally. Therefore, it is a common practice to set an allowable limit value (permissible load). Patent Document 5 discloses a micro-focus X-ray source including an anode (target) consisting of a rotating disk, enabling increase of the permissible load.

Patent Document 6 discloses a pulse X-ray source capable of generating pulsed X-rays by intermittently defocusing the electron beam using a deflecting electromagnetic coil, to make longer the life of X-ray source.

[Method for Image Reconstruction of X-Ray CT]

As described above, in X-ray CT, based on the measured values of X-ray after transmission through the object and detected by the X-ray detector, at least a cross-sectional image of the object is reconstructed. Since three-dimensional distribution of X-ray absorption factor of the object or at least a part of the object can be obtained, it is eventually possible to reconstruct an arbitrary cross-sectional image of the object or a part of the object, that is, an image of a plane that crosses the light receiving surface of the X-ray detector. As the method for reconstruction, "analytical method" and "iterative method" have been known. In the following, these methods for image reconstruction will be briefly discussed.

(Description of X-Ray Projection Data)

FIG. 57 is an illustration related to the methods for image reconstruction. The X-ray image reconstruction refers to a method for calculating distribution of X-ray absorption coefficient in an object of inspection, by measuring, from a plurality of different angles, how much X-ray irradiating the object from outside is absorbed (attenuated) by the object of inspection.

In the following, description will be given assuming that measurement is done using a so-called scanning X-ray source.

Referring to FIG. 57, X-ray emitted from an X-ray focal point Fa corresponding to an X-ray detector Da passes through an object of inspection (not shown) and reaches a pixel Pa of X-ray detector Da. As the X-ray is transmitted through the object of inspection, the amount of X-ray (X-ray intensity) attenuates by the amount corresponding to X-ray absorption coefficient of each of the components and the like forming the object of inspection. The amount of attenuation in X-ray intensity is recorded as a pixel value of detector pixel Pa.

When we represent the X-ray intensity emitted from X-ray focal point Fa by I, the path of X-ray from X-ray focal point Fa to detector pixel Pa by t and the distribution of X-ray absorption coefficients of the object of inspection by f(x, y, z), the intensity Ia of X-ray that reached the detector pixel Pa is given by the following equation (1).

$$Ia = I \times \exp\{-\int f(x,y,z)dt\} \quad (1)$$

Taking the logarithm of both sides of the equation above, distribution of X-ray absorption coefficients along the path t is given as a linear integral value of Equation (2) below. A value obtained by measuring the X-ray absorption coefficients distribution by the X-ray detector is referred to as projection data. Specifically, the X-ray detector detects a distribution of X-ray attenuation (or X-ray intensity distribution).

$$\int f(x,y,z)dt = \ln(I/Ia) \quad (2)$$

(Description of Analytical Method (for Example, FBP Method: Filtered Back-Projection Approach))

As shown in FIG. 57, when the analytical method is used, for one object of inspection (or one part of the object of inspection), projection data of X-ray intensity Ib of the X-ray emitted from a focal point Fb and reached an X-ray detector Db, which is arranged at a position different from the arrangement of X-ray detector Da, is detected. In actual practice, the projection data as such is detected for a plurality of arrangements with respect to one object of inspection (or one part of the object of inspection), and a cross-sectional image of the object of inspection is reconstructed from the projection data.

FIG. 58 shows the arrangements of a field of view FOV and a reconstruction pixel V as the object of reconstruction operation in the field of view FOV of the object of inspection, X-ray focal points Fa and Fb, and X-ray detectors Da and Db shown in FIG. 57, viewed from above. When the X-ray that has been transmitted through a portion of reconstruction pixel V forms images on X-ray detectors Da and Db, the images are enlarged in proportion to the ratio of (distance from focal point to reconstruction pixel V) to (distance from focal point to X-ray detector).

Feldkamp et al. propose a reconstruction algorithm for three-dimensional image reconstruction based on Equation (2). The algorithm (a so-called Feldkamp method) is well known as disclosed in Non-Patent Document 1 and, therefore, detailed description will not be given here. In the following, Filtered Back-Projection method as a general method will be briefly described.

An operation of obtaining the distribution f(x, y, z) of X-ray absorption coefficients from the projection data, by adding projection data along the path t followed by the X-ray is referred to as back-projection. If the projection data are simply added, blurring occurs because of peaked point spread function of imaging system and, therefore, the projection data are filtered. Here, a high-frequency emphasizing filter, such as Shepp-Logan filter, is used for the filtering. The desirable direction of filtering is considered to be vertical to the direction of X-ray transmission path. In Feldkamp method, filtering is done approximating that projection data transmission paths are all in the same direction, and an image allowing inspection can be reconstructed.

In the following, steps of image reconstruction in accordance with the present embodiment will be described. First, a value pa' obtained by filtering the projection data pa of detector pixel. Pa at X-ray detector Da is added to a pixel value v of reconstruction pixel V. Further, a value pb' obtained by filtering the projection data pb of detector pixel Pb at X-ray detector Db is added to the pixel value v of reconstruction pixel V. Then, we obtain v=pa'+pb'. When such a back-projection operation is conducted on all or some of the X-ray detectors, the pixel value v of eventually resulting reconstruction pixel V will be represented by Equation (3) below:

$$v = \Sigma(pa' + pb' + \ldots) \quad (3)$$

By performing this operation for all the reconstruction pixels V in the reconstruction area (field of view) FOV, the distribution of X-ray absorption coefficients of the object of inspection is obtained, and hence, a reconstructed image data is obtained.

FIG. 59 is a flowchart representing the process steps of the Filtered Back-Projection method.

Referring to FIG. 59, when the process in the analytical method starts (S5002), first, projection data to be the object of processing are selected from projection data of a plurality of picked-up images (S5004). Next, the selected projection data are filtered (S5006).

Further, not-yet processed reconstruction pixel V in reconstruction field of view FOV is selected (S5008), and a detector pixel for the reconstruction pixel V is found (S5010).

Thereafter, the filtered pixel value is added to reconstruction pixel V (S5012), and whether or not addition has been done on all reconstruction pixels is determined (S5014). If the process is not yet done on all reconstruction pixels, the process returns to step S5008, and if the process has been completed, the process proceeds to step S5016.

At step S5016, whether or not the process has been done on all projection data is determined. If the process is not yet done on all projection data, the process returns to step S5004. If the process has been done on all projection data, generation of a reconstructed image ends (S5018).

(Description of Iterative Method (SART))

In the iterative method, the distribution f(x, y, z) of X-ray absorption coefficients and the projection data In (I/Ia) of the object of inspection are regarded as equations for reconstruction.

FIG. 60 is a schematic illustration showing the concept of the process in accordance with the iterative method, when a scanning X-ray source is used. FIG. 61 corresponds to the illustration of FIG. 60, viewed from above.

Referring to FIGS. 60 and 61, the steps of reconstruction in accordance with the iterative method will be described. A vector v (with an overhead arrow→representing a vector; in the text of specification, represented by "v") obtained by arranging a series of pixel values of the reconstructed image and a vector p (with an overhead arrow→representing a vector; in the text of specification, represented by "p") obtained by arranging a series of projection data are represented by Equations (4) and (5) below.

In the following, a pixel of an image calculated to be formed on X-ray detector Da by the X-ray emitted from X-ray focal point Fa assuming that the reconstruction pixel V has a certain value is referred to as an intermediate projection pixel Qa, while the pixel actually observed on X-ray detector Da is referred to as detector pixel Pa. Similarly, corresponding pixels of X-ray detector Db will be referred to as intermediate projection pixel Qb and detector pixel Pb.

In the iterative method, for the assumed reconstruction pixel vector v and the corresponding intermediate projection data vector q, iterative operation of updating the assumed vector v is continued until the intermediate projection data vector q can be regarded as matching the projection data of actually measured detector pixel value Pa or Pb, and thereby, the solution v is obtained.

$$\vec{v} = (v_1, v_2, \ldots, v_J)^T \quad (4)$$

$$\vec{p} = (p_1, p_2, \ldots, p_I)^T \quad (5)$$

Here, J represents the number of pixels in the reconstruction area (field of view), and I represents the number of pixels of the projection data. Further, T represents transposition. A projection operation establishing a relation between v and p is given by the I×J coefficient matrix of (6).

$$W = \{w_{ij}\} \quad (6)$$

Here, the image reconstruction in accordance with the iterative method can be formulated as a problem of solving the linear equation (7) below to find the solution v.

$$W\vec{v} = \vec{p} \quad (7)$$

Specifically, the contribution of vj to pj is wij. It is noted that W represents how much the pixel value v of the reconstructed image contributes to the pixel value p of projection data. It can be calculated from geometric positions of the X-ray focal point and the X-ray detector, and this value is sometimes referred to as a detection probability or weight.

As the iterative method, a method for algebraically solving the equation or a method considering statistical noise have been proposed. In the following, a commonly used algebraic method for SART (Simultaneous Algebraic Reconstruction Technique) will be described. Details are described in Non-Patent Document 2.

In SART, first, an initial reconstructed image $v^0$ (with an overhead arrow→representing a vector; in the text of specification, represented by "$v^0$") given by the following expression is assumed.

$$\vec{v}^0 \qquad (8)$$

The initial reconstructed image $v^0$ may be data of all 0, or it may assume data obtained from CAD (Computer Aided Design) data.

Next, an intermediate projection data $q^0$ (with an overhead arrow→representing a vector; in the text of specification, represented by "$q^0$") given by the following equation (9) is generated, using projection operation W.

$$\vec{q}^0 = W\vec{v}^0 \qquad (9)$$

The intermediate projection data $q^0$ may be generated for one projection data, or it may be generated for a plurality of projection data. In the following, description will be given assuming that the generation is performed for one projection data.

The generated intermediate projection data $q^0$ is compared with projection data p obtained from the X-ray detector. As the method for comparison, a method for calculating difference and a method for performing a division are known. In SART, the difference $(p-q^0)$ is calculated.

The initial reconstructed image $v^0$ is updated. The equation used for updating (iteration equation) is as represented by (10) below.

$$v_j^1 = v_j^0 + \frac{\sum_{i=1}^{I} \frac{p_i - q_i}{\sum_{j=1}^{J} w_{ij}} w_{ij}}{\sum_{i=1}^{I} w_{ij}} \qquad (10)$$

Further, the time required for updating calculation can be made shorter by calculating in advance the elements (11) and (12) appearing in Equation (10).

$$\sum_{i=1}^{I} w_{ij} \qquad (11)$$

$$\sum_{j=1}^{J} w_{ij} \qquad (12)$$

The reconstructed image generated by the calculation above is input as the initial image, and the same process is repeated for a number of times, whereby the data of the reconstructed image can be obtained.

FIG. 62 is a flowchart representing the process in accordance with the iterative method.

Referring to FIG. 62, when the process in accordance with the iterative method starts (S5102), the initial reconstructed image is set (S5104). As described above, all values may be 0, in the initial reconstructed image. Next, among a plurality of projection data corresponding to positions of a plurality of X-ray detectors, projection data to be the object of processing is selected (S5106).

Intermediate projection data is generated. The method for generating the intermediate projection data is as described above.

Then, not-yet-processed reconstruction pixel V in reconstruction field of view FOV is selected (S5110).

A detector pixel corresponding to the reconstruction pixel is found (S5112).

Based on the iteration equation, the value of reconstruction pixel V is updated (S5114).

Next, whether or not updating of all reconstruction pixels has been done is determined (S5116). If the process is not finished on all reconstruction pixels, the process returns to S5110. On the other hand, if the process has been finished, the flow proceeds to step S5118.

At S5118, it is determined whether or not the process has been done on all projection data. If the process is not yet finished for all projection data, the process returns to step S5106. If the process has been done on all projection data, the process proceeds to step S5120.

At S5120, it is determined whether the process has been repeated for a defined number of iterations. If not yet repeated, the process returns to step S5104 and the process is repeated using the present reconstruction pixel value as the initial reconstructed image, and if the process has been repeated for the defined number of iterations, the generation of reconstructed image ends (S5022).

As described above, a three-dimensional image of the object of inspection can be reconstructed from the projection data acquired by the X-ray detector.

In the analytical method, however, it is desired to maintain a constant relation of relative arrangement between the X-ray focal point and the X-ray detector even if the relative positions of the X-ray detector, the focal point and the object are changed to get each of the plurality of projection data, considering ease of computation when filtering is applied to each pixel of the X-ray detector. In other words, when the X-ray detector is viewed from the focal point, it is desirable that the positional relation between the focal point and the X-ray detector is kept constant, even if the angle of a portion included in the field of view of the object within the visible solid angle and/or position in the object may vary. Further, when the back-projection method is applied, it is desired that the plurality of projection data of portions included in the field of view of the object are acquired at every equal angle, in order to reduce artifact and the like.

In contrast, the iterative method does not involve any such limitation regarding the relative arrangement between the X-ray focal point and the X-ray detector.

Patent Document 1: Japanese Patent Laying-Open No. 2000-46760
Patent Document 2: Japanese Patent Laying-Open No. 2003-344316
Patent Document 3: Japanese Patent Laying-Open No. 2006-162335
Patent Document 4: Japanese Patent Publication No. 5-86218
Patent Document 5: Japanese Patent Laying-Open No. 2001-273860
Patent Document 6: Japanese Patent Laying-Open No. 2005-347174
Non-Patent Document 1: L. A. Feldkamp, L. C. Davis and J. W. Kress, "Practical cone-beam algorithm," Journal of the Optical Society of America. A, 612-619 (1984)

Non-Patent Document 2: A. H. Anderson and A. C. Kak, "SIMULTANEOUS ALGEBRAIC RECONSTRUCTION TECHNIQUE (SART): A SUPERIOR IMPLEMENTATION OF THE ART ALGORITHM," ULTRASONIC IMAGING 6, 81-94 (1984)

DISCLOSURE OF THE INVENTION

Problems to be Solved by the Invention

For in-line inspection at a plant, however, one-hundred percent inspection of products is required. Therefore, from the viewpoint of manufacturing efficiency, it is necessary to reduce time necessary for the X-ray inspection.

Further, in the X-ray imaging technique related to X-ray inspection described above, if the reconstructable inspection area is enlarged, time for image pick-up and 3D rendering (reconstruction) operations becomes longer. By way of example, for inspection of a printed board as mentioned above, acquisition of images of only a plurality of specific portions rather than the entire object of inspection may suffice in many circumstances. In such a situation, if the portions to be inspected of the object of inspection are positioned as isolated enclaves, it would be inefficient to prepare an X-ray detector that can cover the area (or volume) of the object in its entirety, since the size of the apparatus and the computational load would be increased.

Further, in the X-ray imaging technique related to X-ray inspection described above, it is necessary to move the imaging system or the works of inspection object, in order to change the inspection area, resulting in larger number of movable parts. This leads to problems of costs for manufacturing driving portions, maintenance and reliability, in addition to the problem of time required by the X-ray inspection mentioned above. By way of example, for inspection of a printed board as mentioned above, it is often the case that the portions to be inspected are a part of a printed board placed on a stage. In such a case, in order to provide the resulting X-ray image as an enlarged image, the X-ray detector must be driven at a position relatively far from the object of inspection, while the portions to be inspected are minute. Therefore, the imaging system must be driven with extremely high accuracy. For this purpose, the imaging system driving mechanism must be capable of taking necessary images with the smallest possible degree of freedom.

Therefore, there has been a need for an X-ray inspecting apparatus capable of selectively and quickly inspect a prescribed inspection area of an object of inspection as well as for an X-ray inspecting method utilizing such an X-ray inspecting apparatus.

Further, there has been a need for an X-ray inspecting apparatus with reduced number of movable parts, attaining high maintainability and reliability at low cost, as well as for an X-ray inspecting method utilizing such an X-ray inspecting apparatus.

Further, there has been a need for an X-ray inspecting apparatus capable of inspecting a plurality of portions of an object of inspection at high speed without moving the object of inspection, as well as for an X-ray inspecting method utilizing such an X-ray inspecting apparatus.

Means for Solving the Problems

According to an embodiment, the present invention provides an X-ray inspecting apparatus, forming images of X-ray transmitted through an area of inspection of an object on a plurality of detection surfaces, for executing a process of reconstructing an image of the area of inspection. The X-ray inspecting apparatus includes: a plurality of X-ray detectors smaller in number than the detection surfaces, for picking-up images on the plurality of detection surfaces; a detector driving unit driving some of the plurality of X-ray detectors and remaining ones of the plurality of X-ray detectors independently from each other; an X-ray output unit outputting X-ray such that the X-ray transmitted through the area of inspection enters the plurality of X-ray detectors moved to a plurality of image pick-up positions as the detection surfaces; and a control unit controlling an operation of the X-ray inspecting apparatus. The control unit includes an image acquisition control unit controlling timing of exposure by each of the X-ray detectors and the detector driving unit, an X-ray output control unit controlling the X-ray output unit, and an image reconstruction processing unit for reconstructing image data of the area of inspection, based on data of intensity distribution of the X-ray transmitted through the area of inspection, picked-up at the plurality of detection surfaces. The image acquisition control unit and the X-ray output control unit execute, in parallel, a process of image pick-up by the said some of the plurality of X-ray detectors at a first position among the plurality of image pick-up positions, and a process of moving the remaining ones of the plurality of X-ray detectors to a second position different from the first position among the plurality of image pick-up positions.

Preferably, the image acquisition control unit and the X-ray output control unit cause, for performing image pick-up of one area of inspection of the object, at a preset number of image pick-up positions for the image data reconstruction separately in a number of times, some of the plurality of X-ray detectors to execute a process of image pick-up at the first position and a process of moving to a next first position different from the first position after the image pick-up, and cause the remaining ones of the plurality of X-ray detectors to execute, in parallel with the process of image pick-up at the first position by the said some, a process of moving to the second position corresponding to next image pick-up, which is different from the first position, from the next first position and from the previous second position, and in parallel with the process of moving the said some to the next first position, a process of image pick-up at the second position.

Preferably, the X-ray output control unit includes an originating point setting unit setting, for the plurality of detection surfaces, each originating position of emission of the X-ray such that the X-ray passes through the area of inspection and is incident on each of the detection surfaces. The X-ray output unit moves an X-ray focal point position of X-ray source to each originating position and generates the X-ray.

Preferably, the X-ray output unit moves the X-ray focal point position by deflecting an electron beam to be incident on a target surface of a continuous surface of the X-ray source.

According to another embodiment, the present invention provides an X-ray inspecting apparatus, forming images of X-ray transmitted through an area of inspection of an object on a plurality of detection surfaces, for executing a process of reconstructing an image of the area of inspection. The X-ray inspecting apparatus includes: a plurality of X-ray detectors smaller in number than the detection surfaces, for picking-up images on the plurality of detection surfaces; a uniaxial driving unit for moving some of the plurality of X-ray detectors in a direction along a prescribed axis; an X-ray output unit outputting X-ray such that the X-ray transmitted through the area of inspection enters the plurality of X-ray detectors moved to a plurality of image pick-up positions as the detection surfaces; and a control unit controlling an operation of the X-ray inspecting apparatus. The control unit includes an image acquisition control unit controlling timing of exposure by each of the X-ray detectors and the detector driving unit, an X-ray output control unit controlling the X-ray output unit; and an image reconstruction processing unit for reconstructing image data of the area of inspection, based on data of intensity distribution of the X-ray transmitted through the area of inspection, picked-up at the plurality of detection surfaces.

Preferably, the uniaxial driving unit moves the plurality of X-ray detectors in a translational manner in a prescribed plane.

Preferably, each detection surface of the plurality of X-ray detectors has a rectangular shape. The detector driving unit includes a rotating unit rotating the plurality of X-ray detectors such that one end of the detection surface of the plurality of X-ray detectors intersects a direction toward the X-ray output unit at each image pick-up position.

Preferably, the image reconstruction processing unit reconstructs image data of the area of inspection by an iterative method.

Preferably, the image reconstruction processing unit reconstructs image data of the area of inspection by an analytical method.

According to a further embodiment, the present invention provides an X-ray inspecting apparatus, forming images of X-ray transmitted through an area of inspection of an object on a plurality of detection surfaces, for executing a process of reconstructing an image of the area of inspection. The X-ray inspecting apparatus includes: a plurality of X-ray detectors smaller in number than the detection surfaces, for picking-up images on the plurality of detection surfaces; an X-ray output unit outputting X-ray such that the X-ray transmitted through the area of inspection enters the plurality of X-ray detectors moved to a plurality of image pick-up positions as the detection surfaces; and a control unit controlling an operation of the X-ray inspecting apparatus. The control unit includes an image acquisition control unit controlling timing of exposure by each of the X-ray detectors and the detector driving unit, an X-ray output control unit controlling the X-ray output unit, and an image reconstruction processing unit for reconstructing image data of the area of inspection, based on data of intensity distribution of the X-ray transmitted through the area of inspection, picked-up at the plurality of detection surfaces. The image acquisition control unit and the X-ray output control unit execute, in parallel, a process of image pick-up by some of the plurality of X-ray detectors at a first position among the plurality of image pick-up positions, and a process of moving the remaining ones of the plurality of X-ray detectors to a second position different from the first position among the plurality of image pick-up positions. The X-ray output unit generates, to a plurality of X-ray detectors simultaneously in a state of image pick-up among the plurality of X-ray detectors arranged at the image pick-up positions, X-rays from a plurality of corresponding X-ray focal point positions. The X-ray inspecting apparatus further includes a shielding member allowing passage of the X-rays from the X-ray output unit, from a corresponding X-ray focal point position through the area of inspection to each of the detection surfaces of each of the X-ray detectors simultaneously in a state of image pick-up, and blocking an X-ray from a not-corresponding X-ray focal point position.

Preferably, the X-ray output unit moves the X-ray focal point position by deflecting an electron beam to be incident on a target surface of a continuous surface of the X-ray source. The X-ray output control unit controls the X-ray output unit such that the X-ray enters each of the plurality of X-ray detectors simultaneously in a state of image pick-up in a time-divisional manner.

According to a further embodiment, the present invention provides an X-ray inspecting apparatus, forming images of X-ray transmitted through an area of inspection of an object on a plurality of detection surfaces, for executing a process of reconstructing an image of the area of inspection. The X-ray inspecting apparatus includes: a plurality of X-ray detectors smaller in number than the detection surfaces, for picking-up images on the plurality of detection surfaces; a translational driving unit moving the plurality of X-ray detectors in a translational manner in a prescribed plane; an X-ray output unit outputting X-ray such that the X-ray transmitted through the area of inspection enters the plurality of X-ray detectors moved to a plurality of image pick-up positions as the detection surfaces; and a control unit controlling an operation of the X-ray inspecting apparatus. The control unit includes an image acquisition control unit controlling timing of exposure by each of the X-ray detectors and the detector driving unit, an X-ray output control unit controlling the X-ray output unit, and an image reconstruction processing unit for reconstructing image data of the area of inspection, based on data of intensity distribution of the X-ray transmitted through the area of inspection, picked-up at the plurality of detection surfaces.

Preferably, the detector driving unit includes a two-axis driving unit moving the plurality of X-ray detectors independently along directions of prescribed two axes.

According to a further embodiment, the present invention provides a method for X-ray inspection, picking-up images of X-rays transmitted through an area of inspection of an object by X-ray detectors corresponding to a plurality of detection surfaces, for executing a process of reconstructing an image of the area of inspection. The method for X-ray inspection includes the steps of: moving each of the X-ray detectors independently to an image pick-up position to be the detection surface; outputting X-ray such that the X-ray transmitted through the area of inspection enters the plurality of X-ray detectors moved to a plurality of the image pick-up positions respectively; executing, in parallel, a process of image pick-up by some of the plurality of X-ray detectors at a first position among the plurality of image pick-up positions, and a process of moving remaining ones, different from the said some, of the plurality of X-ray detectors, to a second position different from the first position among the plurality of image pick-up positions; and reconstructing image data of the area of inspection, based on data of intensity distribution of the X-ray transmitted through the area of inspection, picked-up at the plurality of detection surfaces.

Preferably, the step of executing includes, for performing image pick-up of one area of inspection of the object, at a preset number of image pick-up positions for the image data reconstruction separately in a number of times, the step of causing some of the plurality of X-ray detectors to execute a process of image pick-up at the first position and a process of moving to a next first position different from the first position after the image pick-up, and in parallel with the process of image pick-up at the first position by the said some, causing the remaining ones of the plurality of X-ray detectors to execute a process of moving to the second position corresponding to next image pick-up different from the first position, from the next first position and from previous the second position, and in parallel with the process of moving the said some to the next first position, a process of image pick-up at the second position.

Preferably, the step of outputting X-ray includes the step of moving the X-ray focal point position by deflecting an electron beam to be incident on a target surface of a continuous surface of the X-ray source.

Effects of the Invention

By the X-ray inspecting method and the X-ray inspecting apparatus in accordance with the present invention, a prescribed inspection area of an object of inspection can be inspected selectively at high speed.

Further, by the X-ray inspecting method and the X-ray inspecting apparatus in accordance with the present invention, the number of movable parts can be reduced and X-ray inspection with high maintainability and reliability can be executed at a low cost.

Further, by the X-ray inspecting method and the X-ray inspecting apparatus in accordance with the present invention, it is possible to inspect a plurality of portions of an object of inspection at a high speed.

Figure 1:
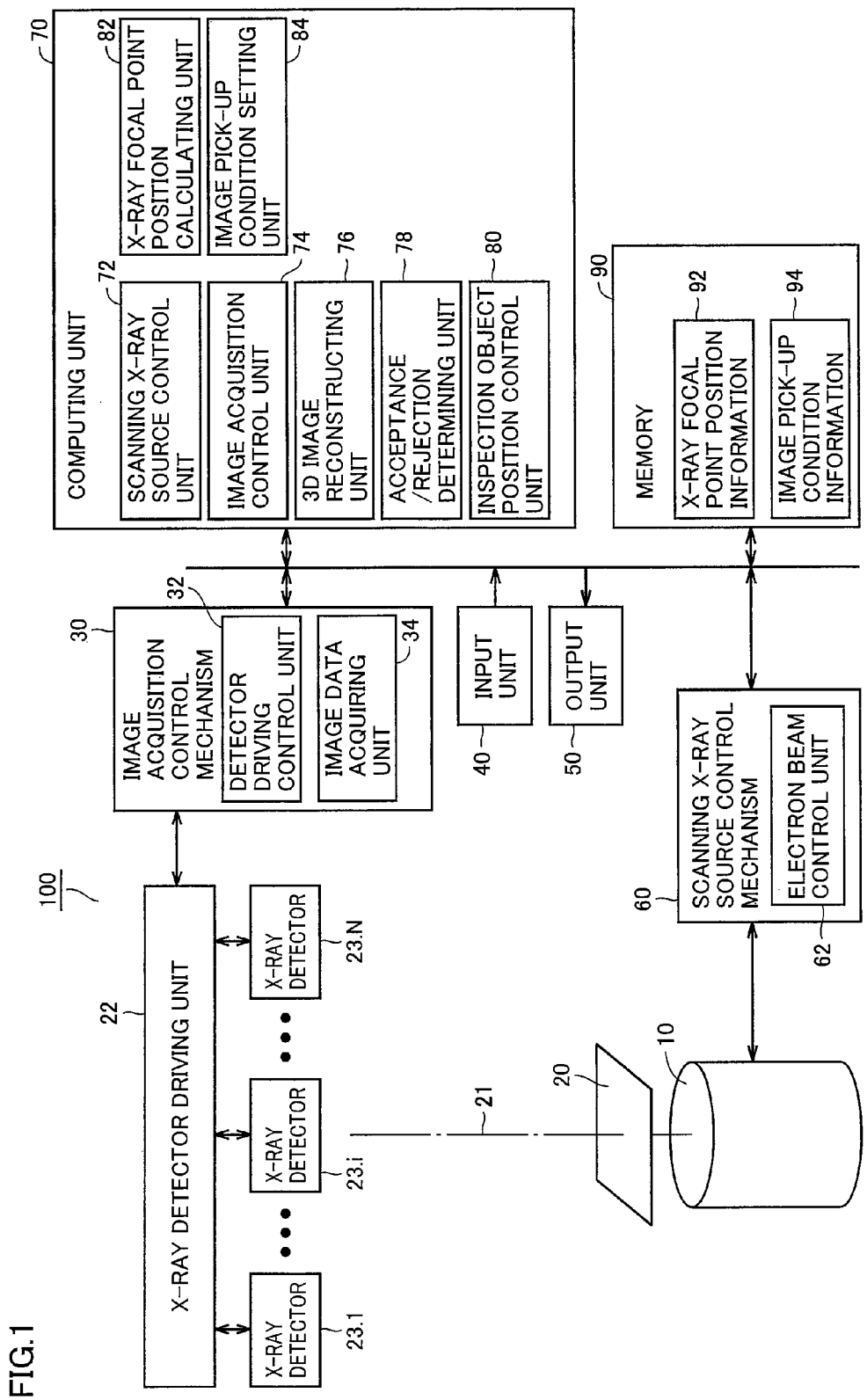
FIG. 1 is a schematic block diagram of an X-ray inspecting apparatus 100 in accordance with the present invention.

DESCRIPTION OF THE REFERENCE SIGNS 10 scanning X-ray source, 11 target, 12 deflection yoke, 13 electron beam converging coil, 14 high-voltage power supply, 15 vacuum pump, 19 electron gun, 16 electron beam, 17 X-ray focal point position, 18 X-ray, 20 object of inspection, 22 sensor base, 23 X-ray detector, 24 slider, 25 X-ray module, 26 X-ray receiving unit, 27 data cable, 28 power cable, 29 data processing unit, 30 image acquisition control mechanism, 32 detector driving control unit, 34 image data acquiring unit, 40 input unit, 50 output unit, 60 scanning X-ray source control mechanism, 62 electron beam control unit, 70 computing unit, 72 scanning X-ray source control unit, 74 image acquisition control unit, 76 3D image reconstructing unit, 78 acceptance/rejection determining unit, 80 inspection object position control unit, 82 X-ray focal point position calculating unit, 84 image pick-up condition setting unit, 90 memory, 92 X-ray focal point position information, 94 image pick-up condition information, 100 X-ray inspecting apparatus.

In the following, embodiments of the present invention will be described with reference to the figures. In the following description, the same components are denoted by the same reference characters. Their names and functions are also the same. Therefore, detailed description thereof will not be repeated.

Embodiment 1

1. Configuration of the Present Invention

FIG. 1 is a schematic block diagram of an X-ray inspecting apparatus 100 in accordance with the present invention.

Referring to FIG. 1, X-ray inspecting apparatus in accordance with the present invention will be described. It is noted that structures, dimensions, shapes and other relative arrangements described in the following are not intended to limit the scope of the invention to such values unless specified to the contrary.

X-ray inspecting apparatus 100 includes a scanning X-ray source 10 emitting an X-ray with an axis 21 being the central axis, and an X-ray detector driving unit 22 having a plurality of X-ray detectors 23.1 to 23.N mounted thereon, for driving each of X-ray detectors 23.1 to 23.N to a designated position, as will be described later. Further, between scanning X-ray source 10 and X-ray detectors 23.1 to 23.N, an object of inspection 20 is positioned. X-ray inspecting apparatus 100 further includes: an image acquisition control mechanism 30 for controlling driving of each of X-ray detectors 23.1 to 23.N by X-ray detector driving unit 22 and acquisition of image data from X-ray detectors 23.1 to 23.N; an input unit 40 for receiving instruction input and the like from the user; and an output unit 50 for outputting results of measurement and the like to the outside. X-ray inspecting apparatus 100 further includes a scanning X-ray source control mechanism 60, a computing unit 70 and a memory 90. In such a configuration, computing unit 70 executes a program, not shown, stored in memory 90, for controlling various components and executes prescribed operations.

Scanning X-ray source 10 is controlled by scanning X-ray source control mechanism 62, and irradiates the object of inspection 20 with X-ray.

Figure 2:
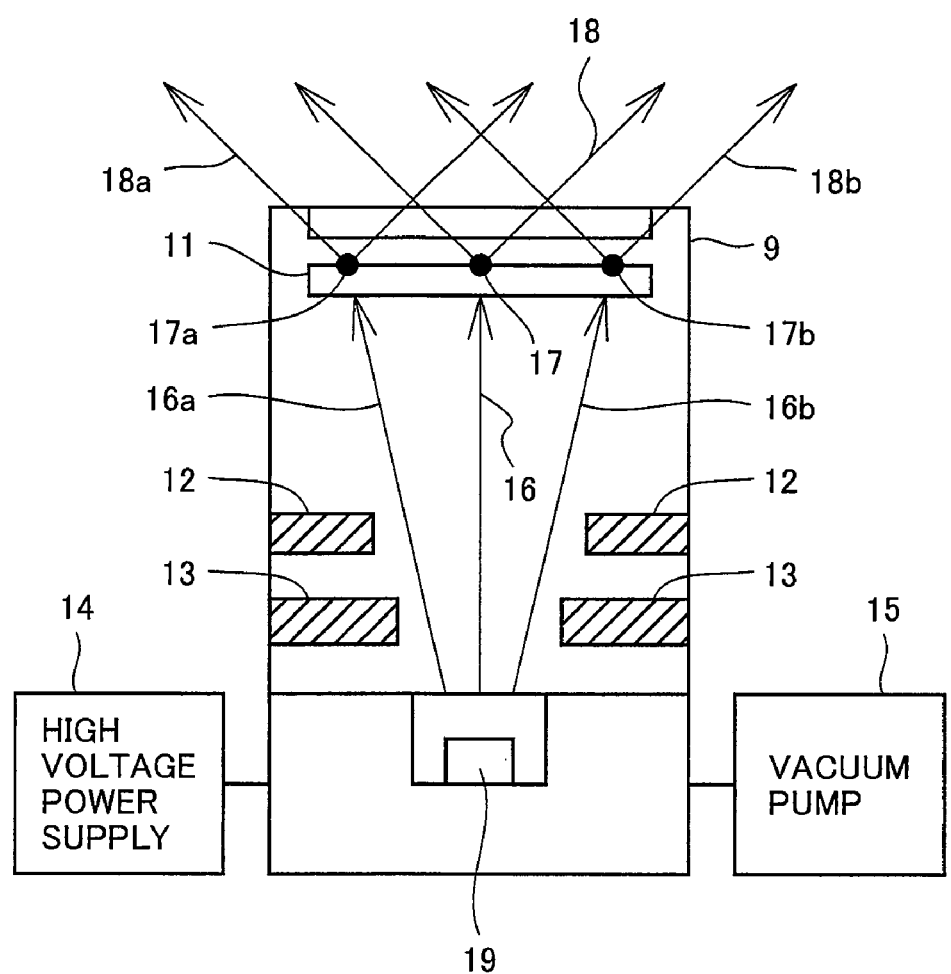
FIG. 2 is a cross-sectional view showing a configuration of a scanning X-ray source 10.

FIG. 2 is a cross-sectional view showing a structure of scanning X-ray source 100.

Referring to FIG. 2, in scanning X-ray source 10, from an electron gun 19 controlled by electron beam control unit 62, an electron beam 16 is emitted to a target 11 of, for example, tungsten. At a position where electron beam 16 impinges on the target (X-ray focal point position 17), X-ray 18 is generated and emitted (output). The electron beam system is housed in a vacuum container 9. Inside of vacuum container 19 is kept evacuated by a vacuum pump 15, and electron beam 16 accelerated by a high-voltage power supply 14 is emitted by electron gun 19.

In scanning X-ray source 10, electron beam 16 is converged by an electron beam converging coil 13 and deflected by a deflecting yoke 12 thereafter, whereby the location where electron beam 16 impinges on target 11 can arbitrarily changed. By way of example, an electron beam 16a deflected by deflecting yoke 12 impinges on target 11, and X-ray 18a is output from the X-ray focal point position 17a. Similarly, an electron beam 16b deflected by deflecting yoke 12 impinges on target 11, and X-ray 18b is output from the X-ray focal point position 17b. In the present invention, scanning X-ray source 10 is a transmitting type source unless otherwise specified. As will be described later, when X-ray is to be generated at a position to be the originating point of X-ray emission set in accordance with the portion to be inspected of the object of inspection (hereinafter referred to as the "X-ray emission originating point"), in order to improve degree of freedom in setting the position, the target should preferably have a continuous surface, rather than a ring shape. In the following description, it will be simply denoted as X-ray focal point position 17 in general, unless the position is specifically described in a distinguishing manner.

If the X-ray focal point position is to be moved to each X-ray emission originating point as mentioned above, the position of X-ray source itself may be mechanically moved as needed. With the structure shown in FIG. 2, however, it is unnecessary to mechanically move the X-ray source, if the X-ray focal point position is to be moved to the X-ray emission originating point, within a certain range. Therefore, an X-ray inspecting apparatus having good maintainability and reliability can be realized. It is also possible to provide a plurality of X-ray sources and to switch among the sources depending on the emission originating position, as will be described later.

In other words, the "X-ray emission originating position" means the spatial position that can be identified if the spatial position of the X-ray detectors 23.i (i is a specific one from 1 to N) used for image pick-up and the spatial position of the portion to be inspected of object of inspection 20 are identified, and the X-ray focal point position means the actual point on the target where the X-ray is actually output. Therefore, to bring the X-ray focal point position to the "X-ray emission originating point" is possible by electron beam scanning with the scanning X-ray source, or by mechanically moving the X-ray source itself.

Returning to FIG. 1, when the position of object of inspection 20 arranged between scanning X-ray source 10 and X-ray detector 23 (in the following, "X-ray detectors 23.1 to 23.N" are generally referred to as "X-ray detector 23") is to be moved, it may be moved to an arbitrary position using an X-Y-Z stage, or it may be arranged at a position for inspection by moving in one direction using, for example, a belt conveyer. If the object of inspection is small as in the case of a printed board, the object of inspection may be moved while scanning X-ray source 10 and X-ray detector 23 are fixed. If the object of inspection is large as in the case of a glass substrate and it is difficult to move the object of inspection arbitrarily, scanning X-ray source 10 and X-ray detector 23 may be moved, keeping constant the positions of scanning X-ray source 10 and X-ray detector relative to each other.

X-ray detector 23 is a two-dimensional X-ray detector that detects X-ray output from scanning X-ray source 10 and passed through object of inspection 20 and forms an image therefrom. It is implemented, for example, by a CCD (Charge Coupled Device) camera, or an I. I. (Image Intensifier) tube.

In the present invention, since a plurality of X-ray detectors are arranged on X-ray detector driving unit 22, an FPD (flat panel detector) securing better space efficiency is desirable. Further, highly sensitive detector is desired to enable use in in-line inspection. Therefore, a direct conversion FPD using CdTe is particularly desirable.

Details of the structure of X-ray detector driving unit 22 will be described later.

Image acquisition control mechanism 30 includes: a detector driving control unit 32 for controlling X-ray detector driving unit 22 such that X-ray detector 23 is moved to a position designated by computing unit 70; and an image data acquiring unit 34 for acquiring image data of X-ray detector 23 designated by computing unit 70. In accordance with the situation of image pick-up, one or a plurality of X-ray detectors may be designated at one time for acquiring image data by computing unit 70, as will be described later.

The position of X-ray detector 23 driven by X-ray detector driving unit 22 can be known by a position sensor (not shown), and it can be taken to computing unit 70 through detector driving control unit 32.

Further, it is desirable that X-ray detector driving unit 22 is movable upward/downward, to adjust magnification. In that case, the position of X-ray detector driving unit 22 in the upward/downward direction can be known by a position sensor (not shown), and it can be taken to computing unit 70 through detector driving control unit 32.

Input unit 40 is an operation input device for receiving inputs by the user.

Output unit 50 is a display for displaying X-ray image and the like provided by computing unit 70.

Specifically, the user can execute various inputs through input unit 40, and various results of operations obtained by the processes of computing unit 70 are displayed on output unit 50. The image displayed on output unit 50 may be output for visual determination of acceptance/rejection by the user, or it may be output as a result of acceptance/rejection determination made by an acceptance/rejection determining unit 78, which will be described later.

Computing unit 70 includes a scanning X-ray source control unit 72, an image acquisition control unit 74, a 3D image reconstructing unit 76, acceptance/rejection determining unit 78, an inspection object position control unit 80, an X-ray focal point position calculating unit 82, and an image pick-up condition setting unit 84.

Scanning X-ray source control unit 72 determines the X-ray focal point position and X-ray energy, and transmits a command to scanning X-ray source control mechanism 60.

Image acquisition control unit 74 determines an X-ray detector 23 to acquire an image, among X-ray detectors 23 driven by X-ray detector driving unit 22 to the designated position, and transmits a command to image acquisition control mechanism 30. Further, it acquires image data from image acquisition control mechanism 30.

3D image reconstructing unit 76 reconstructs 3D image from a plurality of image data acquired by image acquisition control unit 74.

Acceptance/rejection determining unit 78 determines whether the object of inspection is acceptable or not, based on fluoroscopic data or 3D image data reconstructed by 3D image reconstructing unit 76. By way of example, it recognizes the shape of a solder ball and determines whether or not the shape is within a predetermined tolerable range, and thereby determines whether the object is acceptable or not. An algorithm for acceptance/rejection determination, or input information for the algorithm is different object by object and, therefore, it is obtained from image pick-up condition information 95.

Inspection object position control unit 80 controls a mechanism (not shown) for moving object of inspection 20, for example, a stage.

X-ray focal point position calculating unit 82 calculates, when an inspection area in which object of inspection 20 exists is to be inspected, the X-ray focal point position or irradiation angle to the inspection area. Details will be described later.

Image pick-up condition setting unit 84 sets conditions for outputting X-ray from scanning X-ray source 10, depending on the object of inspection 20. For example, the conditions include voltage applied to X-ray source and image pick-up time.

Memory 90 includes X-ray focal point position information 92 storing the X-ray focal point position calculated by X-ray focal point position calculating unit 82, image pick-up condition information 94 storing the image pick-up conditions set by image pick-up condition setting unit 84 and information related to the algorithm for acceptance/rejection determination, and a program for realizing various functions executed by computing unit 70. What is required of memory 90 is to simply store data and it is implemented by a storage device such as an RAM (Random Access Memory), an EEPROM (Electrically Erasable and Programmable Read-Only Memory), or an HDD (Hard Disc Drive).

(Configuration 1 of X-Ray Detector Driving Unit 22: Configuration for Independent Detector Movement)

In X-ray inspecting apparatus 100, there is a relation that (number of X-ray detectors)<<(number of images picked-up for reconstruction). The reason for this is that it is generally impractical to provide the detectors corresponding to the necessary number of images to be picked-up, from the viewpoint of costs of FPDs. Therefore, at the time when images exceeding the number of X-ray detectors are to be picked up, it is necessary to mechanically move (X-ray detector)/(X-ray source (X-ray source))/(stage having the object of inspection placed thereon). During such mechanical movement, image pick-up process cannot be executed.

X-ray inspecting apparatus 100 in accordance with Embodiment 1 enables reduction of this vacant time that does not contribute to higher speed of operation of the system as a whole, as will be described in the following.

(Problem of Time Loss in Image Pick-Up Process Resulting from Mechanical Movement)

In the following, before describing the configuration and operation of X-ray inspecting apparatus in accordance with Embodiment 1, as a background, an outline of the configuration of moving mechanism allowing mechanical movement of the imaging system of the object of inspection in other possible X-ray inspecting apparatus as well as its problem will be described.

Figure 3:
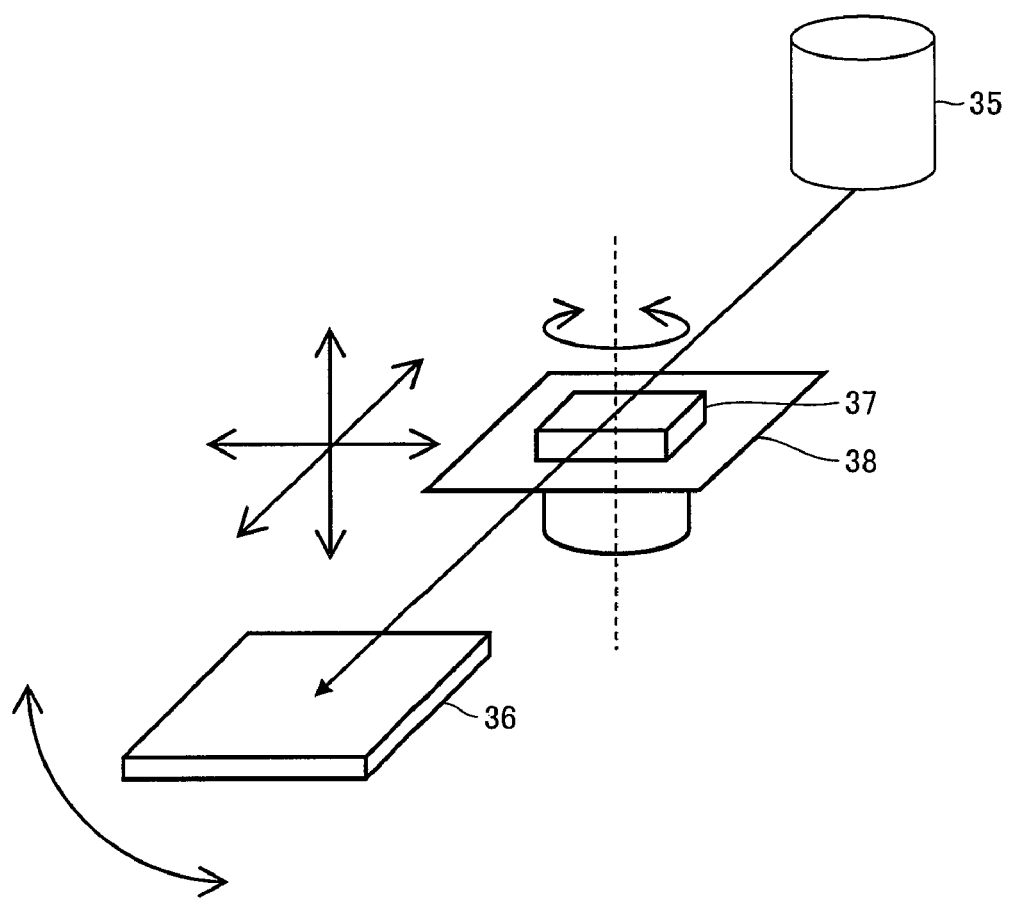
FIG. 3 is a schematic illustration showing a first example of a moving mechanism.

FIG. 3 is a schematic illustration showing a first example of a moving mechanism. In the example shown in FIG. 3, an X-ray source 35 and an X-ray detector 36 are fixed, and a field of view 37 is mechanically moved (rotated) on stage 38, whereby the necessary number of images for reconstruction are picked-up.

Figure 4:
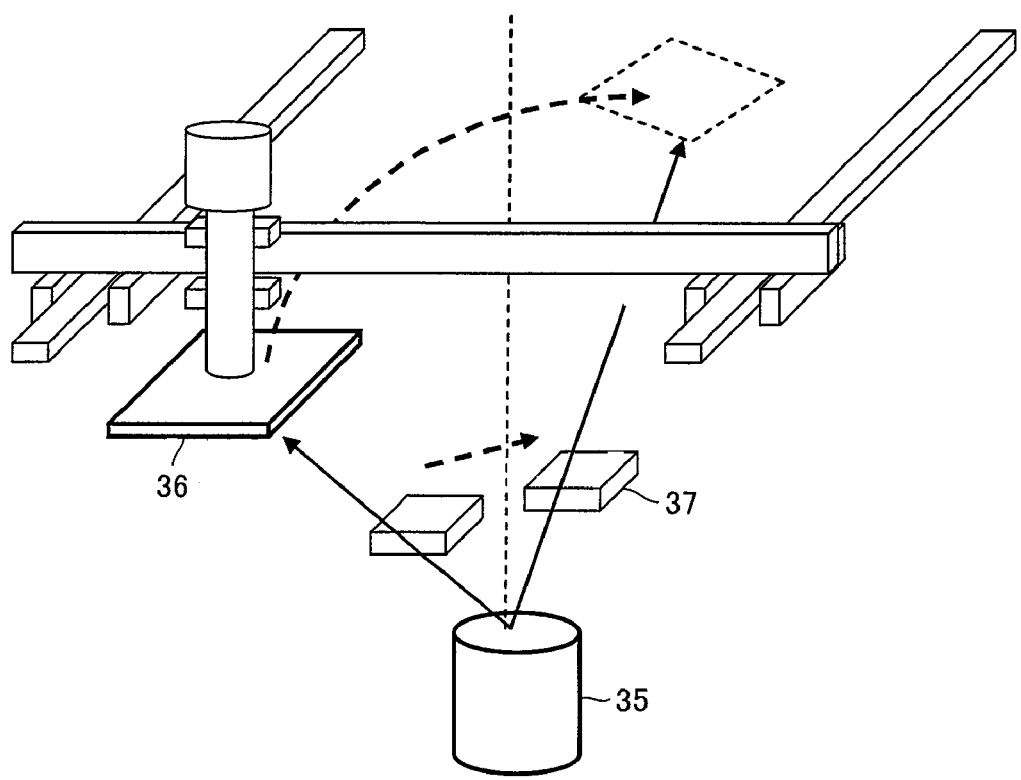
FIG. 4 is a schematic illustration showing a second example of a moving mechanism.

FIG. 4 is a schematic illustration showing a second example of a moving mechanism. In the example shown in FIG. 4, X-ray detector 36 is mechanically translated in the X-Y plane, and rotated in θ direction, while field of view 37 (inspected portion of the object of inspection) is also translated in the X-Y plane, whereby the necessary number of images for reconstruction are picked-up.

Figure 5:
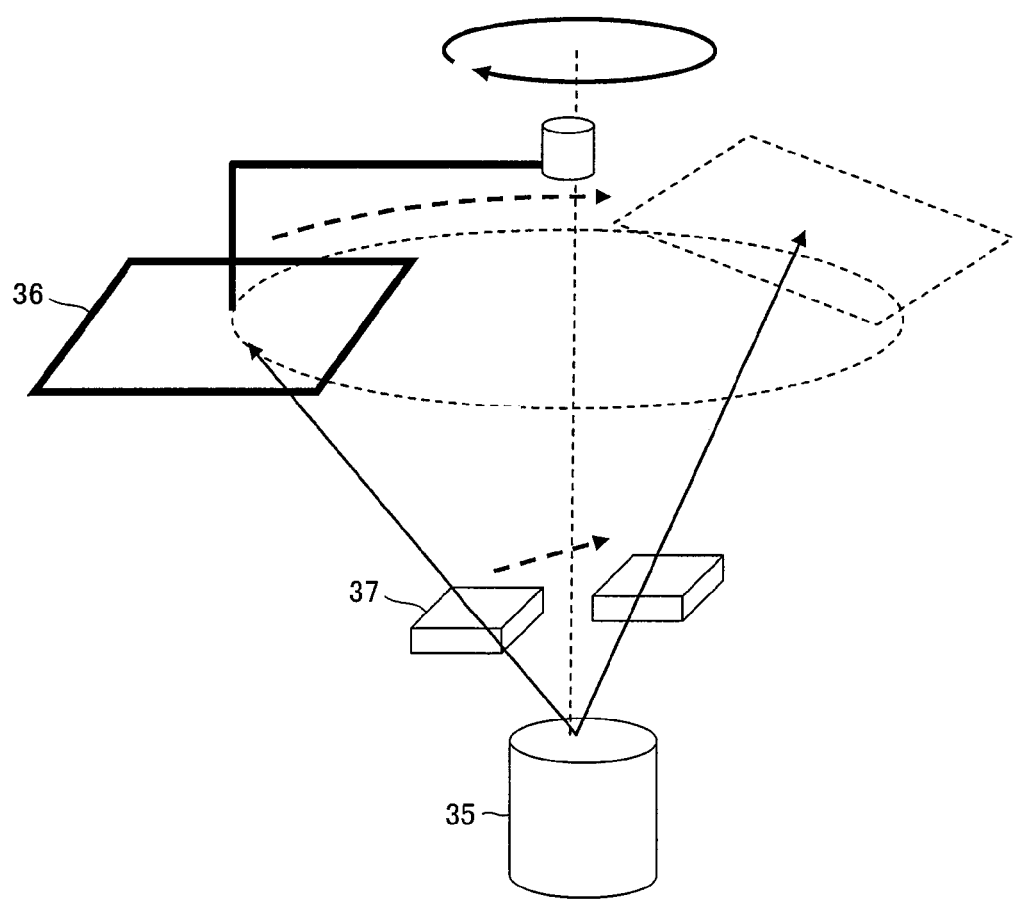
FIG. 5 is a schematic illustration showing a third example of a moving mechanism.

FIG. 5 is a schematic illustration showing a third example of a moving mechanism. In the example shown in FIG. 5, X-ray detector 36 is mechanically rotated in θ direction, while field of view 37 (inspected portion of the object of inspection) is translated in the X-Y plane, whereby the necessary number of images for reconstruction are picked-up.

As will be described in detail in the following, the examples of FIGS. 3 to 5 all involve mechanical movement of the imaging system or the object of inspection, in order to obtain picked-up data of a plurality of images. During the movement, the image pick-up is impossible. The time for movement poses a bottle neck in increasing the system speed.

Figure 6:
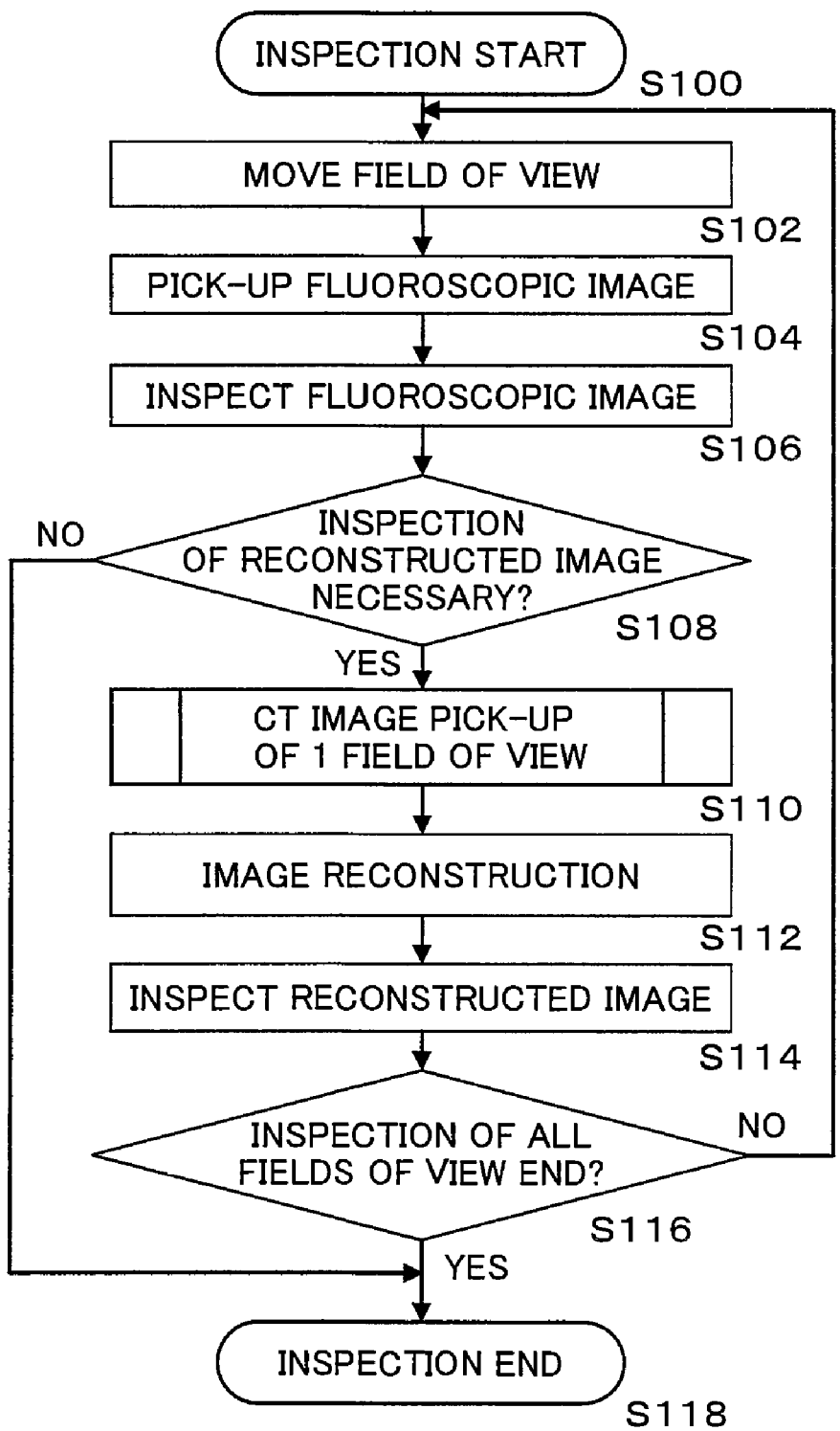
FIG. 6 is a flowchart of an overall inspection for reconstructed image inspection by any of the moving mechanisms shown in FIGS. 3 to 5.

FIG. 6 is a flowchart of an overall inspection for reconstructed image inspection by any of the moving mechanisms shown in FIGS. 3 to 5.

Referring to FIG. 6, first, when the process starts (S100), the portion to be inspected (field of view) of the object of inspection is moved to a position allowing image pick-up (S102). Specifically, in order to obtain a fluoroscopic image, the stage having the object of inspection placed thereon and the X-ray detector are moved to prescribed positions.

Then, the fluoroscopic image is picked-up (S104), and the fluoroscopic image is inspected, so that whether the field of view of the object of inspection (the scope picked-up in the fluoroscopic image) is acceptable or not is determined from the thus acquired fluoroscopic image (S106).

Thereafter, determination is made as to whether or not an inspection by a reconstructed image is necessary (S108).

If the inspection by the reconstructed image is unnecessary, the inspection ends (S118).

If the inspection by the reconstructed image is necessary, CT image pick-up is performed on one field of view (S110). In the CT image pick-up, a plurality of images of a field of view in the object of inspection (the area to be reconstructed, or the area similar to the scope of fluoroscopic image pick-up described above) are taken from different directions.

Next, from the images picked-up from the plurality of different directions, a reconstructed image is generated (S112). Then, determination of acceptance/rejection is made using the reconstructed image (S114).

Further, whether the inspection of all fields of view is finished or not is determined (S116). If inspection is not yet finished, the process returns to step S102. If inspection of all fields of view is finished, the inspection ends (S118).

Figure 7:
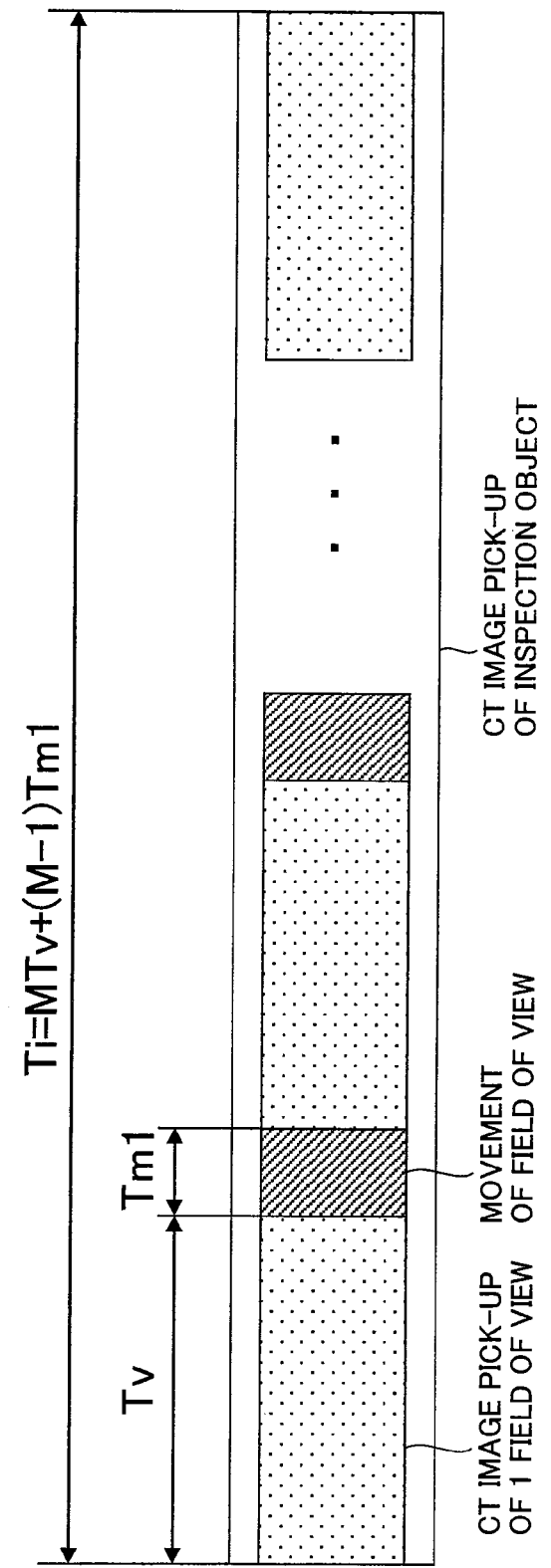
FIG. 7 is a timing chart of the overall inspection in accordance with the flowchart of FIG. 6.

FIG. 7 is a timing chart of the overall inspection in accordance with the flowchart of FIG. 6. In the following description, it is assumed that the object of inspection is divided into M (for example, four) fields of view, and N images are picked-up as CT images. Definitions of signs will be given below.

Here, the time for picking-up images of the entire object of inspection is represented by Ti, the time for picking-up images of one field of view is represented by Tv, the time required for mechanical movement (movement of the stage/X-ray detector and the like) is represented by Tm, and the time of image pick-up (exposure by X-ray detector) is represented by Ts.

As shown in FIG. 7, the CT image pick-up time T1 of the entire object of inspection is the sum of the time for image pick-up of M fields of view and the time of movement Te (movement of field of view) of (M−1) times, and hence, it is given by Equation (13) below.

$$Ti = MTv + (M-1)Te \tag{13}$$

Figure 8:
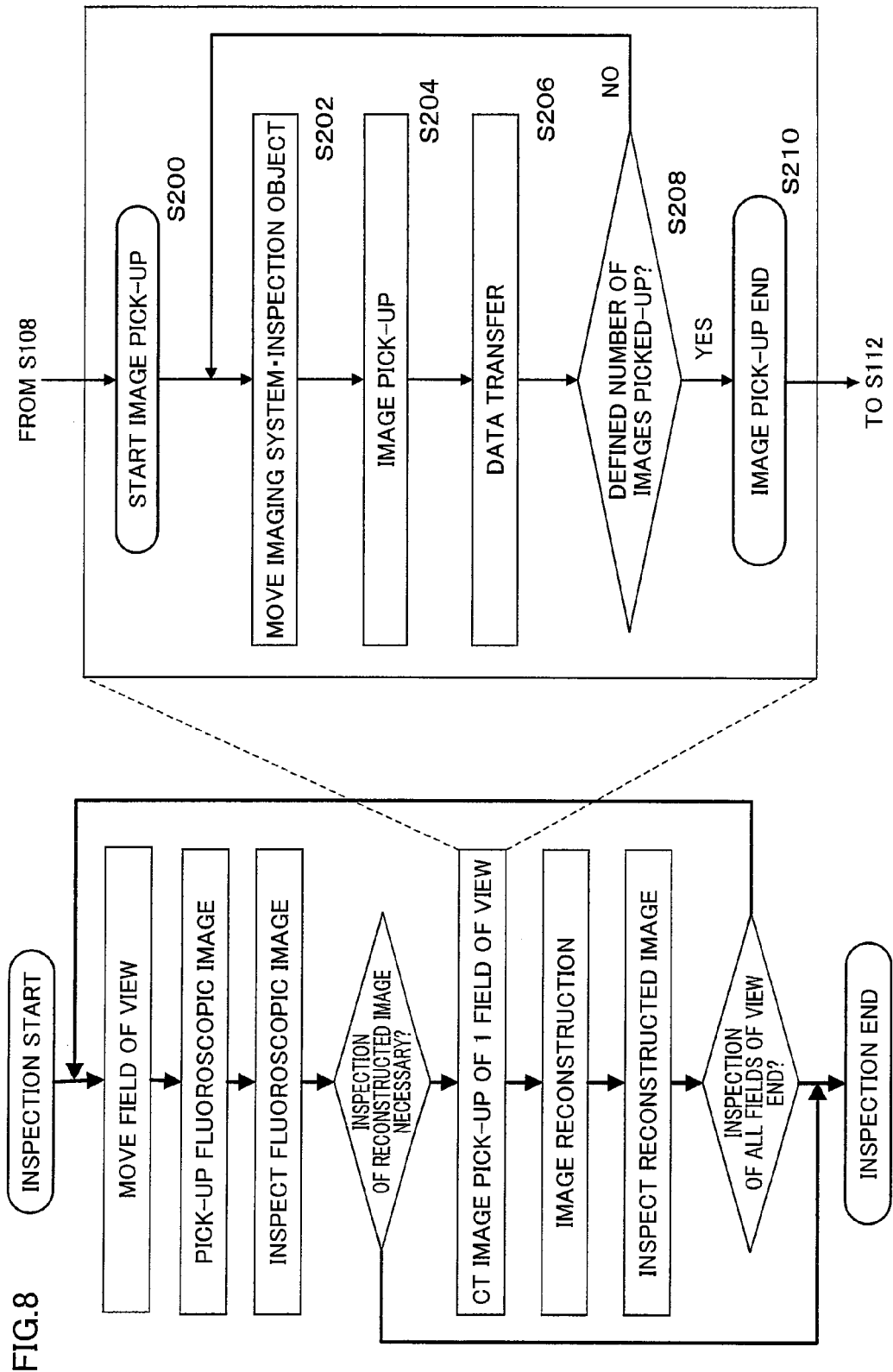
FIG. 8 is a flowchart representing the process of CT image pick-up of one field of view shown in FIG. 6.

FIG. 8 is a flowchart representing the process of CT image pick-up of one field of view shown in FIG. 6.

Referring to FIG. 8, when CT image pick-up of one field of view starts (S200), first, the imaging system and/or the object of inspection is moved to the position of image pick-up for the present field of view (S202). The position of image pick-up can be automatically calculated from the design information such as CAD data. Since the object of inspection is placed on the stage, it is possible to move the field of view by moving or rotating the stage.

Next, an image of the portion of field of view of the object of inspection is picked up (S204). The image pick-up data of the object of inspection can be obtained by directing X-ray from the X-ray source and exposing X-ray detector. The exposure time can be determined in advance considering the size of the object of inspection, the intensity of X-ray generated from the X-ray source and the like.

Next, the image data picked up by the X-ray detector is transferred to the computing unit (S206). Specifically, for reconstruction of the picked-up image data, the data is transferred to the computing unit that performs the reconstructing process.

Then, determination is made as to whether a defined number of images has been picked up (S208). The defined number may be determined from design information such as CAD data before inspection, or it may be determined by visual observation by an operator. If the defined number is reached, CT image pick-up is stopped (S210), and the image reconstruction process (S112 of FIG. 6) is executed. If the defined number is not yet reached, the process returns to S202, and the imaging system and/or the object of inspection is moved for picking up images of the field of view from the next position of image pick-up.

Figure 9:
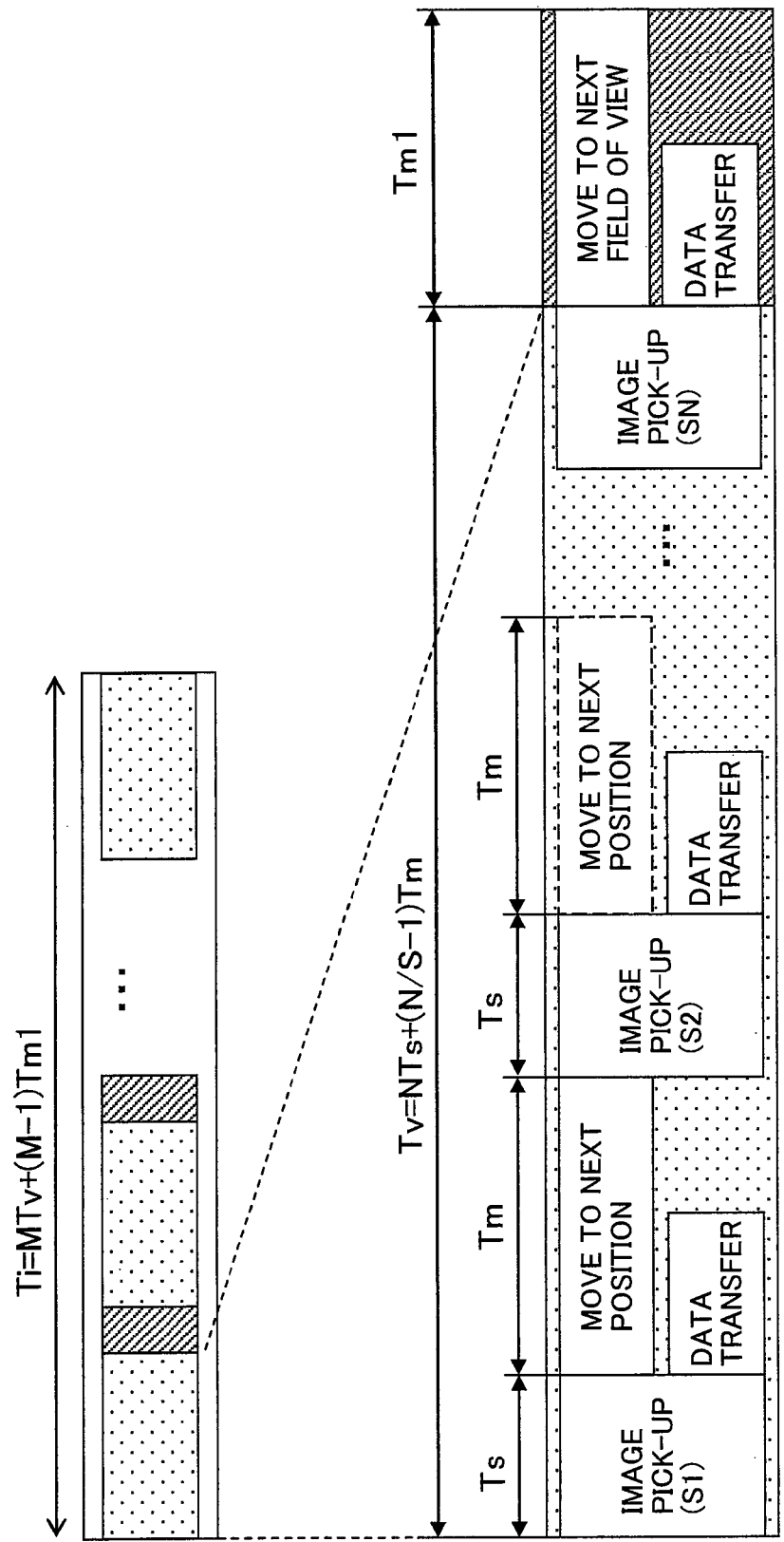
FIG. 9 is a timing chart of a process in which image pick-up is done in a plurality of directions, in the process of CT image pick-up of one field of view shown in FIG. 8.

FIG. 9 is a timing chart of a process in which imaging is done in a plurality of directions, in the process of CT image pick-up of one field of view shown in FIG. 8.

Here, it is assumed that there are S X-ray detectors mounted on one circular rotation mechanism in the structure such as shown in FIG. 5 and these are rotated together by a detector rotating mechanism. It is noted that imaging is done by one X-ray detector at one image pick-up operation.

Here, the time Tv of CT image pick-up of one field of view by the X-ray detector is the sum of N times the image pick-up time Ts (indicated by S1, S2, . . . SN in the figure) and the necessary time of mechanical movement and, hence, it is given by Equation (14) below.

When there are $S$ detectors: $Tv=NTs+(N/S-1)Tm$

When there is one detector: $Tv=NTs+(N-1)Tm$ (14)

Here, it is assumed that data transfer of picked-up images is performed simultaneously with the mechanical movement. If 16 images are to be picked up using one detector, the time will be Tv=16Ts+15Tm.

(Configuration and Operation of X-Ray Inspecting Apparatus in Accordance with Embodiment 1)

In the following, the configuration and operation of X-ray inspecting apparatus 100 in accordance with Embodiment 1 will be described.

In X-ray inspecting apparatus 100 in accordance with Embodiment 1, the field of view does not mechanically move (at the time of image pick-up), as will be described in the following. Therefore, in order to obtain image data of a plurality of angles, the position of X-ray focal point and the position of X-ray detector must be changed.

For high-speed movement of X-ray focal point position, the scanning X-ray source is used. As will be described in a modification, a plurality of fixed focal-point X-ray sources may be used. For moving the position of X-ray detector 23, the following configuration is used.

1) At least two X-ray detectors 23 are provided, and X-ray detector driving unit 22 is adapted to allow independent movement thereof 2) During image pick-up by X-ray detector 23.1, the other X-ray detector 23.2 is moved to a prescribed position to be ready for image pick-up.

By such an approach, when image pick-up is to be done, X-ray detector 23.2 has already been moved to the prescribed position and, therefore, by moving the X-ray focal point position at high speed, the wasteful time of mechanical movement can be reduced.

Figure 10:
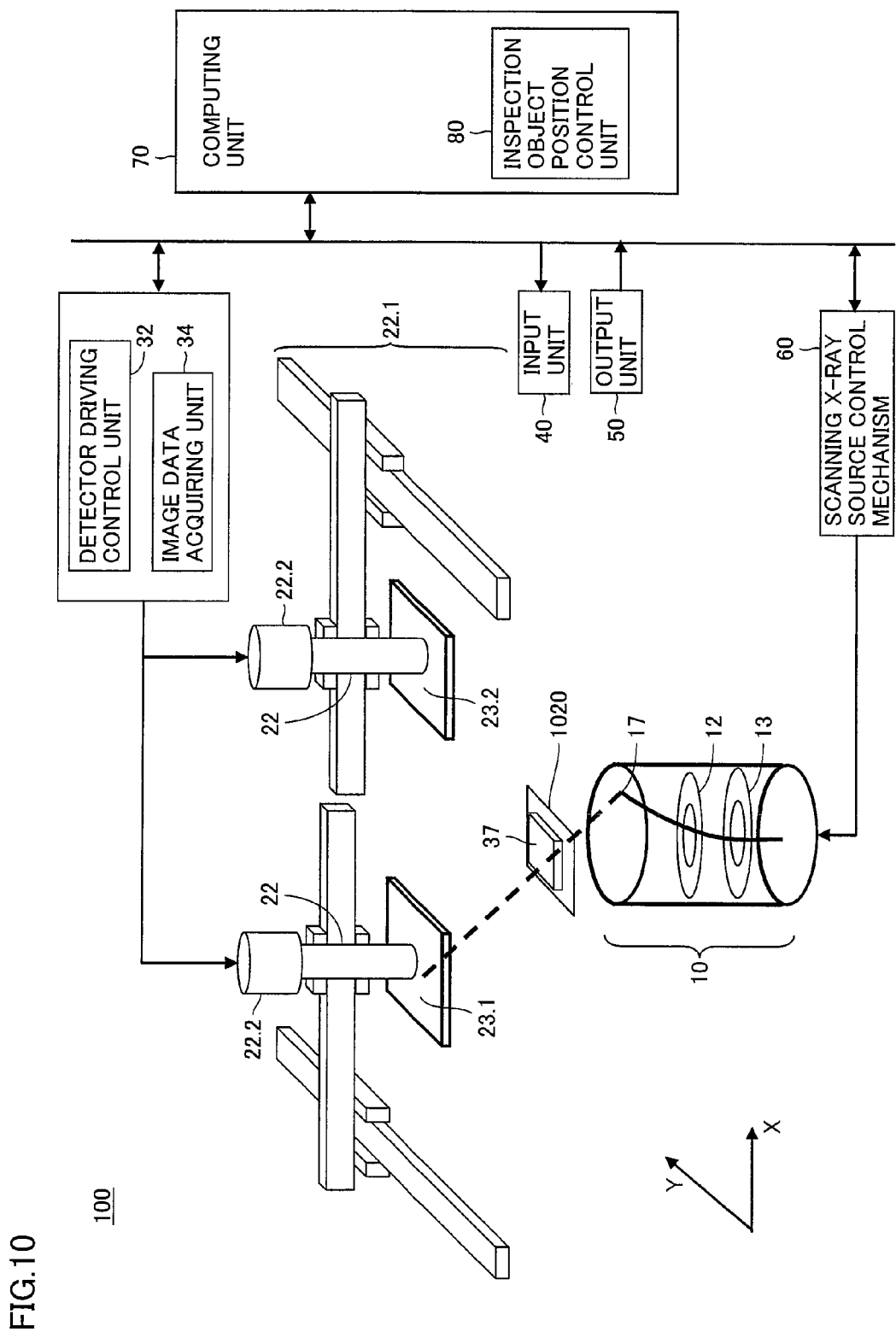
FIG. 10 illustrates a configuration of X-ray inspecting apparatus 100 in accordance with Embodiment 1.

FIG. 10 illustrates a configuration of X-ray inspecting apparatus 100 in accordance with Embodiment 1. The same portions as those in FIG. 1 are denoted by the same reference characters, and portions necessary for the description are extracted from portions directly related to the control of X-ray focal point position, the control of X-ray detector position and the control of the position of object of inspection.

Referring to FIG. 10, X-ray detector driving unit 22 is an XYθ operation mechanism capable of driving X-ray detectors 23.1 and 23.2 with the degree of freedom in XYθ, and as the X-ray source 10, a scanning X-ray source is used.

In the configuration shown in FIG. 10, in order to move the position of object of inspection, an inspection object position driving mechanism 1020 (for example, an X-Y stage) and inspection object position control unit 80 are provided.

Though two independently movable X-ray detectors are used in the example of FIG. 10, two or more X-ray detectors may be used.

The independent X-Y-θ operation is possible in X-ray detector 23.1 and X-ray detector 23.2. As will be described later, depending on the manner of driving X-ray detector 23, the mechanism for rotation in θ direction is not always necessary.

X-ray detector driving unit 22 includes an orthogonal two-axis robot arm 22.1 and a detector support unit 22.2 having a rotational axis, and moves/rotates X-ray detector 23. It is noted that other mechanism having a configuration allowing movement in the X-Y direction or θ rotation in the X-Y plane and having similar functions related to the movement of X-ray detector may be used.

Further, the X-Y movement of a field of view 37 of the object of inspection independent from X-ray detectors 23.1 and 23.2 is made possible by inspection object position driving mechanism 1020 controlled by inspection object position control unit 80 in computing unit 70. Further, as described above, the scanning X-ray source of X-ray source 10 can move the X-ray focal point position 17 to an arbitrary position on the X-ray target at high speed.

Computing unit 70 transmits instructions to detector driving control unit 32, image data acquiring unit (X-ray detector controller) 34 and scanning X-ray source control mechanism 60, and executes a program represented by the flowchart of inspection process as will be described later. Further, it controls operations of the inspecting apparatus in accordance with an input from input unit 40, and it can output status of each portion or results of inspection from output unit 50.

Inspection object position control mechanism 1020 includes an actuator and a mechanism for fixing the object of inspection, and moves the object of inspection in accordance with an instruction from inspection object position control unit 80.

X-ray detector driving unit 22 includes orthogonal two-axis robot arm 22.1 and detector support unit 22.2 having a rotational axis, and moves/rotates X-ray detector 23 to a designated position in accordance with an instruction from computing unit 70 through detector driving control unit 32.

Further, detector driving control unit 32 transmits position information of X-ray detector 23 at the time point to computing unit 70.

Computing unit 70 acquires X-ray fluoroscopic image and transfers image data at a timing designated by an instruction through detector driving control unit 32.

X-ray source 10 generates an electron beam in accordance with an instruction from computing unit 70 through scanning X-ray source control mechanism 60, converges the electron beams on a designated position on the target by electron beam converging coil 13 and deflection yoke 12, and moves X-ray focal point 17 at high speed.

Figure 11A:
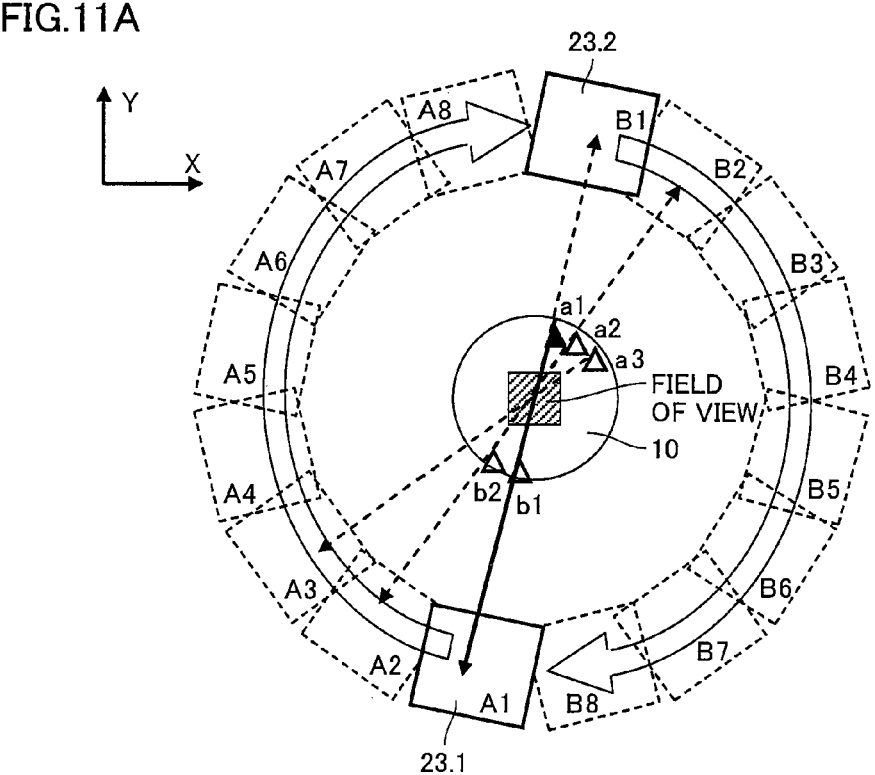
FIG. 11A is a top view showing movement trajectory of X-ray detector 23 and the scanning X-ray source, in the configuration of X-ray inspecting apparatus 100 shown in FIG. 10.
Figure 11B:
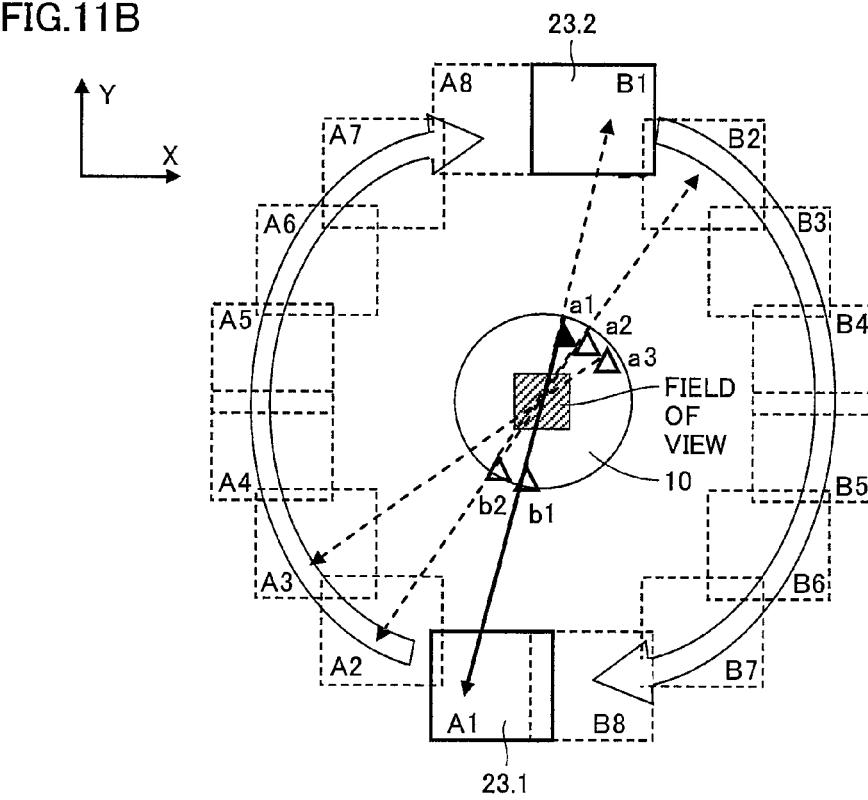
FIG. 11B is a top view showing movement trajectory of X-ray detector 23 and the scanning X-ray source, in the configuration of X-ray inspecting apparatus 100 shown in FIG. 10.

FIGS. 11A and 11B are top views showing movement trajectory of X-ray detector 23 and the scanning X-ray source, in the configuration of X-ray inspecting apparatus 100 shown in FIG. 10.

Operation Example 1 of FIG. 11A shows the configuration of FIG. 10 viewed from above, and represents movement of image pick-up position by XYθ operations. Operation Example 1 assumes image pick-up of 16 X-ray fluoroscopic images from equal angles. Operation Example 1 is suitable for the analytical method represented by Feldkamp. The reason is as follows. Generally, in the analytical method, the projection data is filtered. The desirable direction of filtering is vertical to the direction of X-ray transmission. Therefore, when the analytical method is used, it is desirable to have the X-ray detector positioned vertical to the X-ray transmission path, or to have the image picked up with the X-ray detector directed to the field of view.

Operation Example 2 of FIG. 11B shows the movement of image pick-up position of XY operation, which is suitable for the reconstruction method such as the iterative method or tomosynthesis. The reason for this is because, by the iterative method or tomosynthesis, reconstruction is possible regardless of the direction of the X-ray detector. In such an operation, it is unnecessary to rotate the X-ray detector. Therefore, the X-ray detector driving mechanism can further be simplified, and the speed of operation and maintainability of the mechanism for X-ray detector driving unit 22 can be improved.

Operation examples shown in FIGS. 11A and 11B (movement trajectory) will be described in greater detail in the following.

The range in which X-ray detector 23.1 can operate independently and the range in which X-ray detector 23.2 can operate independently are separate.

Positions A1 and B1 in FIGS. 11A and 11B represent initial positions of X-ray detectors 23.1 and 23.2, respectively. Positions A1 to A8 and positions B1 to B8 represent positions of X-ray detectors 23.1 and 23.2 at which fluoroscopic images necessary for image reconstruction are picked up, respectively.

In the operation examples shown in FIGS. 11A and 11B, X-ray detectors 23.1 and 23.2 move by a constant distance with the origin of imaging system being the center. Therefore, when the imaging system is viewed from above, each has semi-circular trajectory.

Here, positions a1, a2, a3, b1 and b2 are focal positions on the X-ray target, and positioned on lines connecting the field of view and X-ray detector positions A1, A2, A3, B1 and B2, respectively.

It is assumed that when image pick-up starts, X-ray detectors 23.1 and 23.2 are positioned stationary at A1 and B1, respectively.

i) From X-ray focal point position a1, X-ray is generated and an image is picked-up by X-ray detector 23.1 (position A1).

ii) Next, from X-ray focal point position b1, X-ray is generated and image pick-up starts by X-ray detector 23.2 (position B1). During image pick-up at position B1, X-ray detector 23.1 starts moving to a predetermined position A2.

iii) When image pick-up by X-ray detector 23.2 (position B1) and movement of X-ray detector 23.1 are finished, X-ray focal point position is immediately moved to position A2, and image pick-up is done by X-ray detector 23.1 (position A2). During the image pick-up, X-ray detector 23.2 moves to a predetermined position B2.

By repeating the above-described operations, it is possible to obtain the necessary number of images for image reconstruction, while the rest time of X-ray source derived from the time of movement of X-ray detectors is reduced.

Figure 12:
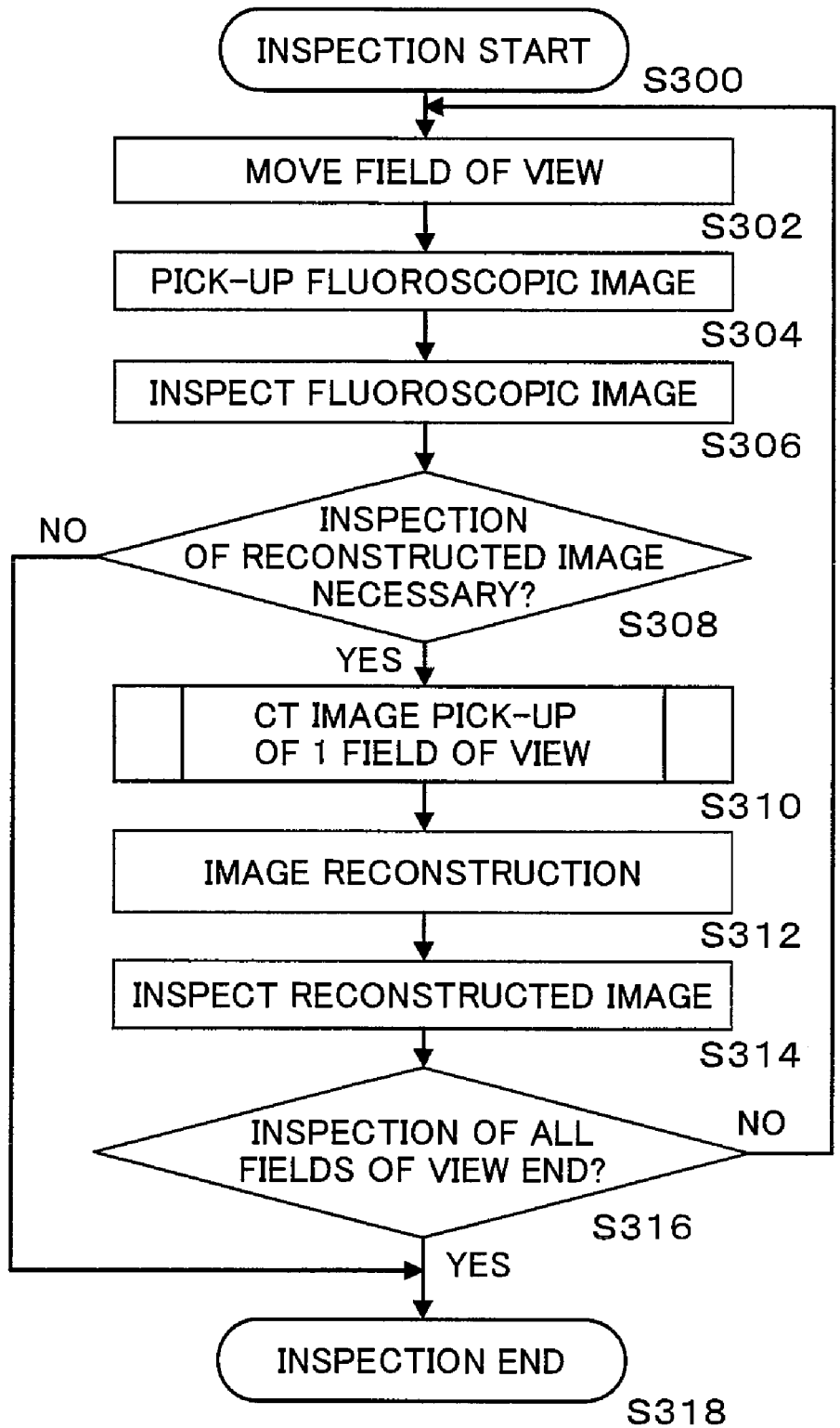
FIG. 12 is a flowchart of an overall inspection for reconstructed image inspection by X-ray inspecting apparatus 100 in accordance with Embodiment 1.

FIG. 12 is a flowchart of an overall inspection for reconstructed image inspection by X-ray inspecting apparatus 100 in accordance with Embodiment 1.

Referring to FIG. 12, first, when the process starts (S300), in accordance with an instruction from inspection object position control unit 80 of computing unit 70, the inspection object position control mechanism moves the position of inspection (field of view) of the object of inspection to a position allowing image pick-up (S302). Specifically, in order to pick-up a fluoroscopic image, the stage having the object of inspection placed thereon and the X-ray detector are moved to the prescribed positions. Generally, for inspection, an optical camera (not shown) is provided for specifying the position of detection and, therefore, it is possible to determine the position based on the position of the optical camera. Alternatively, the position may be automatically determined based on the CAD data of the object of inspection, or the position may be determined based on the visual observation by the operator.

Then, the fluoroscopic image is picked up (S304), and acceptance/rejection determining unit 78 of computing unit 70 inspects the fluoroscopic image and determines whether the field of view (the scope picked up in the fluoroscopic image) of the object of inspection is acceptable or not from the acquired fluoroscopic image (S306). Various methods have been proposed for the determination of acceptance/rejection, and since these methods are well known, detailed description thereof will not be given here. By way of example, in the most basic inspection, the fluoroscopic image is binarized using a constant value, compared with design information such as the CAD data, and based on the area, determination is made as to whether or not a component exists at a prescribed position of the fluoroscopic image.

Thereafter, computing unit 70 determines whether or not inspection by a reconstructed image is necessary (S308). A reference for determination may be set in advance based on design information such as the CAD data, or it may be determined based on the result of acceptance/rejection determination of fluoroscopic image. By way of example, in inspection of mounting boards, when components are mounted only on one side, it is possible to determine acceptance/rejection from the fluoroscopic image and, therefore, the acceptance/rejection determination using the reconstructed image may not be necessary.

If the inspection by the reconstructed image is unnecessary, computing unit 70 ends the inspection (S318).

If the inspection by the reconstructed image is necessary, computing unit 70 causes CT image pick-up for one field of view (S310). In the CT image pick-up, images of the field of view in the object of inspection (reconstruction area or the area similar to the scope of fluoroscopic image pick-up described above) are picked-up from a plurality of directions. Details of the CT image pick-up will be described later.

Next, 3D image reconstructing unit 76 of computing unit 70 generates a reconstructed image from the images picked-up from a plurality of directions (S312). Various methods for 3D reconstruction have been proposed and, by way of example, the Feldkamp method described above may be adopted.

Thereafter, acceptance/rejection determining unit 78 of computing unit 70 determines acceptance/rejection based on the reconstructed image (S314). As the method for determining acceptance/rejection, a method directly using the three-dimensional data, a method using two-dimensional data (tomographic image), or a method using one-dimensional data (profile) may be possible. These methods for determining acceptance/rejection are well known, and the method for determining acceptance/rejection suitable for the item to be inspected may be used. Therefore, detailed description will not be repeated here. In the following, an example of acceptance/rejection determination will be described. First, the three-dimensional reconstructed image is binarized using a constant value. Based on design information such as the CAD data, a position where a component exists (for example, a solder ball of BGA) in the reconstructed image is specified. From the binarized image, the volume of pixels neighboring the position of the component is calculated, and it is possible to determine whether the component is present or not.

Further, computing unit 70 determines whether or not inspection of all fields of view is completed (S316). If the inspection is not yet completed, the process returns to step S102. If the inspection is completed for all fields of view, computing unit 70 ends the inspection (S318).

Though the inspection is done using the fluoroscopic image and reconstructed image in the example of FIG. 12, it is also possible to perform the inspection using only the reconstructed image, not using the fluoroscopic image. Generally, however, acceptance/rejection determination based on fluoroscopic image is done before inspection by reconstructed image, to make shorter the overall inspection time, since the reconstruction process takes relatively long time.

Figure 13:
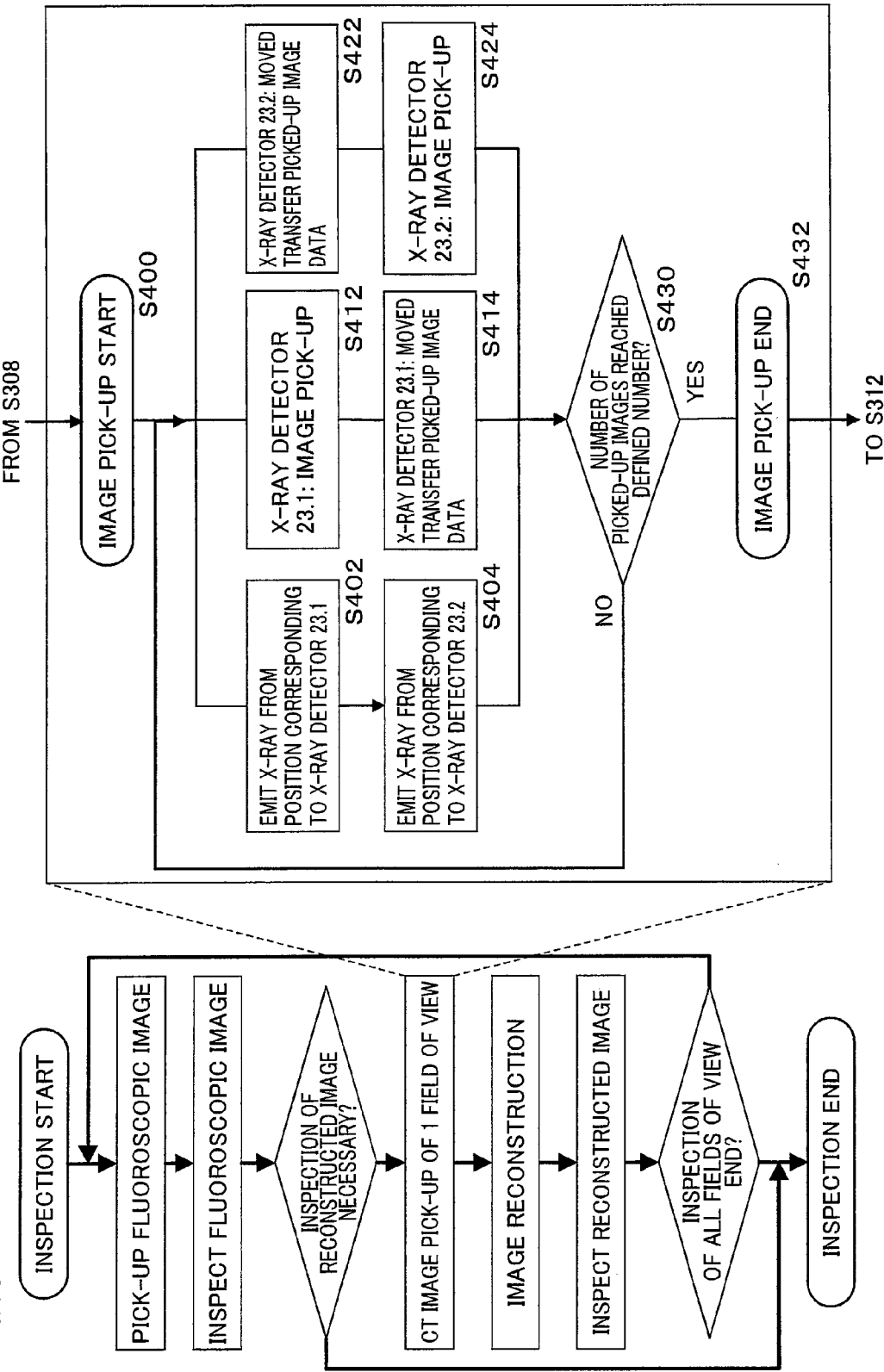
FIG. 13 is a flowchart of CT image pick-up of one field of view at step S301 shown in FIG. 12.

FIG. 13 is a flowchart of CT image pick-up of one field of view at step S301 shown in FIG. 12.

Figure 14:
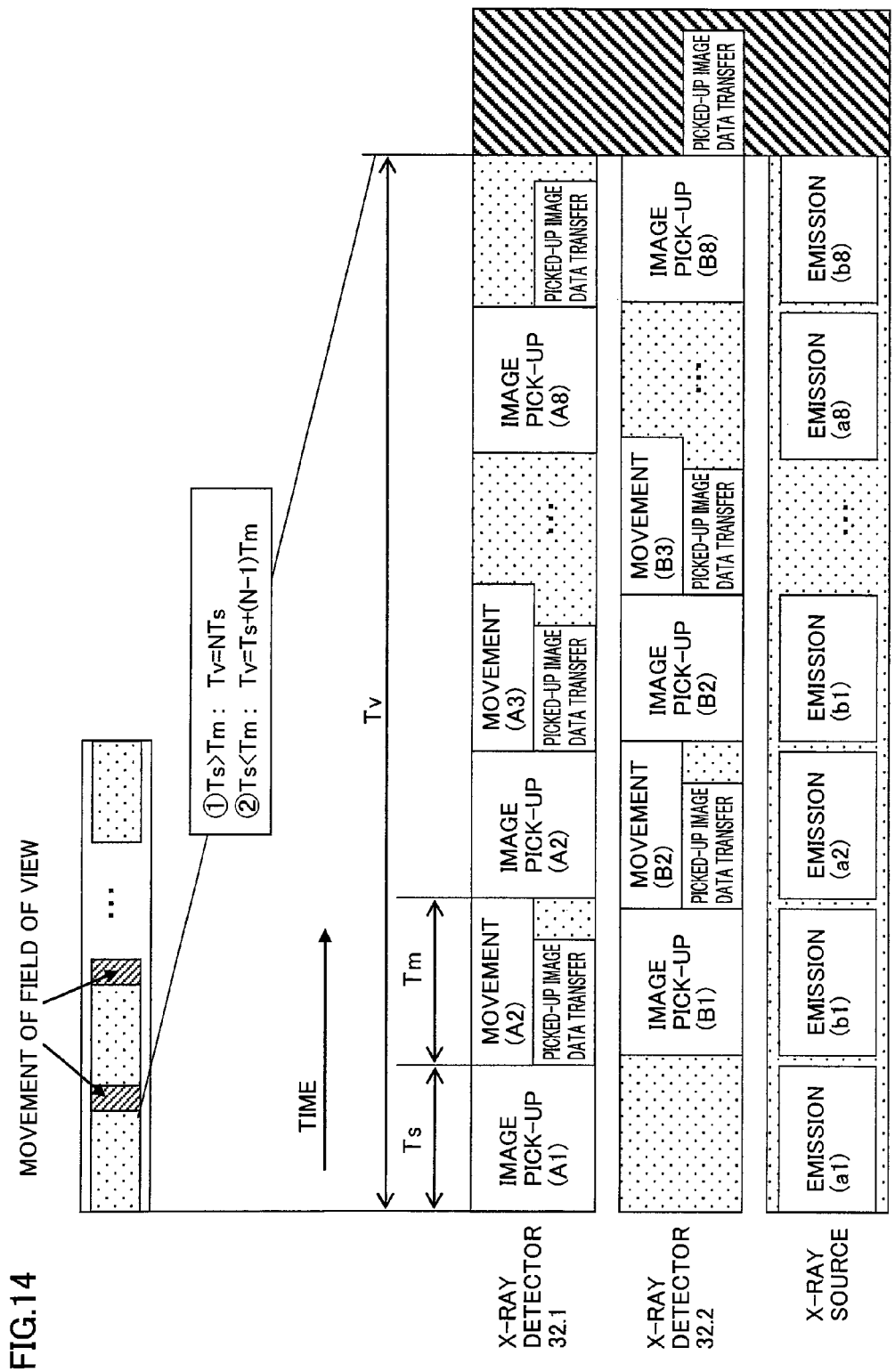
FIG. 14 is a timing chart representing operations of the X-ray detectors and the X-ray focal point position with time of inspection, in the inspection flow shown in FIG. 13.

FIG. 14 is a timing chart representing operations of the X-ray detectors and the X-ray focal point position with time of inspection, in the inspection flow shown in FIG. 13.

In FIG. 13, of three branches of the flowchart, the left part represents the operation of X-ray source, the central part represents the operation of X-ray detector 23.1, and the right part represents the operation of X-ray detector 23.2, and that the process steps are aligned in the lateral direction means the process steps take place simultaneously.

Referring to FIGS. 13 and 14, when the CT image pick-up process for one field of view starts (S400), computing unit 70 moves the object of inspection so that the field of view to be inspected is moved to an appropriate position. Then, computing unit 70 also moves X-ray detector 23 to the initial position. The position of X-ray detector 23 and the position of object of inspection may be set by using an encoder provided in X-ray detector driving unit 22 or the inspection object position driving mechanism (for example, the X-Y stage), or may be set using a general detector (such as a laser displacement gauge).

Thereafter, computing unit 70 moves the X-ray focal point position to a position corresponding to X-ray detector 23.1, emits X-ray (S402), and picks up an image by X-ray detector 23.1 (S412). Setting of the X-ray focal point position may be done in the above-described manner. The time of image pick-up (detector exposure time) may be set in advance, or a desired time may be set by the user based on the visual observation. In parallel therewith, computing unit 70 moves X-ray detector 23.2 to the next position of image pick-up, and transfers the image data acquired by X-ray detector 23.1 to memory 90, for example, for the reconstruction process by 3D image reconstructing unit 78 (S422).

Then, computing unit 70 moves the X-ray focal point position to a position corresponding to X-ray detector 23.2, emits X-ray (S404), and picks up an image by X-ray detector 23.2 (S424). In parallel therewith, computing unit 70 moves X-ray detector 23.1 to the next position of image pick-up, and transfers the image data acquired by X-ray detector 23.2 to memory 90 for the reconstruction process by 3D image reconstructing unit 78 (S414).

Thereafter, computing unit 70 determines whether the number of picked-up images has reached the defined number (S430). If the number has not yet reached the defined number for image reconstruction, computing unit 70 returns the process to steps S402, 412 and 422. If the number has reached the defined number, computing unit 70 ends the CT image pick-up for one field of view (S432), and the process proceeds to S312.

Though the determination as to whether the defined number has been reached is made after data transfer in the flowchart, it is preferred that the determination of picked up image number is made simultaneously with the data transfer. The reason for this is that data transfer takes time of about 200 ms, for example, and therefore, movement to the next position of image pick-up is delayed. This leads to generation of delay at every image pick-up operation. In order to reduce the delay time and to speed-up the operations, it is preferable to make determination related to the defined number and to move the object of inspection and X-ray detector simultaneously with the data transfer.

When the image pick-up method in accordance with Embodiment 1 is used as shown in FIG. 14, the time for image pick-up of one field of view can be represented by Equations (15) and (16) below.

$$\text{When } Ts>Tm: Tv=NTs \quad (15)$$

$$\text{When } Ts<Tm: Tv=Ts+(N-1)Tm \quad (16)$$

The signs represent as follows.

N: the number of picked-up images (integer multiple of the number of X-ray detectors)

Tv: time necessary for picking-up one field of view

Tm: time for moving the moving mechanism (stage, X-ray detector)

Ts: time for image pick-up (exposure time of X-ray detector).

Though the number N of picked-up images is set to the integer multiple of the number of X-ray detectors for simplicity of description, it is not necessarily limited to the integer multiple.

FIG. 14 shows an example in which Ts<Tm.

Assuming that the number of fluoroscopic images to be picked up necessary for reconstruction of the image is 16, and when the image pick-up method in accordance with Embodiment 1 is used, the time necessary for acquiring the necessary number of images=16 for reconstruction is 16Ts if Ts>Tm, and it is Ts+15Tm if Ts<Tm. In either case, the time for image pick-up can be reduced from (16Ts+15Tm) required by the method using one detector described with reference to FIG. 9.

If the intensity of X-ray source is enhanced and the sensitivity of X-ray detector is improved, the exposure time of X-ray detector necessary for image pick-up becomes shorter. Therefore, if an X-ray detector is to be moved to a prescribed position of image pick-up while another X-ray detector is picking an image, a high-speed mechanism becomes necessary. It may be possible that even when image pick-up by an X-ray detector is finished, movement of another X-ray detector is not yet finished.

In any case, the overall process time can be reduced as the process of image pick-up by one X-ray detector and the process of moving another X-ray detector to a prescribed image pick-up position or the process of transferring the picked-up image data of the moved X-ray detector are carried out in parallel. Further, since such parallel processing is repeated for the overall process for one field of view, the process time for one field of view can be reduced.

Modification of Embodiment 1

Figure 15:
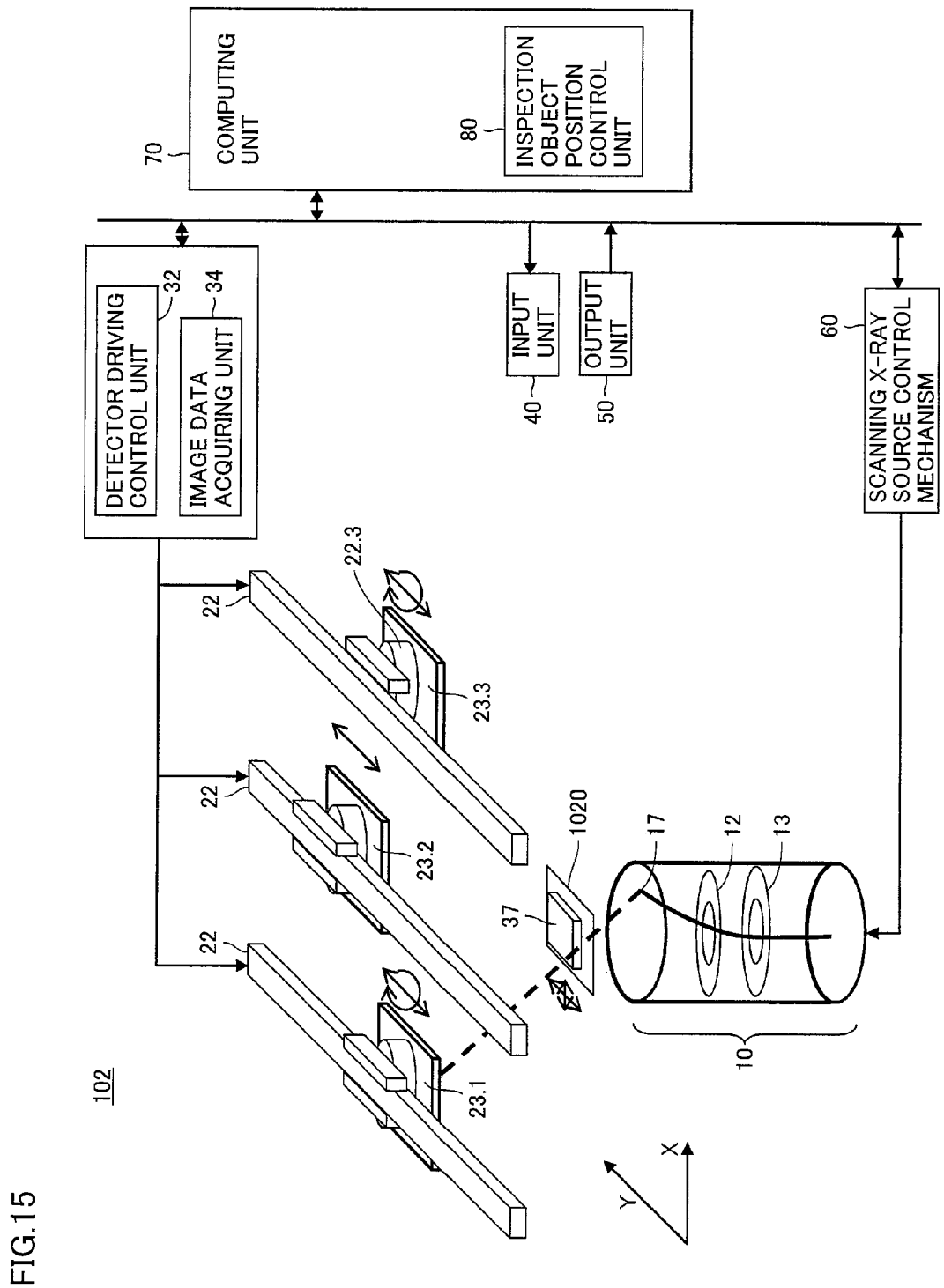
FIG. 15 illustrates a configuration of an X-ray inspecting apparatus 102 in accordance with a modification of Embodiment 1.

FIG. 15 illustrates a configuration of an X-ray inspecting apparatus 102 in accordance with a modification of Embodiment 1. In X-ray inspecting apparatus 102, linear type X-ray detectors and a scanning X-ray source as X-ray source 10 are used.

Specifically, in X-ray inspecting apparatus 102, three X-ray detectors 23.1, 23.2 and 23.3 are each capable of Y-movement and θ rotation, independently from each other. FIG. 15 shows an operation mechanism of X-ray detector driving unit 22 in which X-ray detector supporting unit 22.3 is rotatable and movable on a rail in Y direction. Any mechanism other than that shown in FIG. 15 having the same function may be used without any problem. Further, the rotating mechanism is not always necessary, as will be described later.

The scanning X-ray source as X-ray source 10 is capable of moving the X-ray focal point position at high speed to an arbitrary position on the X-ray target.

Further, the same portions as those of FIGS. 1 and 10 are denoted by the same reference characters. In FIG. 15 also, portions necessary for the description are extracted from portions directly related to the control of X-ray focal point position, the control of X-ray detector position and the control of the position of object of inspection.

Though three X-ray detectors movable independently from each other are used in the example of FIG. 15, the number of X-ray detectors is at least two. If the number of X-ray detectors is an odd number, the following advantageous effects can be attained. Therefore, it is desirable to provide three or more odd number of detectors. Specifically, by providing odd number of X-ray detectors, it becomes possible to pick-up an image of the object of inspection from directly above, by the X-ray detector moving on the central rail. This is suitable for picking-up the fluoroscopic image in the operation in accordance with the flowchart described, for example, with respect to FIG. 12. From the viewpoint of minimizing the number of detectors and the number of moving mechanisms considering cost, three is the desirable number.

In the configuration shown in FIG. 15, X-ray detector driving unit 22 includes a detector supporting unit 22.3 rotatable about an axis of rotation and allowing movement of X-ray detector in Y direction on the rail, and moves and rotates X-ray detector 23.

As in the configuration shown in FIG. 10, the field of view of object of inspection can be moved in the X-Y direction independently from X-ray detectors 23.1, 23.2 and 23.3 described above, by inspection object position driving mechanism 1020 (X-Y stage or the like on which the object of inspection is placed) controlled by inspection object control unit 80 in computing unit 70. Further, as described above, the scanning X-ray source of X-ray source 10 is capable of moving X-ray focal point position 17 to an arbitrary position on the X-ray target at high speed.

Computing unit 70 transmits instructions to detector driving control unit 32, image data acquiring unit (X-ray detector controller) 34 and scanning X-ray source control mechanism 60, and executes a program represented by the flowchart for the inspection process as will be described later. Further, it controls operations of the inspecting apparatus in accordance with an input from input unit 40, and it can output status of each portion or results of inspection from output unit 50.

Inspection object position control mechanism 1020 includes an actuator and a mechanism for fixing the object of inspection, and moves the object of inspection in accordance with an instruction from inspection object position control unit 80.

X-ray detector driving unit 22 moves X-ray detector 23 to a designated position in accordance with an instruction from computing unit 70 through detector driving control unit 32. Further, detector driving control unit 32 transmits position information of X-ray detector 23 at the time point to computing unit 70.

Computing unit 70 acquires X-ray fluoroscopic image and transfers picked-up image data at a timing designated by an instruction through detector driving control unit 32.

X-ray source 10 generates an electron beam in accordance with an instruction from computing unit 70 through scanning X-ray source control mechanism 60, converges the electron beams on a designated position on the target by electron beam converging coil 13 and deflection yoke 12, and moves X-ray focal point 17 at high speed.

Figure 16:
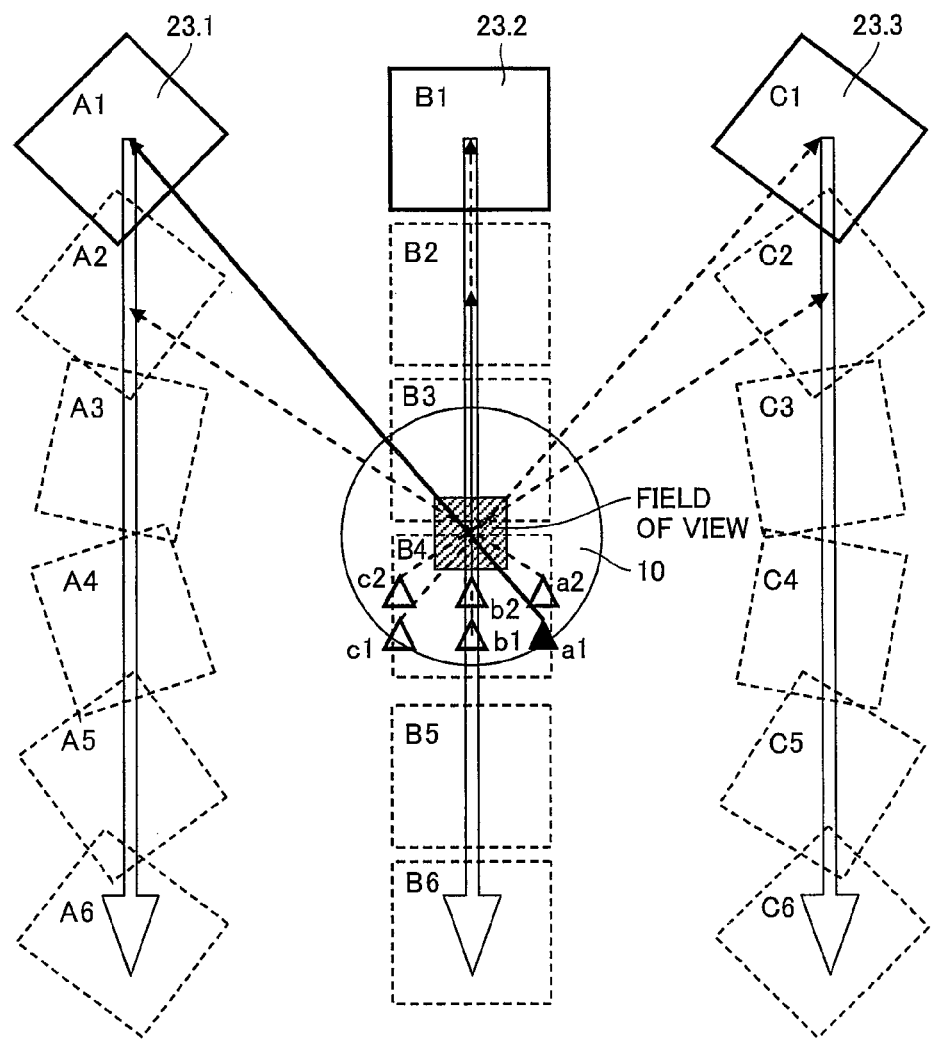
FIG. 16 is a top view showing movement trajectory of X-ray detector 23 and the scanning X-ray source, in the configuration of X-ray inspecting apparatus 102 shown in FIG. 15.

FIG. 16 is a top view showing movement trajectory of X-ray detector 23 and the scanning X-ray source, in the configuration of X-ray inspecting apparatus 102 shown in FIG. 15.

Operation Example 1 of FIG. 16 shows the configuration of FIG. 15 viewed from above, assuming image pick-up of 18 X-ray fluoroscopic images picked up from different angles.

As described above, in FIG. 16, X-ray detectors 23.1, 23.2 and 23.3 each have a mechanism allowing linear movement on a rail. Further, X-ray detectors 23.1, 23.2 and 23.3 each have a rotation mechanism allowing rotation about the center of the X-ray detector.

X-ray source 10 is a scanning X-ray source. Further, the position of image pick-up by X-ray detector 23 may not be limited to the arrangement of FIG. 16, and may be set at angles of equal interval. Further, the number of images to be picked-up is not limited to 18, and any number that allows inspection may be designated. The number of images to be picked-up may be designated by calculation based on design information such as the CAD data, or may be determined by the operator based on the visual observation.

Referring to FIG. 16, positions A1 to A6, B1 to B6 and C1 to C6 represent positions of X-ray detectors 23.1, 23.2 and 23.3 that acquire fluoroscopic images necessary for image reconstruction, respectively. The numbers 1 to 6 appended to the positions represent the order of image pick-up, and image is picked up first at position A1 and at A6 at the end.

Further, positions a1, a2, b1, b2, c1 and c2 represent focal point positions on the X-ray target, which correspond to the X-ray detector positions A1, A2, B1, B2, C1 and C2, respectively.

Operation Example 1 shown in FIG. 16 is suitable for applying the analytical method represented by Feldkamp method. As in the case of FIG. 11A, generally, in the analytical method, the projection data is filtered. The desirable direction of filtering is vertical to the direction of X-ray transmission. Therefore, when the analytical method is used, it is desirable to have the X-ray detector positioned vertical to the X-ray transmission path, or to have the image picked up with the X-ray detector directed to the field of view.

Figure 17:
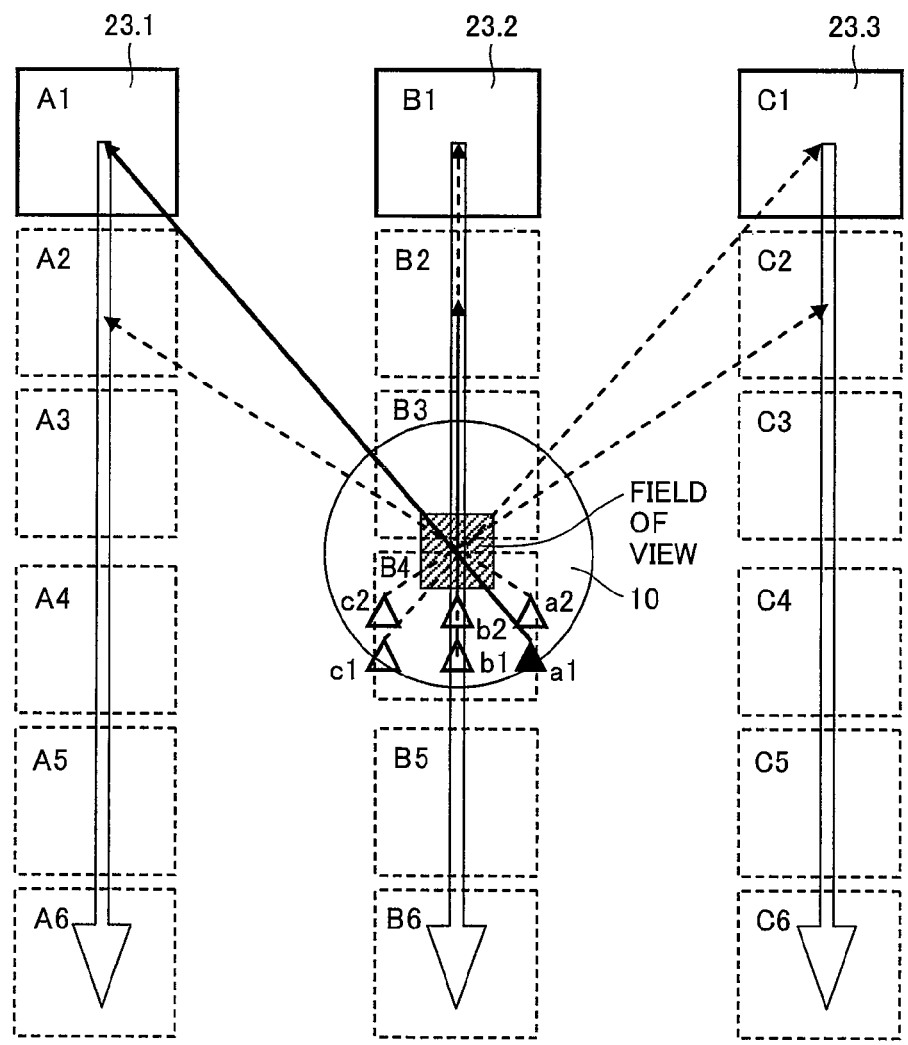
FIG. 17 is a top view showing another movement trajectory of X-ray detector 23 and the scanning X-ray source, in the configuration of X-ray inspecting apparatus 102 shown in FIG. 15.

FIG. 17 is a top view showing another movement trajectory of X-ray detector 23 and the scanning X-ray source, in the configuration of X-ray inspecting apparatus 102 shown in FIG. 15.

In Operation Example 2 shown in FIG. 17, X-ray detector 23 does not rotate and moves in translational manner in the X-Y plane. Operation Example 2 as such is suitable for applying the reconstruction method such as an iterative method or tomosynthesis. The reason for this is that by the iterative method or tomosynthesis, the reconstruction is possible regardless of the direction of X-ray detector.

In such an operation, it is unnecessary to rotate the X-ray detector. Therefore, the X-ray detector driving mechanism can further be simplified, and the speed of operation and maintainability can be improved.

Figure 18:
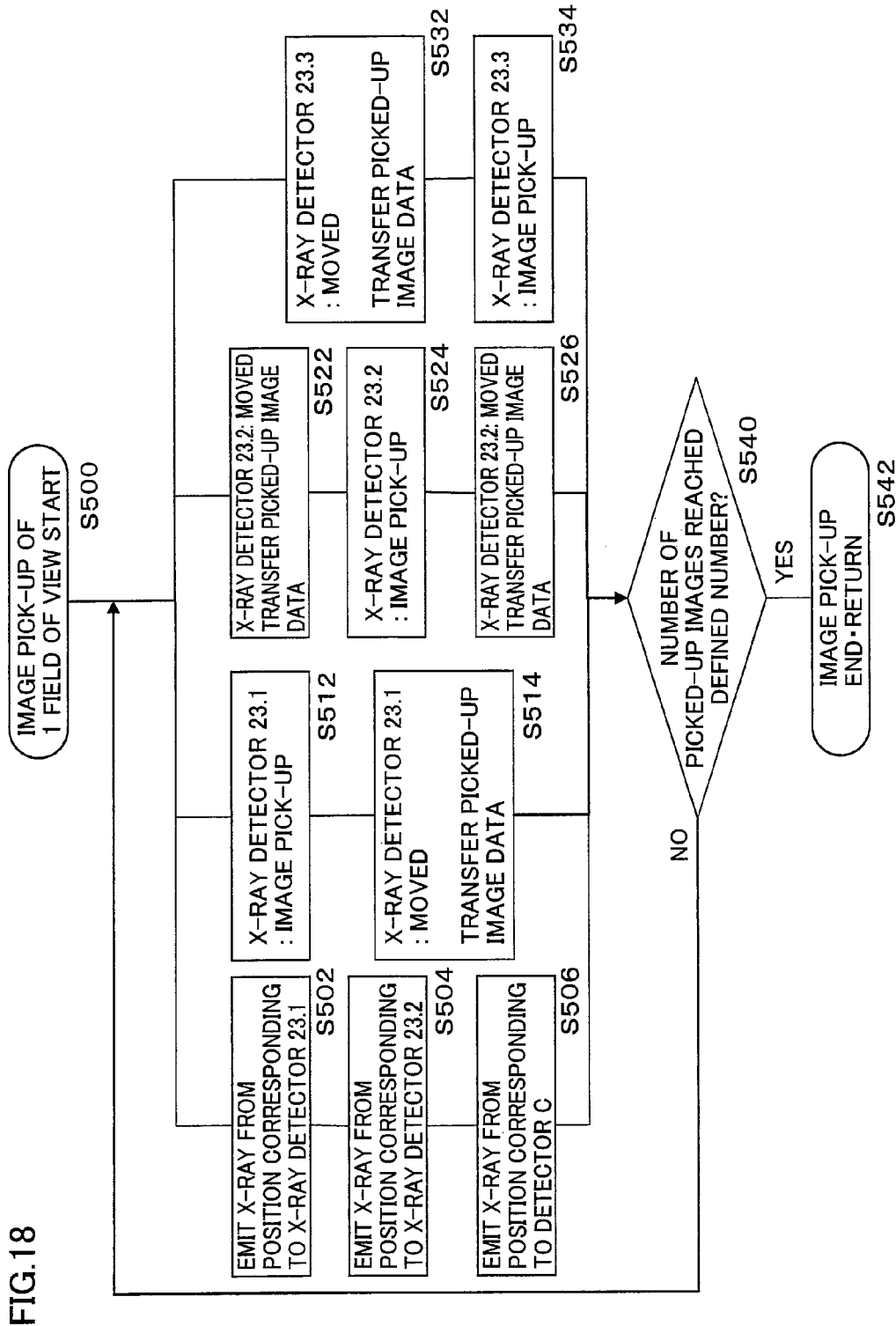
FIG. 18 is a flowchart of inspection when X-ray detector 23 is moved for inspection as in the example of FIG. 16 or 17.

FIG. 18 is a flowchart of inspection when X-ray detector 23 is moved for inspection as in the example of FIG. 16 or 17.

The flow of the overall inspection is similar to that shown in FIG. 12. FIG. 18 represents the portion of CT image pick-up for one field of view of step S310 shown in FIG. 12.

FIG. 18 shows a flowchart of CT image pick-up for one field of view of step S310 described with reference to FIG. 12. In FIG. 18, of four branches of the flowchart, the leftmost part represents the operation of X-ray source, the center-left part represents the operation of X-ray detector 23.1, the center-right part represents the operation of X-ray detector 23.2, and the rightmost part represents the operation of X-ray detector 23.3, and that the process steps are aligned in the lateral direction means the process steps take place simultaneously.

Figure 19:
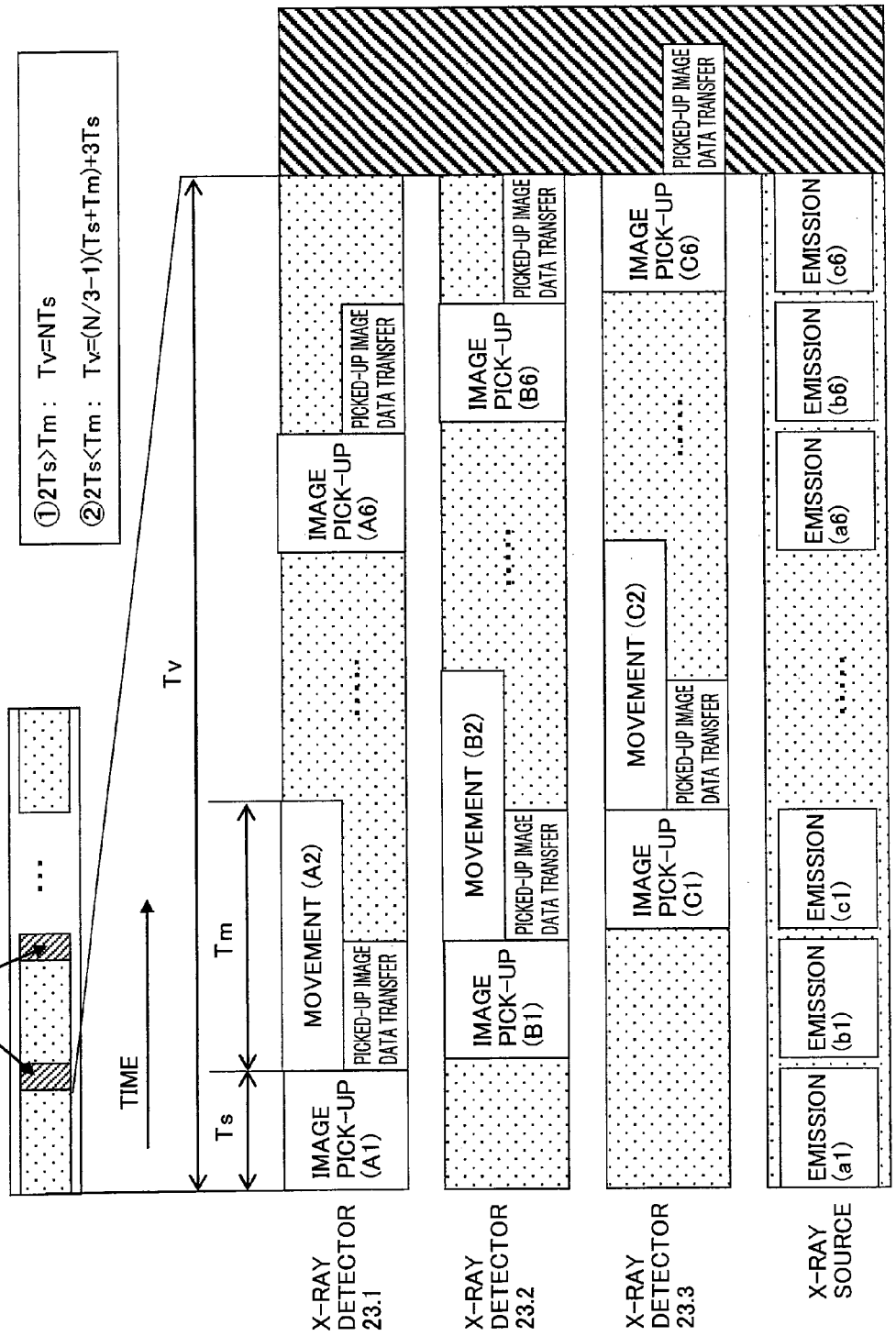
FIG. 19 is a timing chart representing operations of the X-ray detectors and the X-ray focal point position with time of inspection, in the inspection flow shown in FIG. 18.

FIG. 19 is a timing chart representing operations of the X-ray detectors and the X-ray focal point position with time of inspection, in the inspection flow shown in FIG. 18.

Referring to FIGS. 18 and 19, when the CT image pick-up process for one field of view starts (S500), computing unit 70 moves the object of inspection so that the field of view to be inspected is moved to an appropriate position. Then, computing unit 70 also moves X-ray detector 23 to the initial position. The position of X-ray detector 23 and the position of object of inspection may be set by using an encoder provided in X-ray detector driving unit 22 or inspection object position driving mechanism (for example, X-Y stage), or may be set using a general detector (such as a laser displacement gauge).

Therefore, in the timing chart of FIG. 19, it is assumed that operation starts with X-ray detectors 23.1, 23.2 and 23.3 positioned at initial positions A1, B1 and C1, respectively.

Thereafter, computing unit 70 moves the X-ray focal point position to a position corresponding to X-ray detector 23.1, emits X-ray (S502), and picks up an image by X-ray detector 23.1 (S512). Setting of the X-ray focal point position may be done in the above-described manner. The time of image pick-up (detector exposure time) is set in the similar manner as in Embodiment 1.

Thereafter, computing unit 70 moves the X-ray focal point to the position of three-times-later image pick-up by X-ray detector 23.1, and transfers the image data acquired by X-ray detector 23.1 to memory 90, for example, for the reconstruction process by 3D image reconstructing unit 78 (S514).

In parallel therewith, computing unit 70 moves the X-ray focal point to a position corresponding to X-ray detector 23.2, emits X-ray (S504), and picks up an image by X-ray detector 23.2 (S524). Next, computing unit 70 moves the X-ray focal point to the position of three-times-later image pick-up by X-ray detector 23.2, and transfers the image data acquired by X-ray detector 23.2 to memory 90, for example, for the reconstruction process by 3D image reconstructing unit 78 (S526).

In parallel therewith, computing unit 70 moves the X-ray focal point to a position corresponding to X-ray detector 23.3, emits X-ray (S506), and picks up an image by X-ray detector 23.3 (S534).

Computing unit 70 determines whether the number of picked-up images has reached the defined number (S540). If the number has not yet reached the defined number, computing unit 70 returns the process to step S532.

Next, computing unit 70 moves the X-ray focal point to the position of three-times-later image pick-up by X-ray detector 23.3, and transfers the image data acquired by X-ray detector 23.3 to memory 90, for example, for the reconstruction process by 3D image reconstructing unit 78 (S532).

Thereafter, the process steps are repeated until image pick-up of the defined number is completed.

Finally, when the image pick-up by X-ray detector 23.3 ends, the image data acquired by X-ray detector 23.3 is transferred to memory 90 for the reconstruction process by 3D image reconstructing unit 78 (S514).

If the number has reached the defined number, computing unit 70 ends the CT image pick-up for one field of view (S542), and the process proceeds to S312.

Though the determination as to whether the defined number has been reached is shown as made after the data transfer in the flowchart of FIG. 18 for the convenience of description of the flow, actually, the determination of picked up image number is made simultaneous with the data transfer.

As shown in the timing chart of FIG. 19, when we represent the time of image pick-up and the time necessary for movement of detectors by Ts and Tm, respectively, the following relations hold.

When $2Ts \Rightarrow Tm: Tv = NTs$

When $2Ts < Tm: Tv = (N/3-1)(Ts+Tm)+3Ts$.

The signs represent as follows.

N: the number of picked-up images (integer multiple of the number of X-ray detectors)

Tv: time necessary for picking-up one field of view

Tm: time for moving the moving mechanism (stage, X-ray detector)

Ts: time for image pick-up (exposure time of X-ray detector).

Though the number of picked-up images is set to the integer multiple of the number of X-ray detectors for simplicity of description, it is not necessarily limited to the integer multiple.

Assume that the number of fluoroscopic images to be picked up necessary for reconstruction of the image is 18, and when the image pick-up method for X-ray inspecting apparatus 102 (in which three X-ray detectors are used one after another) is used, the time necessary for acquiring the necessary number of images, that is, 18, for reconstruction is 18Ts if 2Ts>Tm, and it is 8Ts+5Tm if 2Ts<Tm. In either case, the time for image pick-up can be reduced from (16Ts+15Tm) required by the method using one detector described with reference to FIG. 9. Further, the speed is higher than that of Tv=NTs+(N/S−1)Tm=18Ts+5Tm required when three X-detectors are used.

In the modification of Embodiment 1, as in Embodiment 1, in order to reduce the time of image pick-up, not the large and heavy X-ray source but the X-ray detectors and the object of inspection that can be moved relatively easily are moved. Further, movement of each component is linear, so that it can be attained by simple mechanism. Therefore, the distance of movement of the X-ray detector to the prescribed position can be made shorter and higher speed of movement can be attained. As a result, the time of mechanical movement is reduced, enabling high speed inspection.

Embodiment 2

In X-ray inspecting apparatus 102 in accordance with the modification of Embodiment 1, linear type X-ray detectors and scanning X-ray source as X-ray source 10 are provided.

In X-ray inspecting apparatus 104 in accordance with Embodiment 2, in place of the scanning X-ray source, a plurality of fixed focus X-ray sources are used as X-ray source 10.

Figure 20:
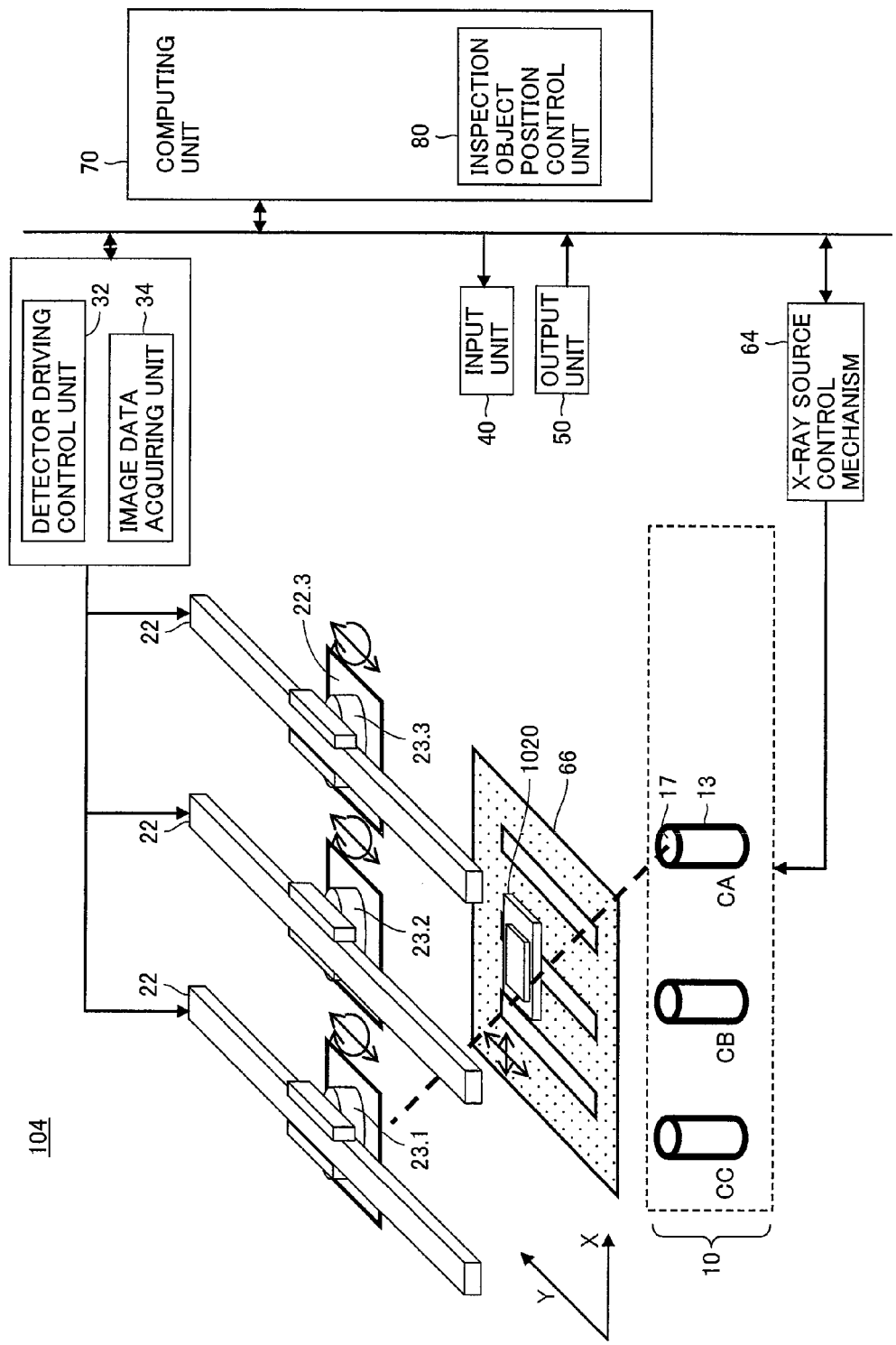
FIG. 20 illustrates a configuration of an X-ray inspecting apparatus 104 in accordance with Embodiment 2.

FIG. 20 illustrates a configuration of an X-ray inspecting apparatus 104 in accordance with Embodiment 2.

In X-ray inspecting apparatus 104, corresponding to three X-ray detectors 23.1 to 23.3 provided as X-ray detector 23, three fixed-focus X-ray sources are provided as X-ray source 10.

From these three fixed-focus X-ray sources, X-rays are emitted simultaneously to the same field of view of the object of inspection. Here, in order to prevent X-ray from an X-ray source directing the X-ray to be incident on one X-ray detector from entering other X-ray detector, a shield 66 is provided. In addition, for controlling the X-ray sources, an X-ray source control mechanism 64 is provided in place of scanning X-ray source control mechanism 60. Different from scanning X-ray source control mechanism 60, X-ray source control mechanism 64 does not perform deflection control of an electron beam but controls three X-ray sources simultaneously.

As in the case of X-ray inspecting apparatus shown in FIG. 15, five or more X-ray detectors in odd number may be provided. Specifically, by providing odd number of X-ray detectors, it becomes possible to pick-up an image of the object of inspection from directly above, by the X-ray detector moving on the central rail. This is suitable for picking-up the fluoroscopic image in the operation in accordance with the flowchart described, for example, with respect to FIG. 12.

The mechanism for moving X-ray detectors 23.1 to 23.3 is basically the same as that in X-ray inspecting apparatus 102 in accordance with the modification of Embodiment 1 described with reference to FIG. 15. It is noted, however, that in X-ray inspecting apparatus 104, the manner of movement of X-ray detectors 23.1 to 23.3 is different from that of X-ray inspecting apparatus 102 described with reference to FIG. 15.

However, as in X-ray inspecting apparatus 102 in accordance with the modification of Embodiment 1, also in X-ray inspecting apparatus 104 in accordance with Embodiment 2, movement of each component is linear, so that it can be attained by simple mechanism. Therefore, the distance of movement of the X-ray detector to the prescribed position can be made shorter and higher speed of movement can be attained. As a result, the time of mechanical movement is reduced, enabling high speed inspection.

Figure 21:
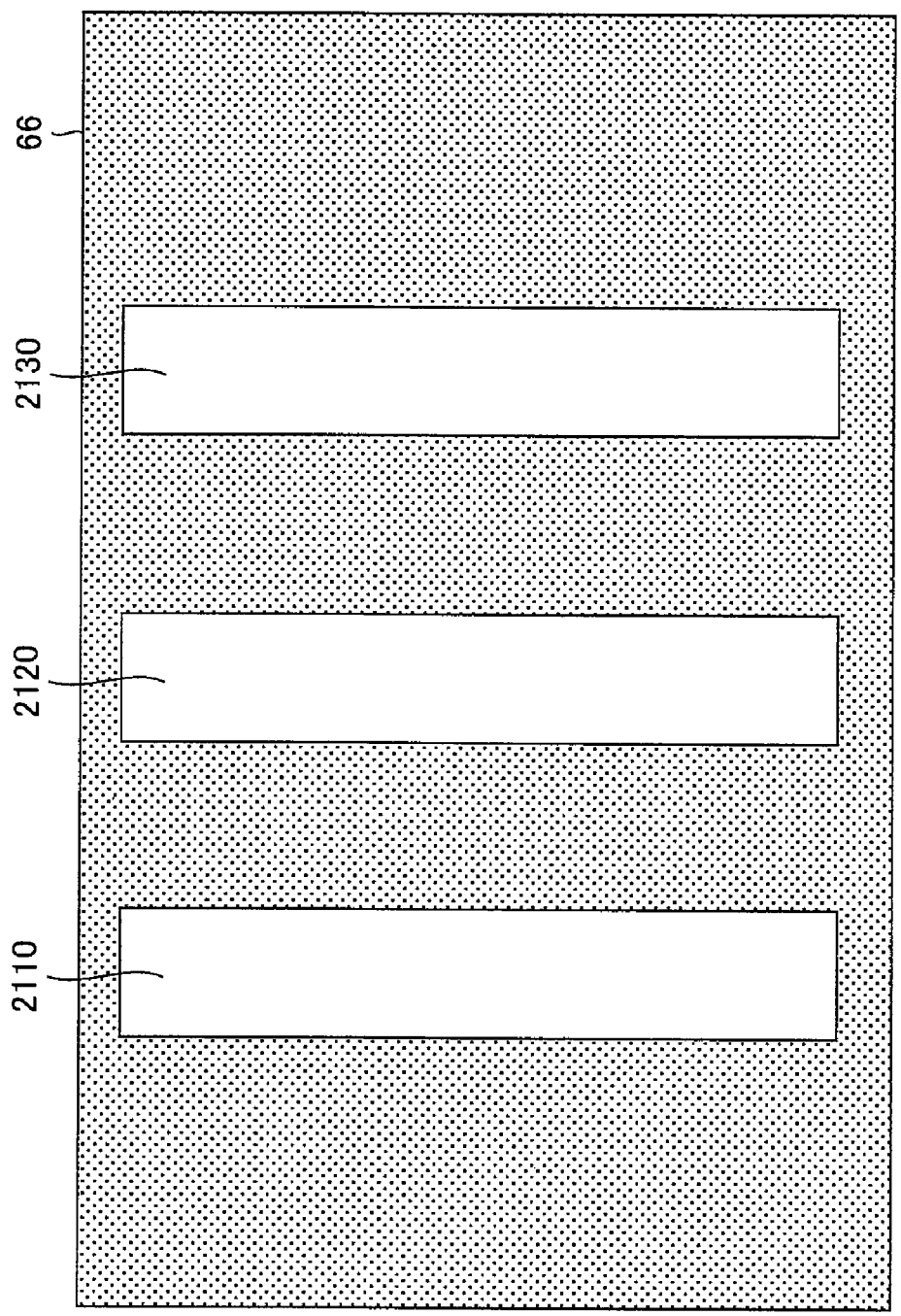
FIG. 21 is a top view of a shield 66.

FIG. 21 is a top view of shield 66. Corresponding to provision of three X-ray detectors 23, three openings 2110, 2120 and 2130 are formed at such positions that prevent, when three X-ray detectors operate simultaneously, X-ray from an X-ray source directing the X-ray to be incident on one X-ray detector from entering other X-ray detector.

Shield 66 is formed of such a material to have such a thickness that can sufficiently block X-ray, and preferably it is formed of lead. Since the X-ray detector moves linearly, each opening of the shield is formed to have a rectangular shape (or a slit). Further, the size of shield 66 is set such that X-ray from an X-ray source CA does not enter an X-ray detector CC. The size of the opening of shield 66 is set such that X-ray from X-ray source CA can sufficiently enter X-ray detector 23.1 but X-ray to X-ray detector 23.2 is blocked.

Figure 22:
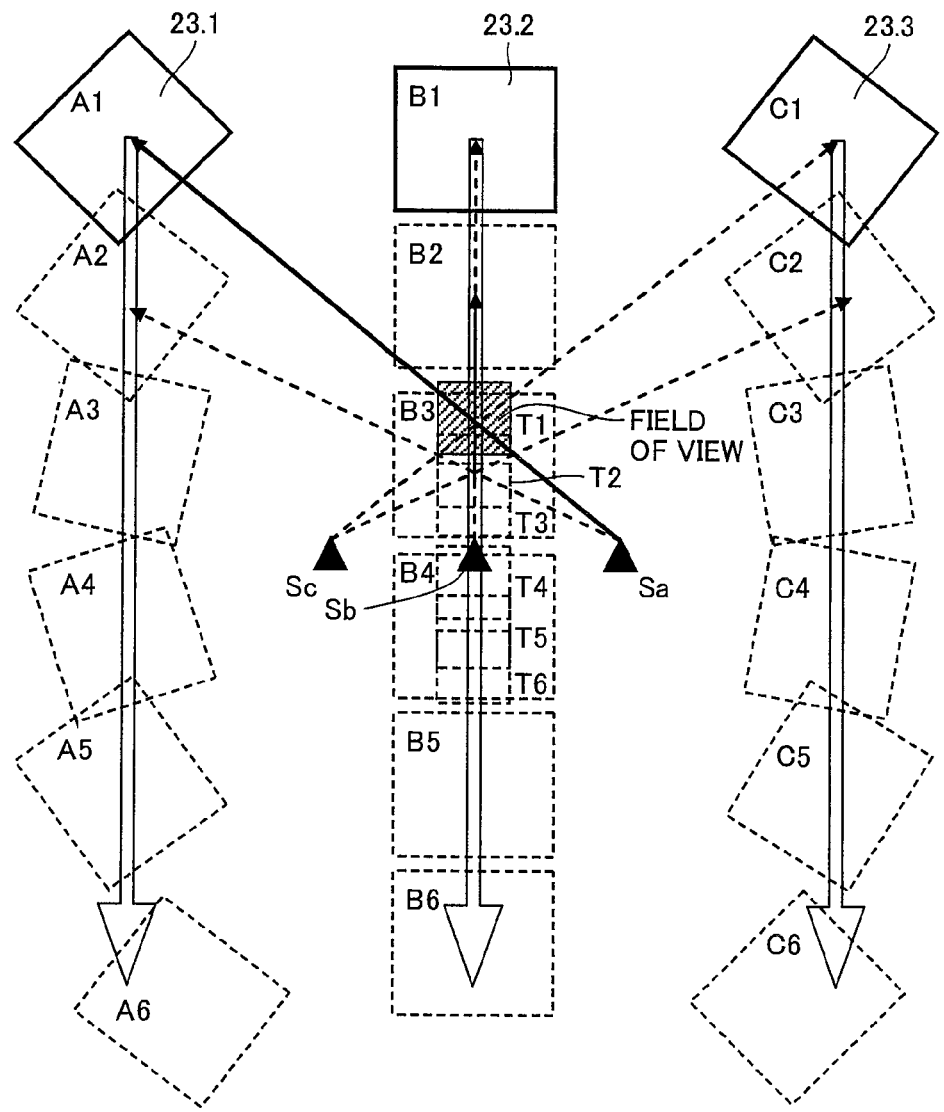
FIG. 22 is a top view showing movement trajectory of X-ray detector 23 and the fixed focus X-ray source, in the configuration of X-ray inspecting apparatus 104 shown in FIG. 20.

FIG. 22 is a top view showing movement trajectory of X-ray detector 23 and the fixed focus X-ray source, in the configuration of X-ray inspecting apparatus 104 shown in FIG. 20.

Operation Example 1 of FIG. 22 shows the configuration of FIG. 20 viewed from above, assuming image pick-up of 18 X-ray fluoroscopic images picked up from different angles.

As described above, in FIG. 22, X-ray detectors 23.1, 23.2 and 23.3 each have a mechanism allowing linear movement on a rail. Further, X-ray detectors 23.1, 23.2 and 23.3 each have a rotation mechanism allowing rotation about the center of the X-ray detector.

As described above, X-ray source 10 is not a scanning X-ray source, but an imaging system including three, fixed-focus X-ray sources.

Different from X-ray inspecting apparatus 102 shown in FIG. 15, X-ray detectors 23.1, 23.2 and 23.3 linearly move in an integrated manner.

With X-rays from three X-ray sources, images are picked up simultaneously by X-ray detectors 23.1, 23.2 and 23.3 and, thereafter, X-ray detectors 23.1, 23.2 and 23.3 move linearly together to the next position of image pick-up. Further, the object of inspection is moved from position T1 to T6 in synchronization with X-ray detectors 23.1, 23.2 and 23.3 such that the area of reconstruction is the same.

Further, the number of images to be picked-up is not limited to 18, and any number that allows inspection may be designated. The number of images to be picked-up may be designated by calculation based on the design information such as the CAD data, or may be determined by the operator based on the visual observation.

Referring to FIG. 22, positions A1 to A6, B1 to B6 and C1 to C6 represent positions of X-ray detectors 23.1, 23.2 and 23.3 that acquire fluoroscopic images necessary for image reconstruction, respectively. The numbers 1 to 6 appended to the positions represent the order of image pick-up, and image is picked up first at position A1 and at A6 at the end.

Further, positions Sa, Sb and Sc are focal point positions of X-ray sources CA, CB and CC, respectively.

Operation Example 1 of FIG. 22 is suitable for applying the analytical process represented by the Feldkamp method, from the same reason as described with respect to Embodiment 1.

Figure 23:
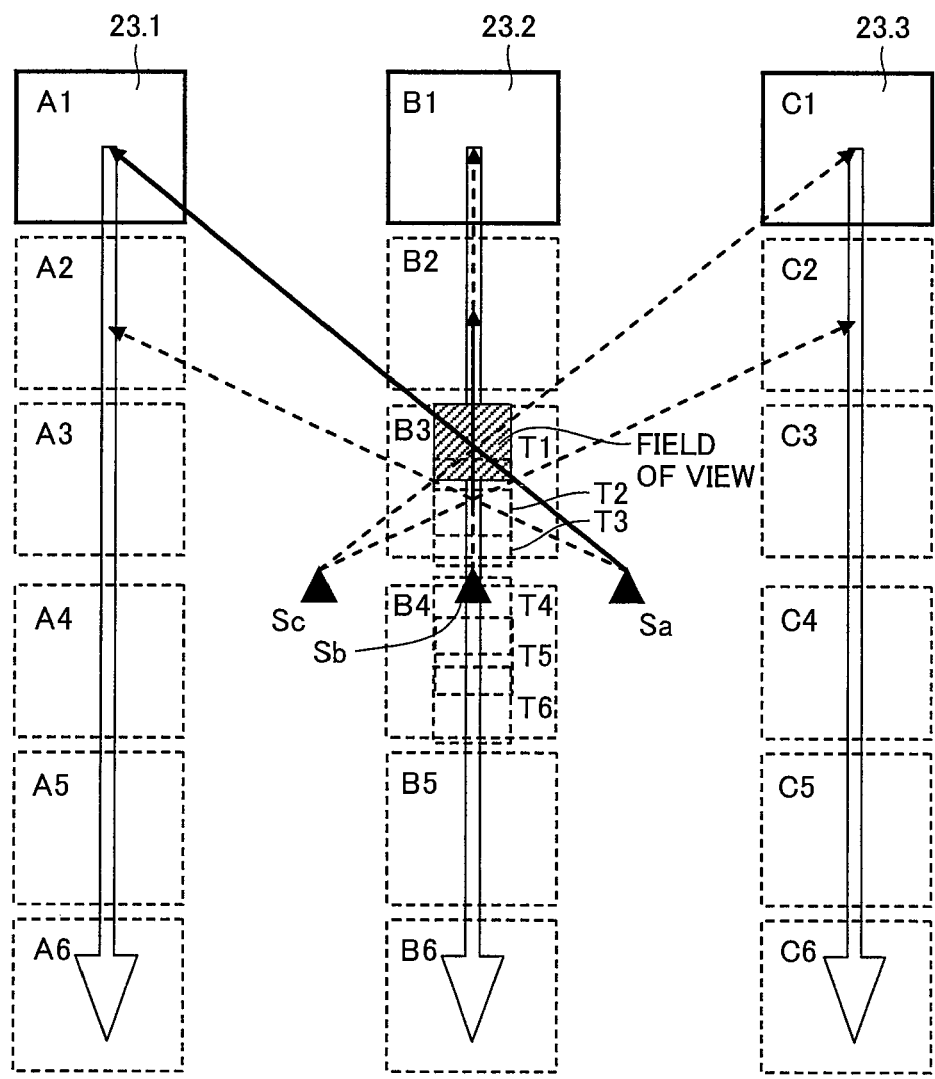
FIG. 23 is a top view showing another movement trajectory of X-ray detector 23 and the fixed focus X-ray source, in the configuration of X-ray inspecting apparatus 104 shown in FIG. 20.

FIG. 23 is a top view showing another movement trajectory of X-ray detector 23 and the fixed focus X-ray source, in the configuration of X-ray inspecting apparatus 104 shown in FIG. 20.

In Operation Example 2 shown in FIG. 23, X-ray detector 23 does not rotate and moves in translational manner in the X-Y plane. Operation Example 2 as such is suitable for applying the reconstruction method such as the iterative method or the tomosynthesis from the same reason as described with respect to Embodiment 1.

In such an operation, it is unnecessary to rotate the X-ray detector. Therefore, the X-ray detector driving mechanism can further be simplified, and the speed of operation and maintainability can be improved.

Here, the positional relation between the X-ray focal point position and the X-ray detector will be described.

Regarding the center of field of view to be reconstructed by CT as the origin, we represent the distance from the center of field of view to the X-ray focal point by Lf and the distance from the center of field of view to the center of X-ray detector by Ls. Then, the following relation holds.

$$Ls = -Lf \times (M-1)$$

That the sign is negative means the direction is opposite. Here, M represents magnification, and the magnification is given by as follows.

$$M=Hs/Ho.$$

Here, Hs represents height from the X-ray focal point to the X-ray detector, and Ho represents height from the X-ray focal point to the center of field of view. The relation itself holds similarly in other embodiments.

Figure 24:
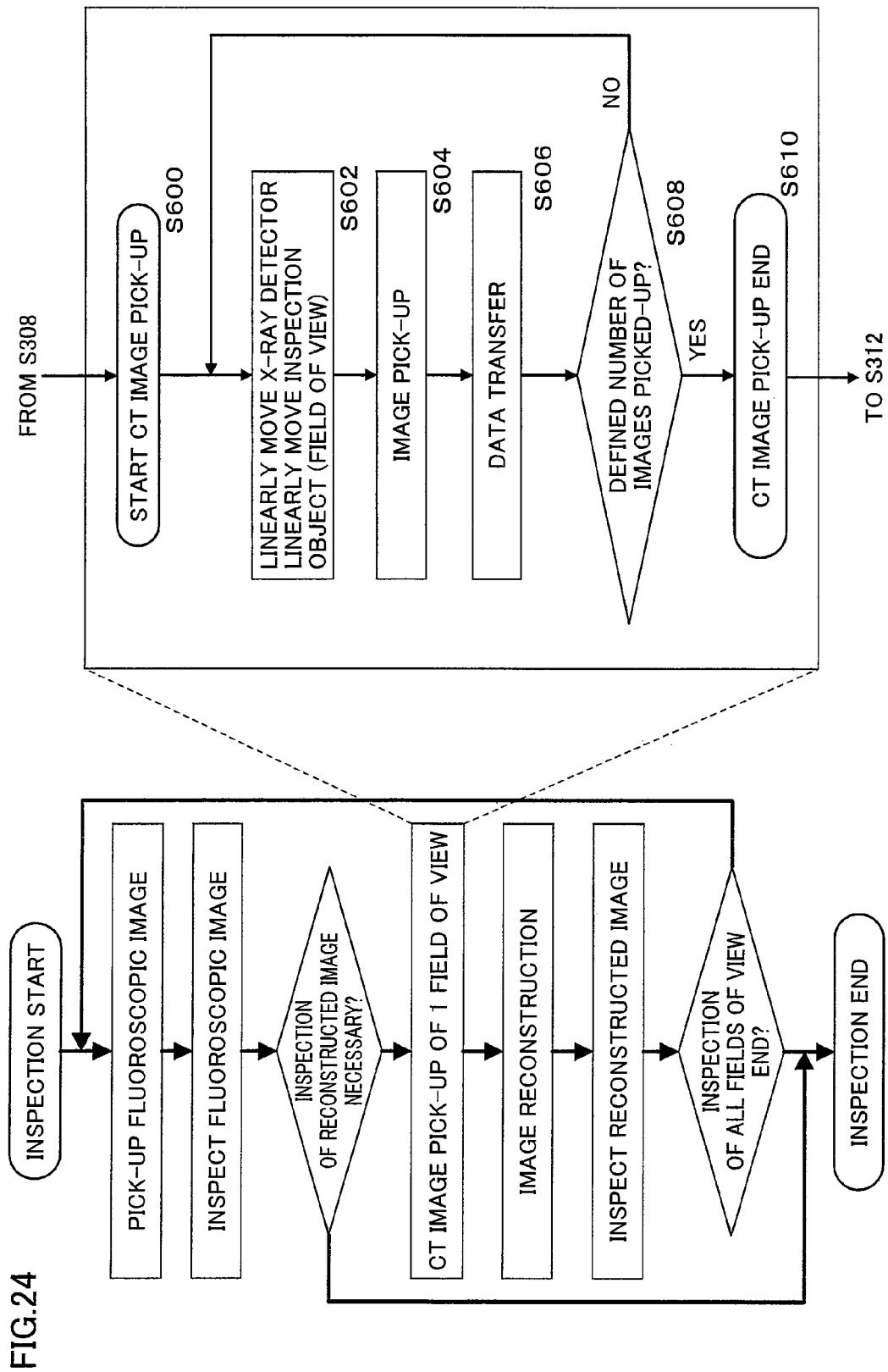
FIG. 24 is a flowchart of inspection when X-ray detector 23 is moved for inspection as in the example of FIG. 22 or 23.

FIG. 24 is a flowchart of inspection when X-ray detector 23 is moved for inspection as in the example of FIG. 22 or 23.

Here again, the flow of the overall inspection is similar to that shown in FIG. 12. FIG. 24 represents the portion of CT image pick-up for one field of view of step S310 shown in FIG. 12.

Therefore, FIG. 24 shows a flowchart of CT image pick-up for one field of view of step S310 described with reference to FIG. 12.

Figure 25:
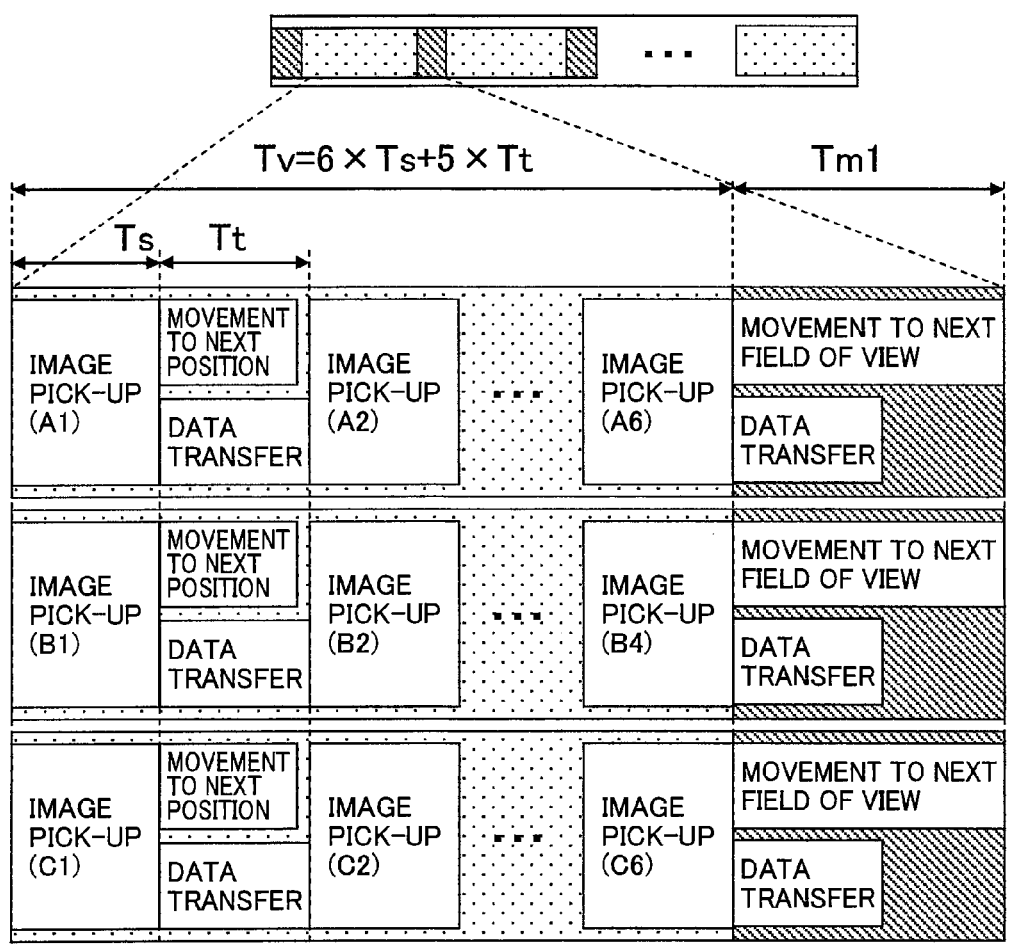
FIG. 25 is a timing chart representing operations of the X-ray detectors and the X-ray focal point with time of inspection, in the inspection flow shown in FIG. 24.

FIG. 25 is a timing chart representing operations of the X-ray detectors and the X-ray focal point with time of inspection, in the inspection flow shown in FIG. 24.

Referring to FIGS. 24 and 25, when the CT image pick-up process for one field of view starts (S600), computing unit 70 moves the object of inspection in the X-Y plane so that the field of view to be inspected is moved to an appropriate position. Then, computing unit 70 also linearly moves X-ray detectors 23.1, 23.2 and 23.3 to the initial position (S602), Thereafter, computing unit 70 causes X-ray emission from X-ray focal points Fa, Fb and Fc to X-ray detectors 23.1, 23.2 and 23.3, respectively at the same time, so that images are picked-up by X-ray detectors 23.1, 23.2 and 23.3 simultaneously (S604). The time of image pick-up (exposure time of X-ray detector) may be set in advance, or a desired time may be set by the user based on visual observation.

Then, computing unit 70 moves X-ray detectors 23.1, 23.2 and 23.3 to the next position of image pick-up, and transfers the image data acquired by X-ray detector 23.1, 23.2 and 23.3 to memory 90, for example, for the reconstruction process by 3D image reconstructing unit 78 (S606).

Thereafter, computing unit 70 determines whether the number of picked-up images has reached the defined number (S608). If the number has not yet reached the defined number for image reconstruction, computing unit 70 returns the process to step S602. If the number has reached the defined number, computing unit 70 ends the CT image pick-up for one field of view (S610), and the process proceeds to S312.

Here again, though the determination as to whether the defined number has been reached is made after data transfer in the flowchart, it is preferred that the determination of picked-up image number is made simultaneously with the data transfer, from the same reason as described with reference to Embodiment 1.

The time of image pick-up for one field of view using the image pick-up method in accordance with Embodiment 2 shown in FIG. 25 will be further described.

Generally, the relation of the following equation holds.

$$Tv=(N/S)Ts+(N/S-1)Tt$$

The definitions of signs are as follows.

Tv: time necessary for picking-up one field of view

Tm: time for moving the moving mechanism (stage, X-ray detector)

Ts: time for image pick-up (exposure time of X-ray detector)

Tt: time for transferring picked-up image data

Since the X-ray detector is moved linearly, the time for moving the X-ray detector can be reduced, and the distance of movement of the field of view is very short as compared with the movement of X-ray detector (as it is in reverse proportion to magnification, the distance is typically about one tenth). Therefore, Tm<Tt.

In the following, description will be made assuming that the object of inspection is divided into M (for example, four) fields of view, and 18 images are picked up as CT images.

As regards the time of CT image pick-up of one field of view, using multiple X-ray sources, three images can be acquired simultaneously by one image pick-up operation. The time Tv for CT image pick-up for one field of view is the sum of 6 times of image pick up and 5 times of acquired image transfer, which is represented by Equation (17) below. Here, it is assumed that the data transfer of the picked-up images is performed simultaneously with the mechanical movement of X-ray detector 23 and the object of inspection.

$$Tv=6Ts+5Tt \quad (17)$$

Therefore, as compared with (16Ts+15Tm) by the method using one detector, the time for image pick-up can be reduced.

If the intensity of X-ray source is enhanced and the sensitivity of X-ray detector is improved, the exposure time of X-ray detector necessary for image pick-up becomes shorter. Therefore, as the method for CT image pick-up, the iterative method is preferred rather than the Feldkamp method, as described above.

Embodiment 3

In Embodiment 1 or Embodiment 2 described above, the effect of reducing inspection time has been discussed mainly from the viewpoint of the time of moving X-ray detector 23 and the object of inspection in CT image pick-up for one field of view.

In Embodiment 3, reduction of inspection time when a plurality of fields of view (portions to be inspected) of one object of inspection are inspected successively will be described.

(Problems when Images are Picked-Up with Field of View (Object of Inspection) or X-Ray Detector Rotated)

Considering an imaging system using the analytical method, it is preferred that the direction of X-ray detector is along a circular orbit, about the center of reconstruction area, from the relation of filtering for reconstruction.

Therefore, when the X-ray detector is to be moved for picking up images from a plurality of angles, it may be moved i) on the circular orbit with the area of reconstruction being the center, or ii) using an X-Y-θ stage. As a result, complicated mechanism is necessary and the cost becomes relatively high if the speed of the movement of the X-ray detector and the stage is to be increased.

Further, it is preferred that the tomographic image used for inspection has a rectangular shape. This is because the inspection algorithm is designed assuming a rectangular image. Further, the object of inspection is wider than the reconstruction area (field of view) obtained by the CT image pick-up. Therefore, by connecting a plurality of fields of view, a wider area is obtained. The object of inspection can efficiently be covered by connecting rectangular fields of view.

Figure 26:
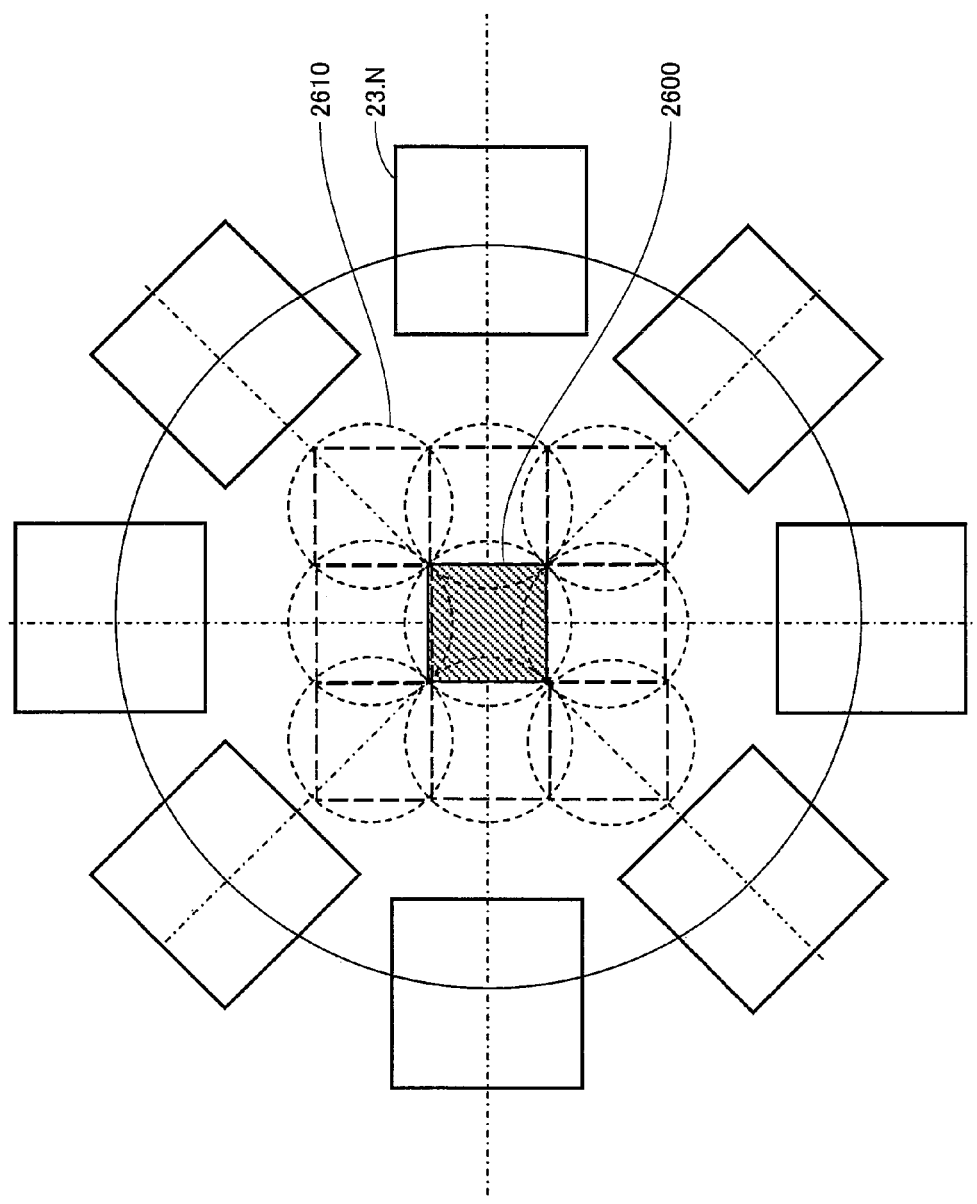
FIG. 26 is a schematic illustration showing an area that can be covered as an inspection area by CT image pick-up of one field of view, for image reconstruction using analytical method.

FIG. 26 is a schematic illustration showing an area that can be covered as an inspection area 2600 by CT image pick-up of one field of view, for image reconstruction using analytical method, when images are picked up by rotating X-ray detector 23.N.

When the reconstruction is done in accordance with the analytical method, at a certain cross section of the reconstructed image, an area that can be used for inspection is a circle. The reason for this is as follows. In the analytical algorithm, the process of back-projection as described above is used. Therefore, when the image detected by the X-ray detector at each image pick-up position is back-projected, the area effectively back-projected comes to be a circle. Here, if a rectangular area is cut out from the circular reconstructed area 2610 obtained by the analytical method, the area of one field of view becomes small, and hence, it takes long time to inspect a wide area of inspection.

The shape of the reconstruction area (field of view) corresponds to the portion where the rectangular images picked-up by X-ray detectors overlap. In an imaging system in which the field of view (object of inspection) rotates, rectangles taken from a plurality of angles overlap, resulting in a circular shape. Since the area to which the inspection algorithm can be applied is rectangular, only the rectangular portion in the circle can be inspected if the reconstruction area has a circular shape. Namely, the area that can be inspected at one time corresponds to the rectangle inscribed in the circle.

For instance, let us represent the length of one side of a cross section of the field of view that can be picked-up by the X-ray detector by 2L. The reconstructed area is a circle having the radius of L. A square inscribed in the circle has each side of $\sqrt{2}$L. The square is the area that can be inspected. Therefore, the area that can be inspected by the conventional imaging system is $2L^2$.

It means that the reconstructed image formed by the conventional imaging system uses only a part of the image data acquired by the X-ray detector. As a result, the size of one field of view is small, and images of a large number of fields of view must be picked-up.

Further, from the viewpoint of increasing the speed of inline inspection, the number of CT images to be picked up should be smaller to attain higher speed. In the analytical method, however, there is a problem that, if the number of images is small, much noise including artifact results. Therefore, images may not be appropriate for inspection.

Now, assume that a plurality of images necessary for reconstruction are to be picked up with the arrangement of the X-ray detector and the X-ray source as shown in FIG. 3, that is, with the X-ray source and the X-ray detector fixed and the field of view moved (rotated) mechanically. In that case, the time required for overall inspection will be as follows.

Figure 27:
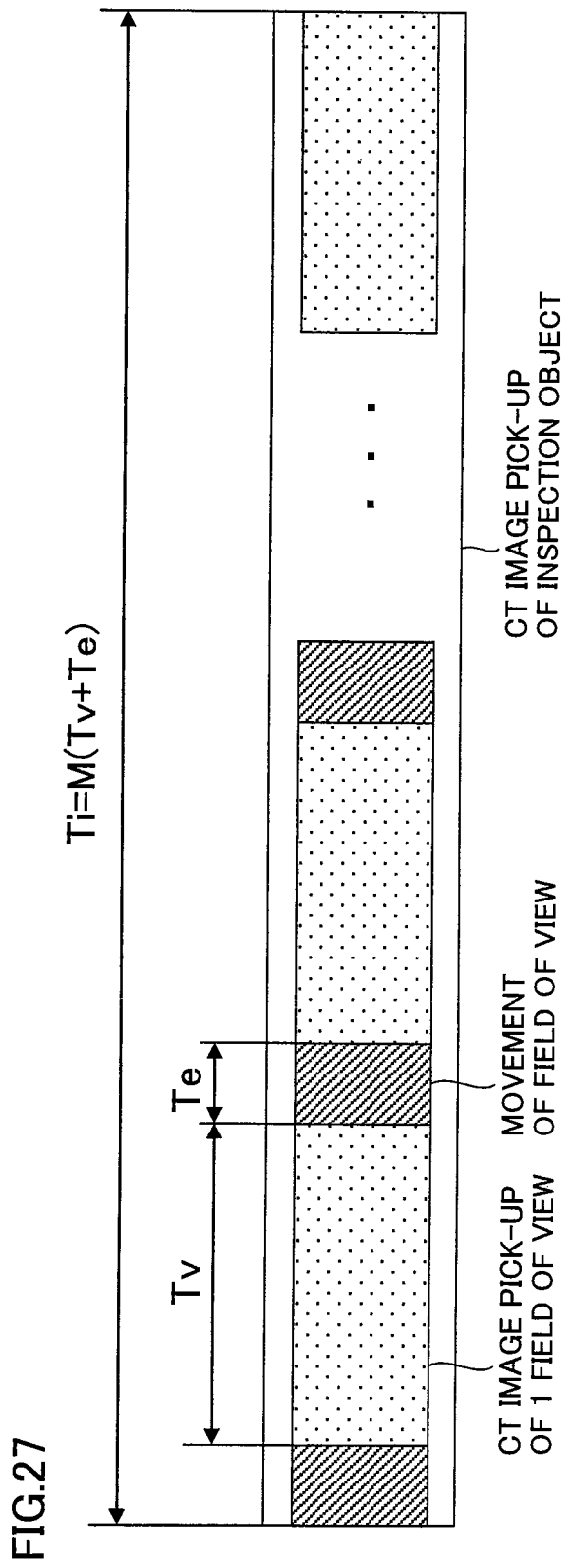
FIG. 27 is a timing chart of a conventional imaging system in which the field of view (object of inspection) is rotated.

FIG. 27 is a timing chart of a conventional imaging system in which the field of view (object of inspection) is rotated.

The flow of the overall inspection is, for example, the same as that described with reference to FIG. 6.

In the following description, it is assumed that the object of inspection is divided into M (for example, four) fields of view, and N images are picked-up as CT images. Definitions of signs are the same as described above.

The CT image pick-up time Ti of the entire object of inspection is the sum of the time for image pick-up of M fields of view and the time of mechanical movement of (M−1) times, and hence, it is given by Equation (18) below.

$$Ti=M(Tv+Te) \quad (18).$$

Figure 28:
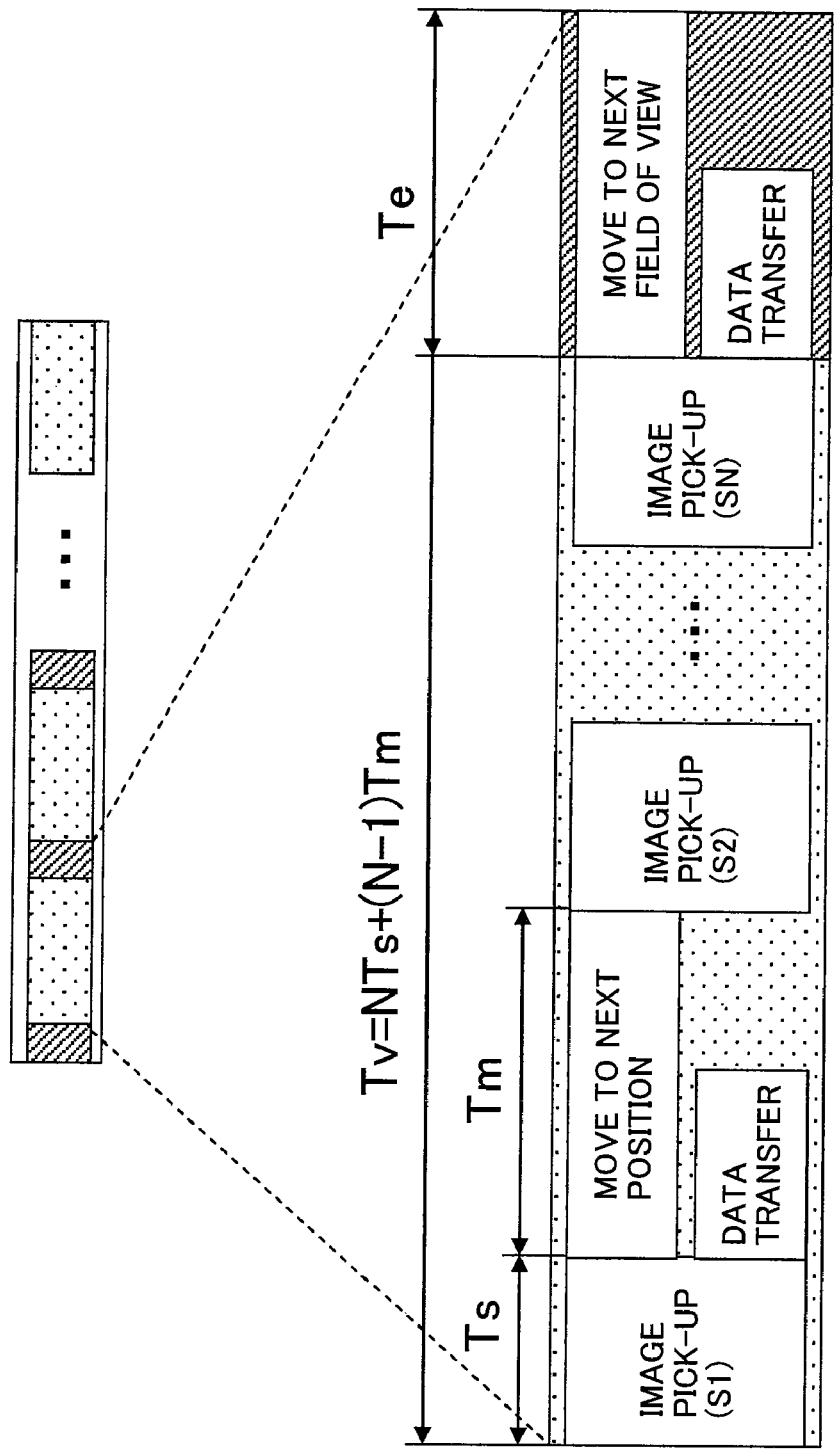
FIG. 28 is an illustration related to CT image pick-up time of one field of view.

FIG. 28 is an illustration related to CT image pick-up time of one field of view. Referring to FIG. 28, the CT image pick-up time Tv for one field of view is the sum of the time of image pick-up of N times and the time of mechanical movement of N times and, hence, it is given by Equation (19) below. Here, the data transfer of picked up image data is performed simultaneously with the mechanical movement.

$$Tv=NTs+(N-1)Tm \quad (19).$$

(Configuration of X-Ray Inspecting Apparatus 106 in Accordance with Embodiment 3)

As will be described in the following, in X-ray inspecting apparatus 106 in accordance with Embodiment 3, first, X-ray detector 23 is positioned in translational manner, and using the iterative method, the limitation of circular orbit of X-ray detector is eliminated, to attain higher speed. Second, in X-ray inspecting apparatus 106, X-ray detector 23 is positioned in a translational manner, and using the iterative method, the effective rectangular area is increased and the number of division of the field of view is made smaller, to attain higher speed of the system operation. Third, by using the iterative method, generation of highly precise reconstructed image is made possible from fewer number of picked-up images, to attain higher speed of the system operation.

Specifically, in X-ray inspecting apparatus 106, at least one X-ray detector 23 is arranged in a translational manner for the rectangular area necessary as each inspection area (field of view) of the object of inspection. X-ray detector 23 moves in a translational manner in the same plane as the detection surface of the X-ray detector. As the method for reconstruction for image reconstruction, the iterative method is used.

Here, the X-ray source as X-ray source 10 may not be a scanning X-ray source. It may be one fixed-focus X-ray source, or a plurality of X-ray sources may be provided.

Figure 29:
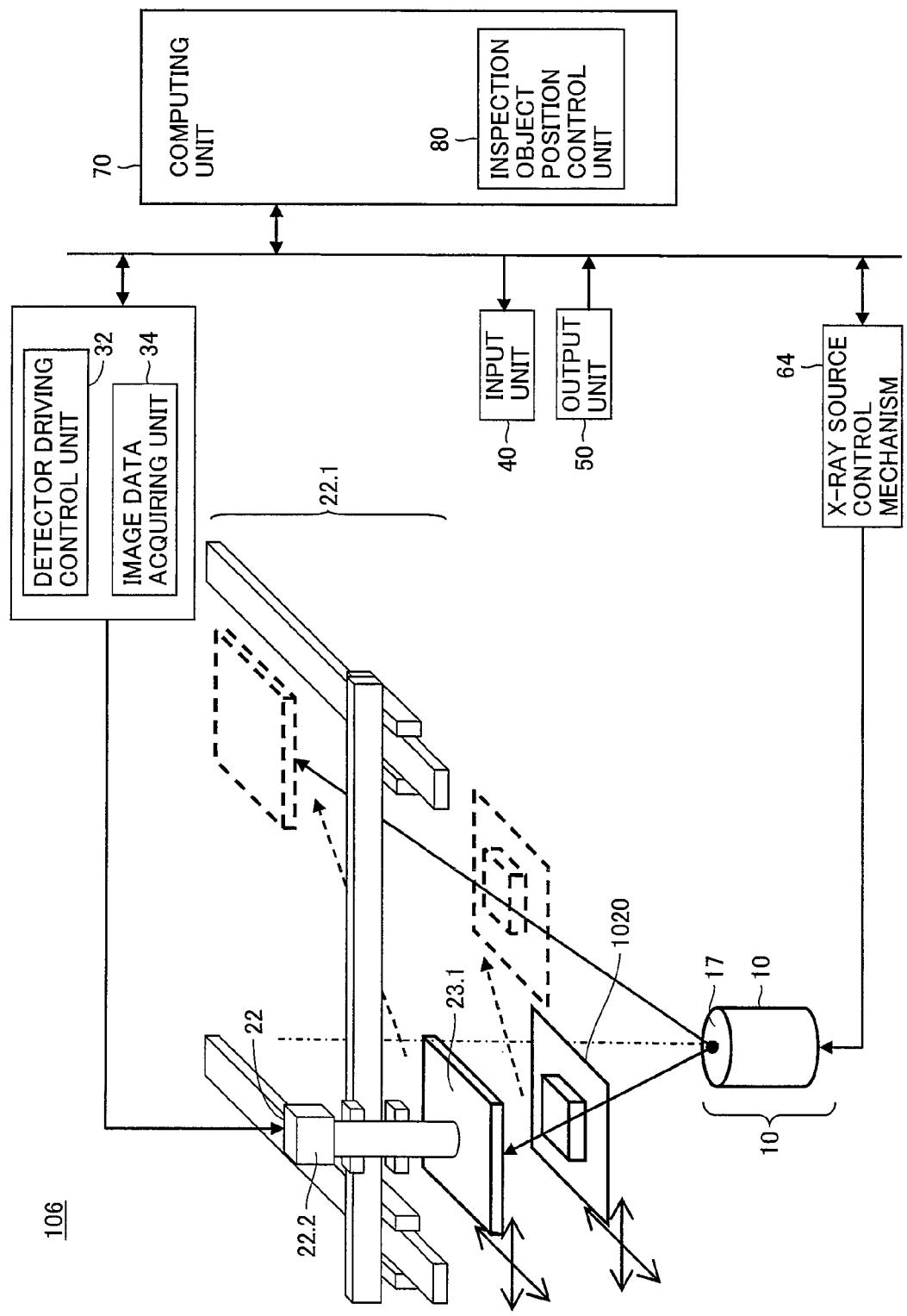
FIG. 29 illustrates a configuration of an X-ray inspecting apparatus 106 in accordance with Embodiment 3.

FIG. 29 illustrates a configuration of an X-ray inspecting apparatus 106 in accordance with Embodiment 3.

The same portions as in FIG. 1 are denoted by the same reference characters, and portions necessary for the description are extracted from portions directly related to the control of X-ray focal point position, the control of X-ray detector position and the control of the position of object of inspection.

Referring to FIG. 29, X-ray detector driving unit 22 includes a robot arm that can move X-ray detector 23.1 in the translational manner in the X-Y plane. In the example of FIG. 29, a fixed-focus X-ray source is used as X-ray source 10.

In the configuration shown in FIG. 29, in order to move the position of the object of inspection in the X-Y plane independently from X-ray detector 23, an inspection object position driving mechanism 1020 (for example, an X-Y stage) and inspection object position control unit 80 are provided.

X-ray detector driving unit 22 includes an orthogonal two-axis robot arm 22.1 and a detector support unit 22.2, and moves X-ray detector 23 to a designated position in accordance with an instruction from computing unit 70 through detector driving control unit 32. Further, detector driving control unit 32 transmits the position information of X-ray detector 23 at that time point to computing unit 70. It is noted that other mechanism having a configuration allowing movement in the X-Y direction and having similar functions related to the movement of X-ray detector 23 may be used.

Computing unit 70 transmits instructions to detector driving control unit 32, image data acquiring unit (X-ray detector controller) 34 and scanning X-ray source control mechanism 60, and executes a program represented by the flowchart of inspection process as will be described later.

Inspection object position control mechanism 1020 includes an actuator and a mechanism for fixing the object of inspection, and moves the object of inspection in accordance with an instruction from inspection object position control unit 80.

Computing unit 70 acquires X-ray fluoroscopic image and transfers picked-up image data at a timing designated by an instruction through detector driving control unit 32.

Figure 30:
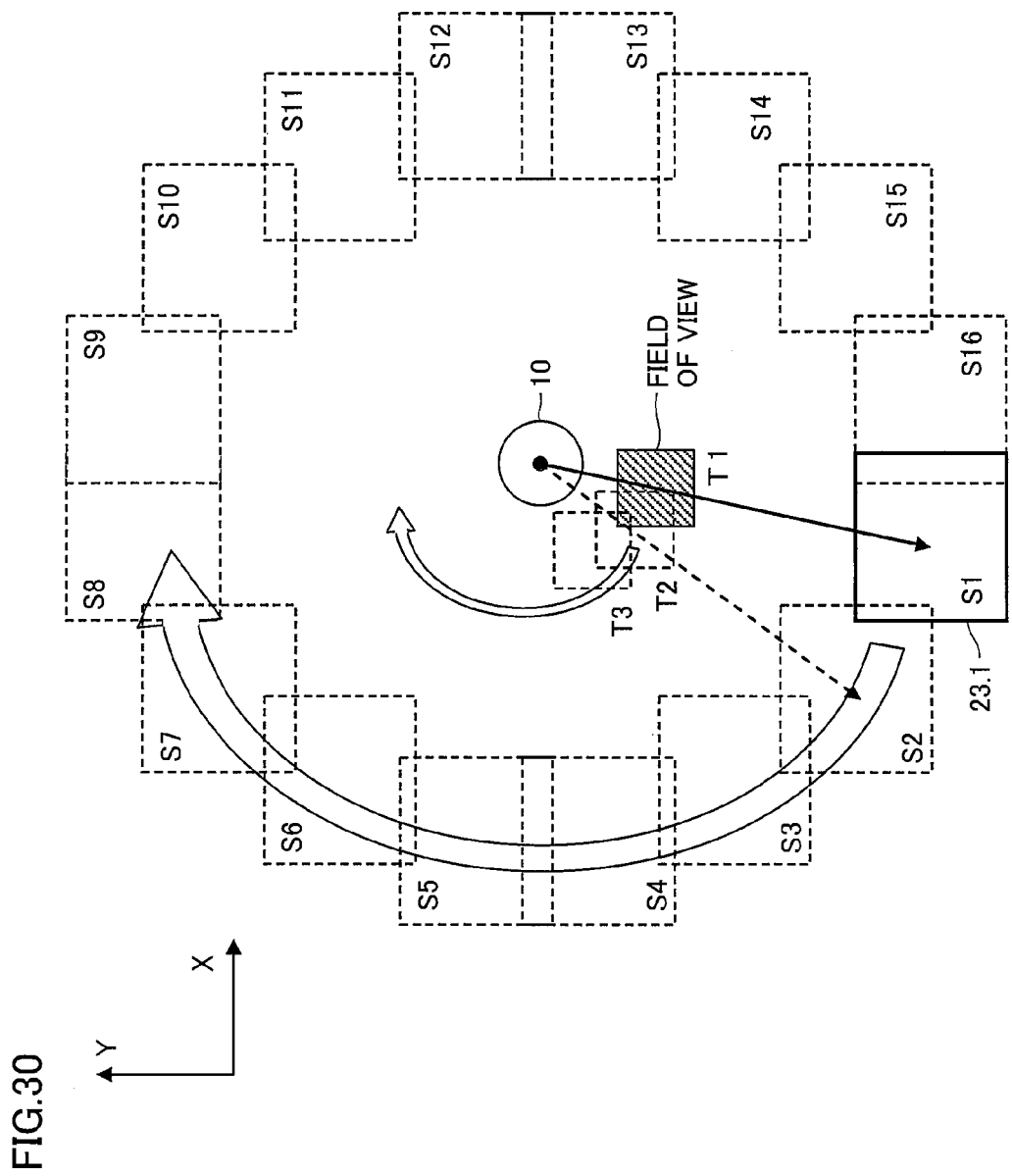
FIG. 30 is a top view showing movement trajectory of X-ray detector 23 and the field of view of the object of inspection, in the configuration of X-ray inspecting apparatus 106 shown in FIG. 29.

FIG. 30 is a top view showing movement trajectory of X-ray detector 23 and the field of view of the object of inspection, in the configuration of X-ray inspecting apparatus 106 shown in FIG. 29.

Operation Example 1 of FIG. 30 shows the configuration of FIG. 29 viewed from the above, assuming image pick-up of 16 X-ray fluoroscopic images picked up from equal angles. This operation example is suitable for applying the reconstruction method for the iterative method or tomosynthesis as described above. The reason for this is that by the iterative method or tomosynthesis, the reconstruction is possible regardless of the direction of the X-ray detector.

In such an operation, it is unnecessary to rotate X-ray detector 23. Therefore, the X-ray detector driving mechanism 22 can be simplified, and the speed of operation and maintainability of the mechanism can be improved.

X-ray detector 23 moves at a constant distance from focal point 17 of X-ray source as the origin. As a result, the trajectory of the center of X-ray detector 23 forms a circle when the imaging system is viewed from above.

In FIG. 30, positions T1 and T2 represent positions of fields of view, corresponding to positions S1 and S2 of X-ray detector.

Figure 31:
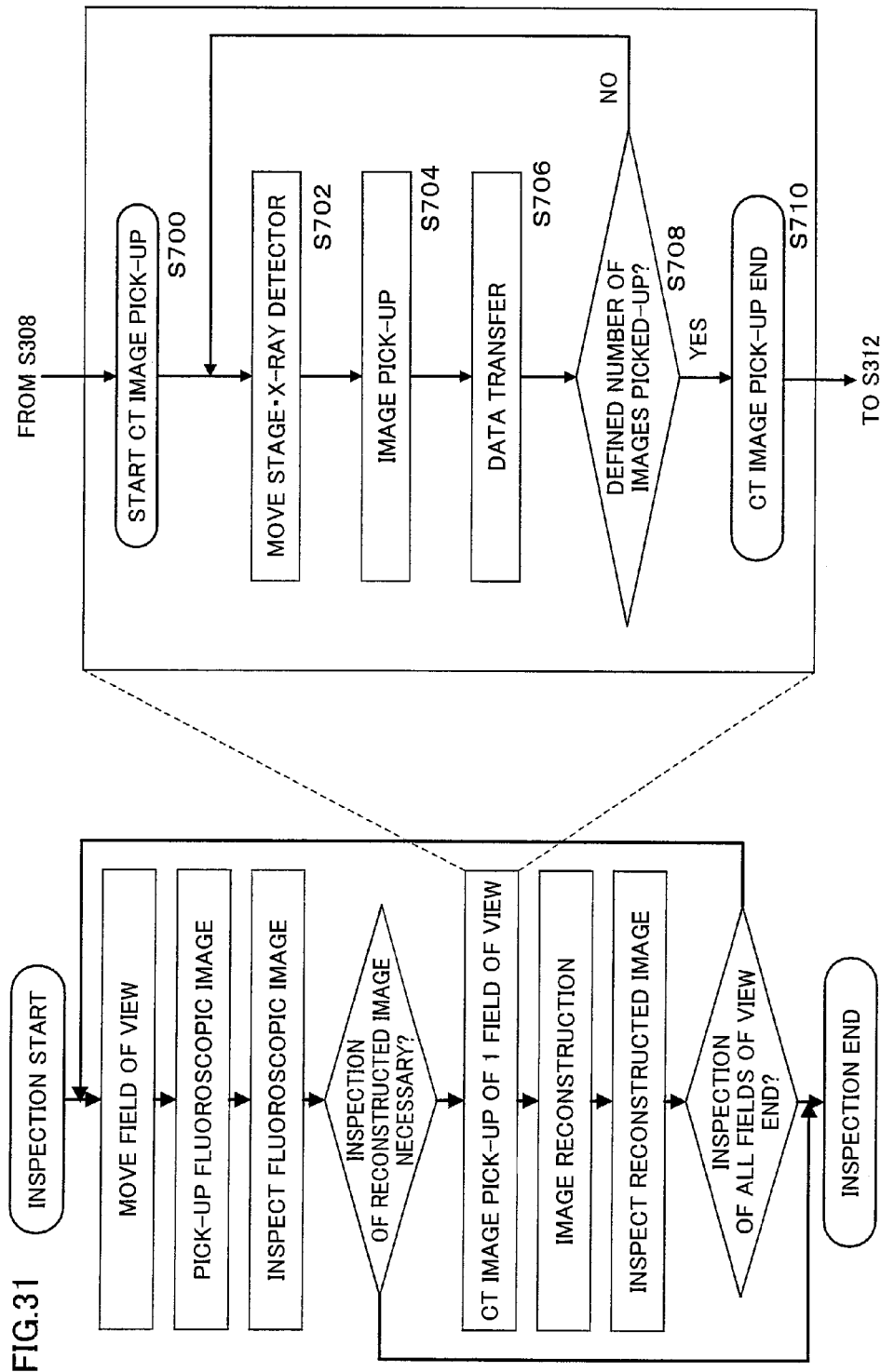
FIG. 31 is a flowchart of CT image pick-up by an imaging system using a translational detector.

FIG. 31 is a flowchart of CT image pick-up by an imaging system using a translational detector.

Here again, the flow of overall inspection is similar to that shown in FIG. 12. FIG. 31 represents the portion of CT image pick-up for one field of view of step S310 shown in FIG. 12.

Therefore, FIG. 31 shows a flowchart of CT image pick-up for one field of view of step S310 described with reference to FIG. 12.

When the CT image pick-up process for one field of view starts (S700), computing unit 70 moves the object of inspection in the X-Y plane so that the field of view to be inspected is moved to an appropriate position. Then, computing unit 70 also moves X-ray detector 23.1 to the initial position (S702). The position of image pick-up can be automatically calculated from design information of CAD data and the like. Since the object of inspection is placed on a stage, the field of view can be moved as the stage is moved.

Thereafter, computing unit 70 causes X-ray emission from X-ray focal point 17 to X-ray detector 23.1, so that an image is picked-up by X-ray detector 23.1 (S704). The time of image pick-up (exposure time of X-ray detector) may be set in advance, or a desired time may be set by the user based on visual observation.

Then, computing unit 70 moves X-ray detector 23.1 to the next position of image pick-up, and transfers the image data acquired by X-ray detector 23.1 to memory 90, for example, for the reconstruction process by 3D image reconstructing unit 78 (S706).

Thereafter, computing unit 70 determines whether the number of picked-up images has reached the defined number (S708). The defined number may be determined from design information such as the CAD data before inspection, or it may be determined based on the visual observation by the operator. If the number has not yet reached the defined number for image reconstruction, computing unit 70 returns the process to step S702. If the number has reached the defined number, computing unit 70 ends the CT image pick-up for one field of view (S710), and the process proceeds to S312.

Here again, though the determination as to whether the defined number has been reached is made after the data transfer in the flowchart, it is preferred that the determination of picked-up image number is made simultaneously with the data transfer, from the same reason as described with reference to Embodiment 1.

Figure 32:
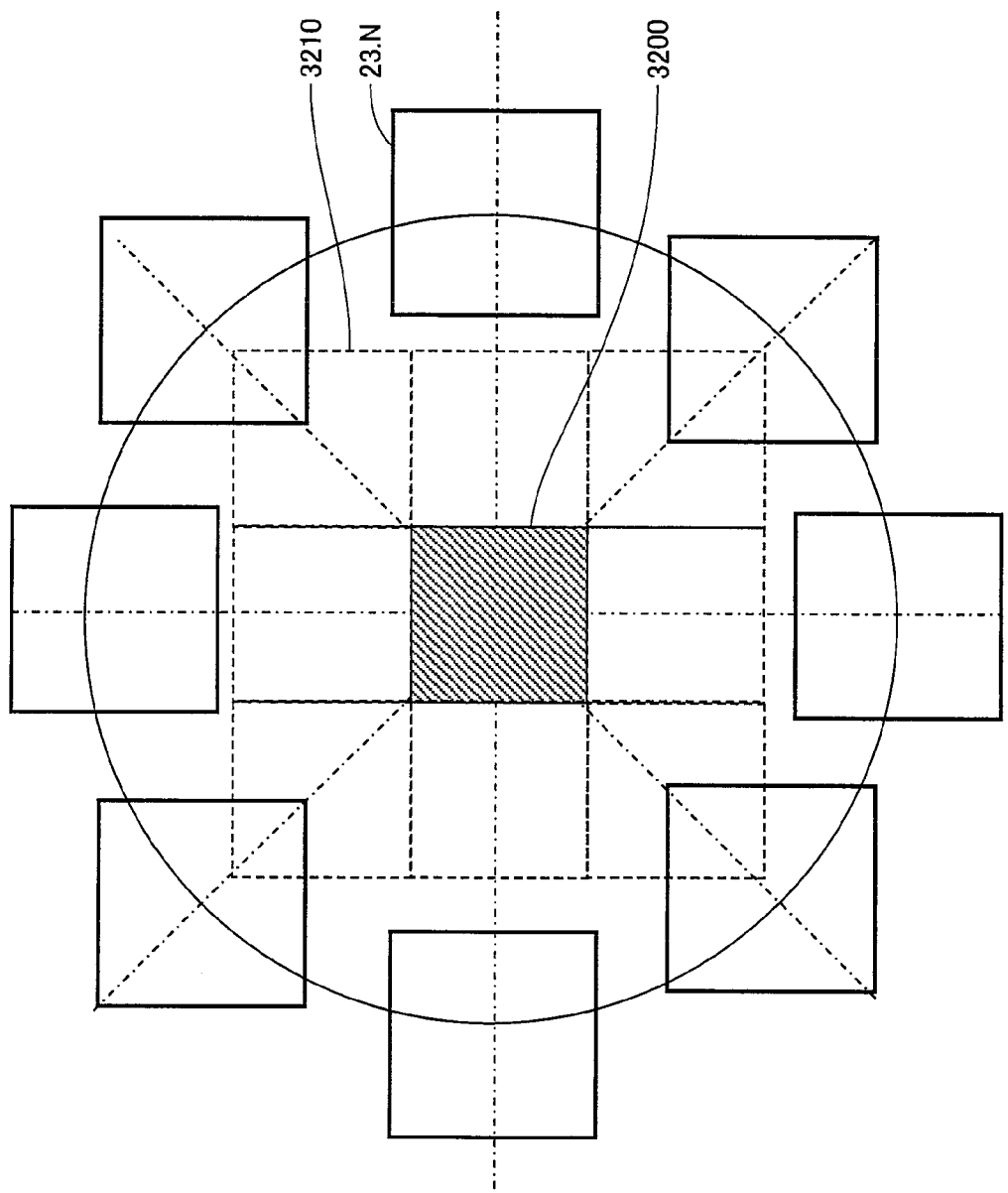
FIG. 32 is a schematic illustration showing an inspection area by an imaging system using a translational X-ray detector.

FIG. 32 is a schematic illustration showing an inspection area by an imaging system using a translational X-ray detector.

The shape of reconstruction area (field of view) 3210 corresponds to the portion where the rectangular images picked-up by X-ray detectors 23.N overlap. In the imaging system shown in FIG. 26, rectangles taken from a plurality of angles overlap, resulting in a circular shape. In the system of FIG. 32, X-ray detectors all face the same direction and, therefore, the overlapped portions come to have a rectangular shape.

If the reconstruction area has a circular shape, only the rectangular area in the circle can be used, since the area to which the inspection algorithm can be applied is rectangular. Therefore, only a small area can be inspected at one time. On the other hand, in the example shown in FIG. 32, the reconstruction area 3210 is rectangular, and therefore, the area that can be inspected in reconstructed area 3210 is relatively large. As a result, the total number of images to be picked-up can be reduced and the inspection time can be reduced. Further, it requires smaller number of images to dispose rectangles with no space therebetween, than to dispose circles with no space therebetween. Namely, the number of images to be picked-up can be reduced, and the inspection time can be reduced.

Let us represent the length of one side of a cross section of the field of view that can be picked-up by the X-ray detector by 2L. The reconstruction area is a square having each side of length 2L. Therefore, when inspection areas 3200 are arranged as shown in FIG. 32, the area that can be inspected will be $4L^2$. The area that can be inspected by the imaging system of FIG. 26 was $2L^2$ and, therefore, compared with the conventional system, an area twice as large can be inspected for one field of view. In other words, the number of division of the field of view can be decreased by half.

The effect described above can be attained by a detector that moves linearly, or by a plurality of detectors, provided that the X-ray detector moves in a translational manner. The X-ray source may be a fixed-focus X-ray source or a scanning X-ray source.

Figure 33:
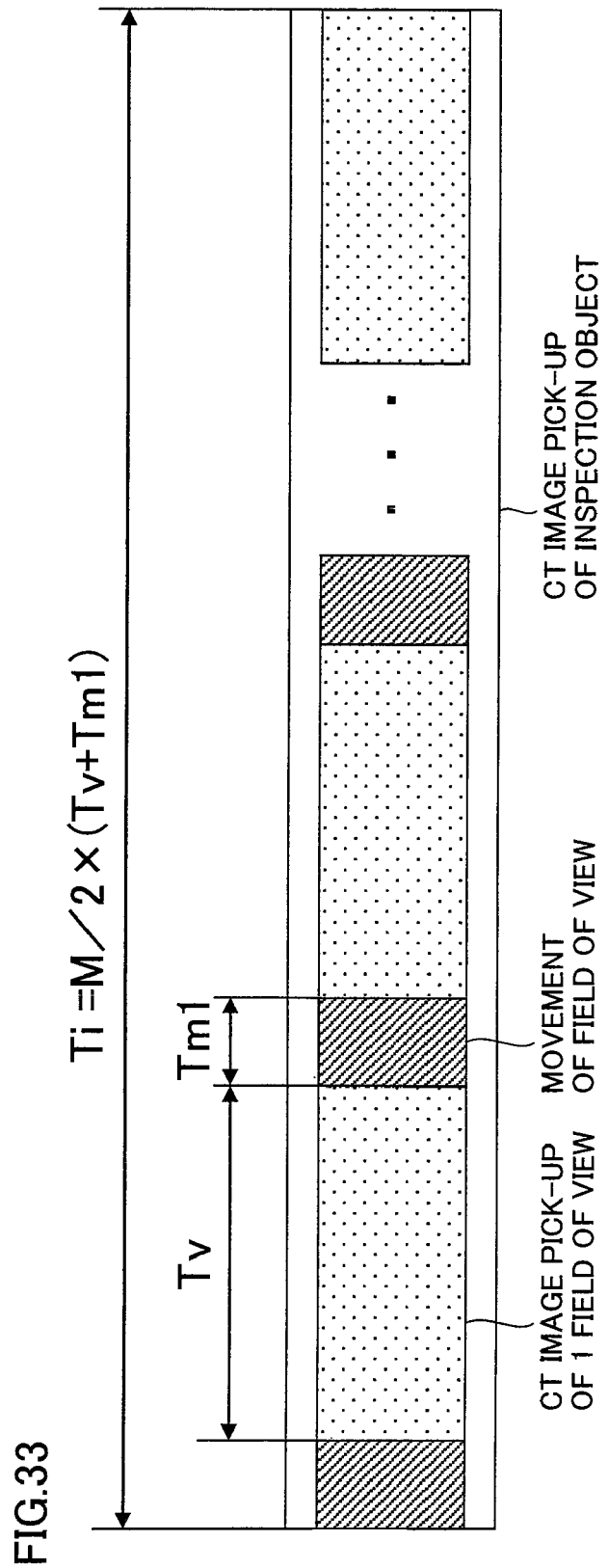
FIG. 33 is a timing chart of the imaging system using a translational X-ray detector.

FIG. 33 is a timing chart of the imaging system using a translational X-ray detector.

In the following description, it is assumed that the object of inspection is divided into M fields of view in the imaging system, and N images are picked-up as CT images. Definitions of signs are the same as described above.

In X-ray inspecting apparatus 106 shown in FIG. 29, the number of division of field of view can be decreased by half as compared with the imaging system described with respect to FIG. 26. Therefore, the number of fields of view is M/2.

The CT image pick-up time Ti for the entire object of inspection is the sum of image pick-up of M/2 fields of view and mechanical movement of M/2 times, and therefore, it is given by Equation (20).

$$Ti = M/2(Tv + Te) \qquad (20).$$

As described above, in the X-ray inspecting apparatus in accordance with Embodiment 3, when images are picked up for CT reconstruction, images in the range covered by the movement of X-ray detector are picked up in one plane, and the direction of X-ray detector is kept in the same direction. The mode of movement of X-ray detector and the object of inspection (stage) is limited to two axes of X-Y, the mechanism of the moving means is simplified, and the speed of movement is increased. Further, since the X-ray detector and the object of inspection are translated relative to each other, the field of view resulting from CT reconstruction comes to have a rectangular shape, and the effective scope of automatic inspection is enlarged. Thus, the speed of operation in the automatic inspection system can be increased.

Embodiment 4

In Embodiments 1 to 3 above, X-ray inspecting apparatuses enabling reduction of inspection time loss resulting from mechanical movement of X-ray detector 23 or the object of inspection have been described.

In Embodiment 4, reduction of inspection time attained by pulse-driving the X-ray source will be described.

For high-speed image pick-up, the X-ray should preferably have higher intensity. If the current of electron beam is increased to attain higher X-ray intensity, however, the target will be thermally damaged, due to impinging electron beam. Therefore, the target can be irradiated with the electron beam only for a short period of time until the temperature rises to a level possibly leading to thermal damage, if the current of electron beam is increased. In the X-ray inspecting apparatus in accordance with Embodiment 4, the problem of heat is solved by using "a plurality of X-ray detectors" and "a focal scanning X-ray source" and the X-ray intensity is increased to attain higher speed, as will be described in the following.

(Problems when a Plurality of X-Ray Detectors and a Scanning X-Ray Source are Used for CT Image Pick-Up)

In the following, before describing the configuration and operation of X-ray inspecting apparatus in accordance with Embodiment 4, as a background, the problem when CT image pick-up is done using a plurality of X-ray detectors and a scanning X-ray source will be described.

Figure 34:
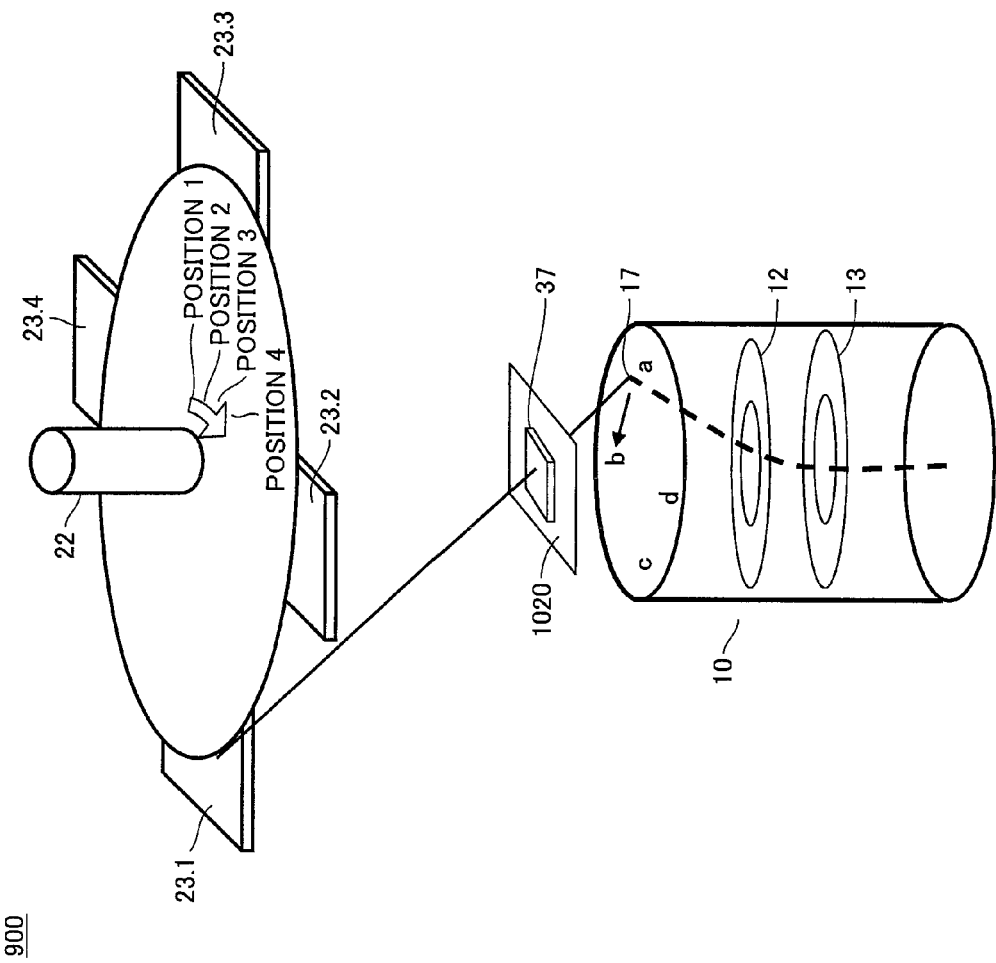
FIG. 34 illustrates a configuration of an X-ray inspecting apparatus picking-up images using four detectors and a scanning X-ray source.

FIG. 34 illustrates a configuration of an X-ray inspecting apparatus picking-up images using four detectors and a scanning X-ray source. The same portions as in FIG. 1 are denoted by the same reference characters, and in FIG. 34, portions other than those directly necessary for the description are not shown.

An X-ray inspecting apparatus 900 shown in FIG. 34 includes a scanning X-ray source 10 and four X-ray detectors 23.1 to 23.4.

X-ray detectors 23.1 to 23.4 are fixed on detector driving mechanism 22. In FIG. 34, image pick-up of 16 images is assumed, and therefore, detector driving mechanism 22 rotates from position 1 to position 4 for picking-up images.

X-Y movement of a field of view 37 of the object of inspection independent from X-ray detectors 23.1 to 23.4 and from the X-ray source is made possible by inspection object position driving mechanism 1020. In the configuration shown in FIG. 34, by scanning of X-ray focal point, it is possible to irradiate one field of view with X-ray from different angles. Therefore, it is possible to pick-up fluoroscopic images of one field of view from a plurality of directions, without moving the object of inspection.

The operation at the time of inspection is as follows.

During image pick-up by one X-ray detector 23, the X-ray focal point position 17 is not moved. Images are picked up successively by four X-ray detectors 23.1 to 23.4, and at that time, X-ray focal point position 17 is at a point where the target and a line connecting the center of each detector and the center of field of view intersect.

When image pick-up by four X-ray detectors 23.1 to 23.4 ends, the four detectors are simultaneously moved to the next position of image pick-up by detector driving unit 22.

Figure 35:
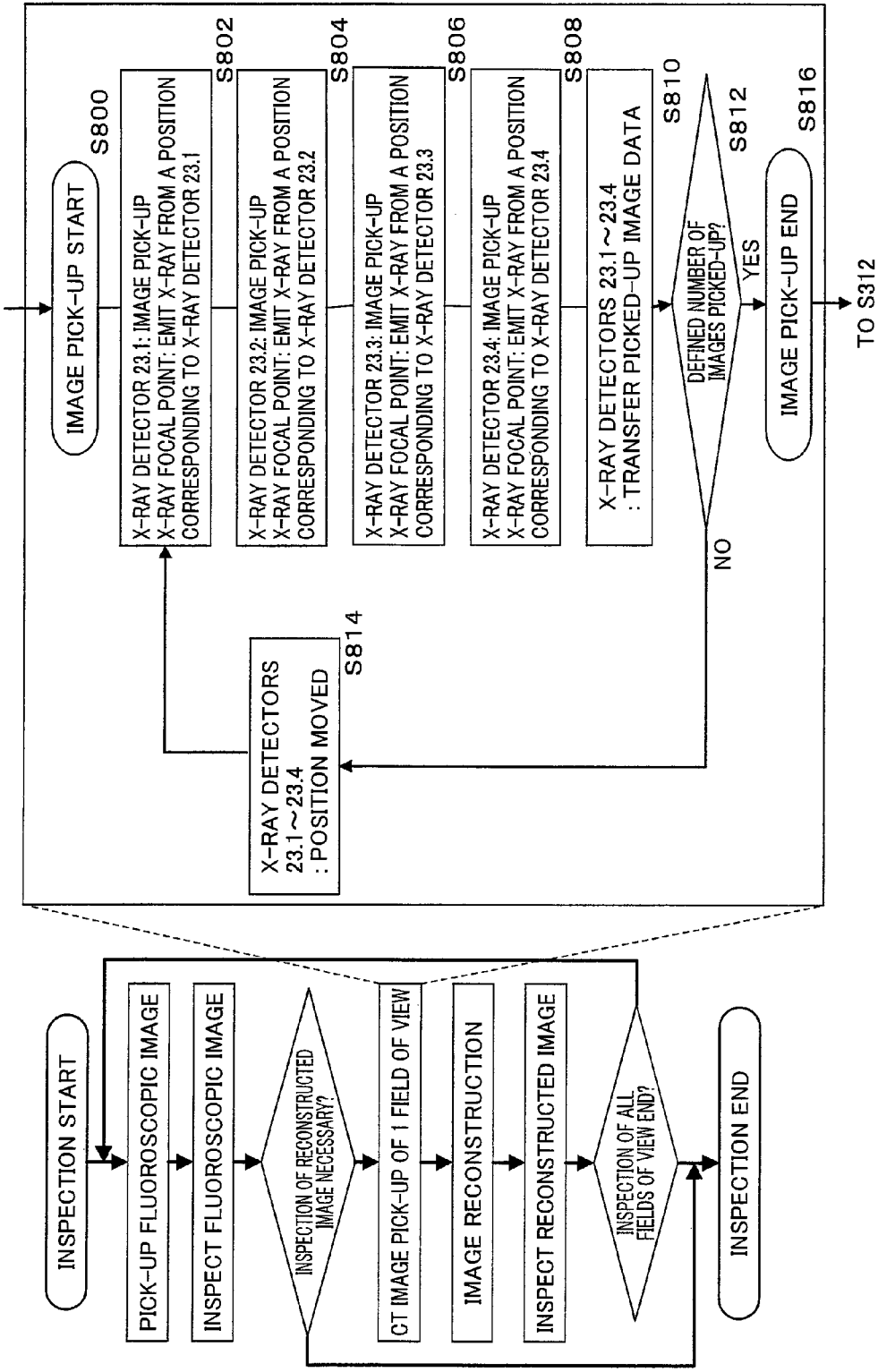
FIG. 35 is a flowchart of CT image pick-up by X-ray inspecting apparatus 900 shown in FIG. 34.

FIG. 35 is a flowchart of CT image pick-up by X-ray inspecting apparatus 900 shown in FIG. 34.

Here again, the flow of overall inspection is similar to that shown in FIG. 12. FIG. 35 represents the portion of CT image pick-up for one field of view of step S310 shown in FIG. 12.

Therefore, FIG. 35 shows a flowchart of CT image pick-up for one field of view of step S310 described with reference to FIG. 12.

Figure 36:
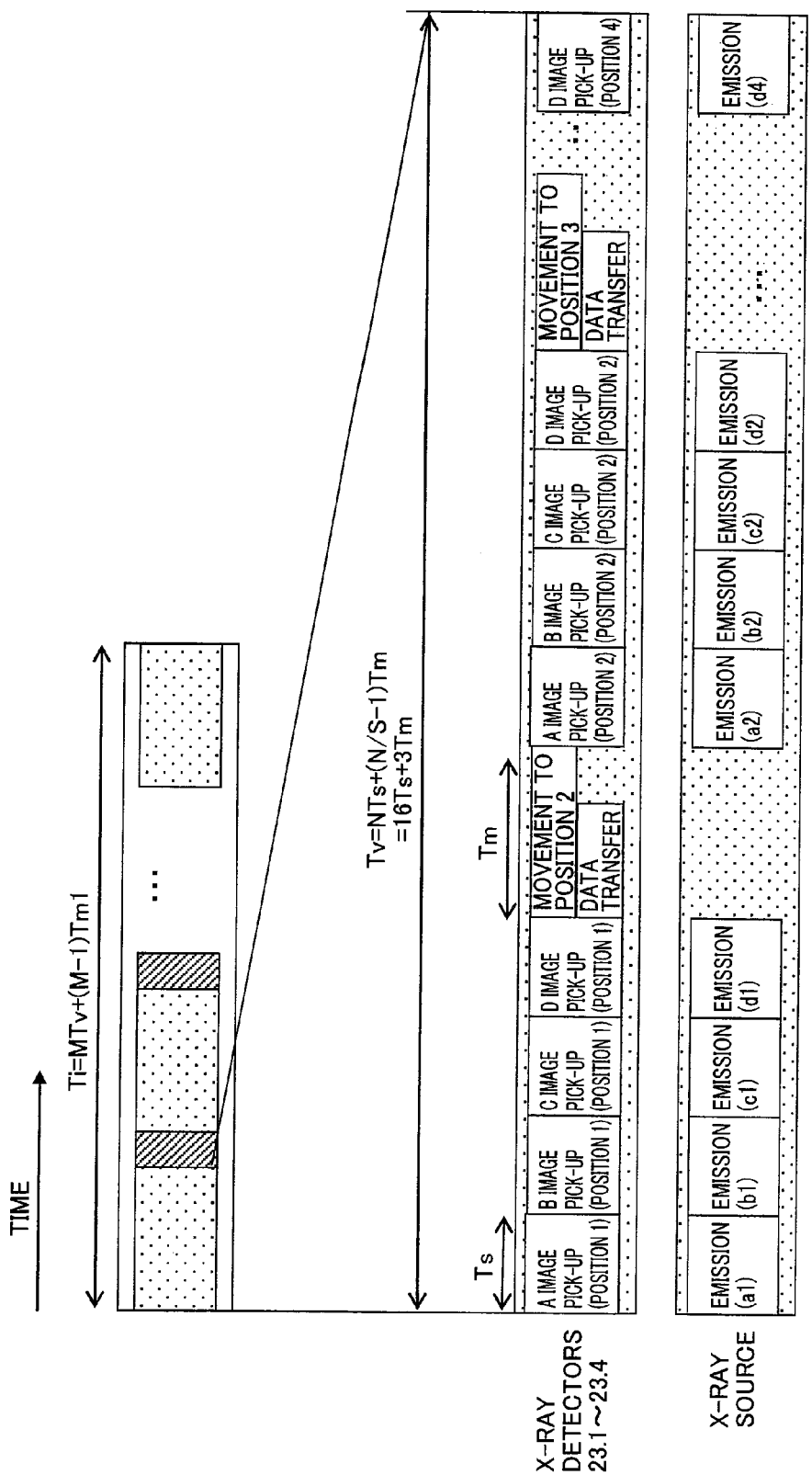
FIG. 36 is a timing chart representing operations of the X-ray detectors and the X-ray focal point with time of inspection, in the inspection flow shown in FIG. 35.

FIG. 36 is a timing chart representing operations of the X-ray detectors and the X-ray focal point with time of inspection, in the inspection flow shown in FIG. 35.

Referring to FIGS. 35 and 36, when the CT image pick-up process for one field of view starts (S800), computing unit 70 moves the object of inspection in the X-Y plane so that the field of view to be inspected is moved to an appropriate position. Then, computing unit 70 also moves X-ray detector driving mechanism 22 to a prescribed position (here, position 1), causes X-ray emission from X-ray focal point 17 to X-ray detector 23.1, so that an image is picked-up by X-ray detector 23.1 (S802).

Next, computing unit 70 causes X-ray emission from X-ray focal point 17 to X-ray detector 23.2, so that an image is picked-up by X-ray detector 23.2 (S804).

Next, computing unit 70 causes X-ray emission from X-ray focal point 17 to X-ray detector 23.3, so that an image is picked-up by X-ray detector 23.3 (S806).

Next, computing unit 70 causes X-ray emission from X-ray focal point 17 to X-ray detector 23.4, so that an image is picked-up by X-ray detector 23.4 (S808).

Thereafter, computing unit 70 transfers the image data acquired by X-ray detectors 23.1 to 23.4 to memory 90, for example, for the reconstruction process by 3D image reconstructing unit 78 (S810).

Thereafter, computing unit 70 determines whether the number of picked-up images has reached the defined number (S812). If the number has not yet reached the defined number for image reconstruction, computing unit 70 passes the control to step S814. If the number has reached the defined number, computing unit 70 ends the CT image pick-up for one field of view (S816), and the process proceeds to S312.

At step S814, computing unit 70 moves X-ray detector driving mechanism 22 to the next prescribed position (here, position 2), and the process proceeds to step S802.

Thereafter, process steps S802 to S810 and S814 are repeated until it is determined at step S812 that the defined number is reached.

Referring to the timing chart of image pick-up from a plurality of directions for one field of view shown in FIG. 36, let us consider image pick-up of N images for CT image pick-up, with the object of inspection divided into M (for example, four) fields of view. Definitions of signs are the same as described above.

The CT image pick-up time Ti of the entire object of inspection is the sum of the time for image pick-up of M fields of view and the time of mechanical movement of (M−1) times, and hence, it is given by Equation (21) below.

$$Ti = MTv + (M-1)Tm \tag{21}$$

Next, the time of CT image pick-up for one field of view will be described.

The time Tv of CT image pick-up for one field of view involves N times of image pick-up operations using S X-ray detectors with N/S movements, and therefore, it is given by Equation (22) below. Here, it is assumed that data transfer of the picked-up images is performed simultaneously with the mechanical movement.

$$Tv = NTs + (N/S - 1)Tm \tag{22}$$

Therefore, the time Tv necessary for taking 16 images of one field of view from different angles by the conventional method shown in FIG. 34 is Tv=16Ts+3Tm.

(Configuration of X-Ray Inspecting Apparatus 110 in Accordance with Embodiment 4)

As will be described in the following, X-ray inspecting apparatus 110 in accordance with Embodiment 4 is adapted to have the following configuration to reduce the time necessary for image pick-up.

Specifically, though the method for image pick-up using focus scanning type X-ray source as described with reference to FIG. 34 is effective in reducing the time of the mechanical movement of the X-ray detector, there is room for improvement from the viewpoint of increasing the speed of image pick-up.

i) A scanning X-ray source is capable of moving the X-ray focal point position at high speed. If images of one area are to be picked-up from different angles and only one X-ray detector is provided, the advantageous characteristic cannot be fully utilized. The reason is that the mechanical movement of the X-ray detector takes much longer time than the movement of X-ray focal point.

ii) On the other hand, if a plurality of X-ray detectors are provided, in the method for acquiring image pick-up data of X-ray detectors in turn using the scanning X-ray source, X-ray detectors other than the one used for image pick-up are not operating. Therefore, it is not the case that the plurality of X-ray detectors effectively contribute to increase of speed.

iii) In order to increase X-ray intensity, it is necessary to increase the target current. In that case, however, the target is prone to thermal damage. Therefore, when a large target current is used, it is necessary to move the focal point before the target temperature increases to the level causing damage to the target, or to shorten the time of irradiation on one point. In that case, however, the amount of X-ray is insufficient for the X-ray detector to acquire image data, since the time of X-ray irradiation is short.

In the X-ray inspecting apparatus in accordance with Embodiment 4, changes are made on the following points, from the configuration of FIG. 34.

1) The target current is increased.
2) A plurality of X-ray detectors are used simultaneously.
3) Time of electron beam irradiation on one point of target is made shorter.
4) During one exposure of X-ray detector, a highly intense electron beam is directed a number of times to the corresponding X-ray focal point position.

Since the electron beam is directed a number of times as pulses to one X-ray focal point position, the portion of the target irradiated with the X-ray beam can be cooled by heat dissipation while it is not receiving the electron beam. Therefore, even a strong electron beam causing temperature increase to cause damage on the target when irradiated for a prescribed time period can be used, as it is moved to the next X-ray focal point position within the time period in which the target temperature is in a tolerable range. Further, since the plurality of X-ray detectors can be used simultaneously for image pick-up, the overall time for image pick-up can be reduced.

Figure 37:
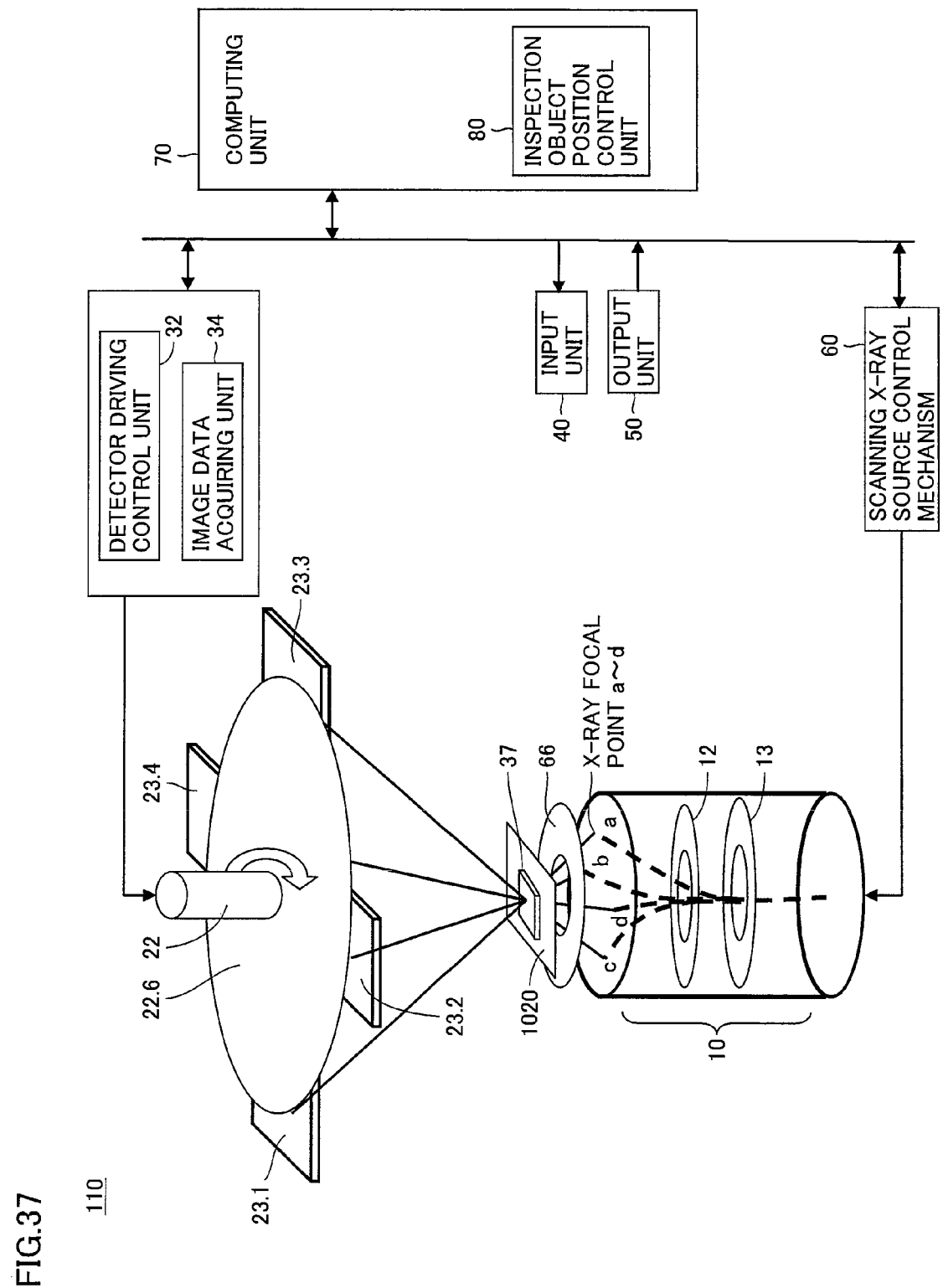
FIG. 37 is a block diagram showing a configuration of an X-ray inspecting apparatus 110 in accordance with Embodiment 4.

FIG. 37 is a block diagram showing a configuration of an X-ray inspecting apparatus 110 in accordance with Embodiment 4.

Referring to FIG. 37, in X-ray inspecting apparatus 110, four X-ray detectors 23.1 to 23.4 are fixed at every 90° on one circumference of a circular sensor base 22.6. When sensor base 22.6 is rotated by X-ray detector driving unit 22, the arrangement of detectors moves to positions 1 to 4 in the similar manner as in FIG. 34.

Further, four X-ray detectors 23.1 to 23.4 are activated simultaneously, and for X-ray sensing, shield 66 is provided to regulate X-ray irradiation such that X-ray focal point position is limited only to the direction of a corresponding detector.

The same portions as in FIG. 1 are denoted by the same reference characters, and description thereof will not be repeated. In FIG. 37, portions of the configuration of FIG. 1 other than those directly necessary for the description are not shown.

In FIG. 37, a system is considered in which the four X-ray detectors move on one circle while the positional relation between each other is kept unchanged. A mechanism allowing independent position control of each detector may be provided. Further, the number of X-ray detectors may be larger than or smaller than four. Similarly, the number of X-ray focal point positions may be larger than or smaller than four, corresponding to the number of X-ray detectors 23.

Operations are as follows.

While X-ray detectors 23.1 to 23.4 perform one image pick-up of fluoroscopic images simultaneously, X-ray focal points are stopped for a number of times at focal point positions a to d corresponding to respective X-ray detectors.

When image pick-up by X-ray detectors 23 ends, X-ray detector driving unit 22 moves the four detectors simultaneously to the next position of image pick-up.

Figure 38A:
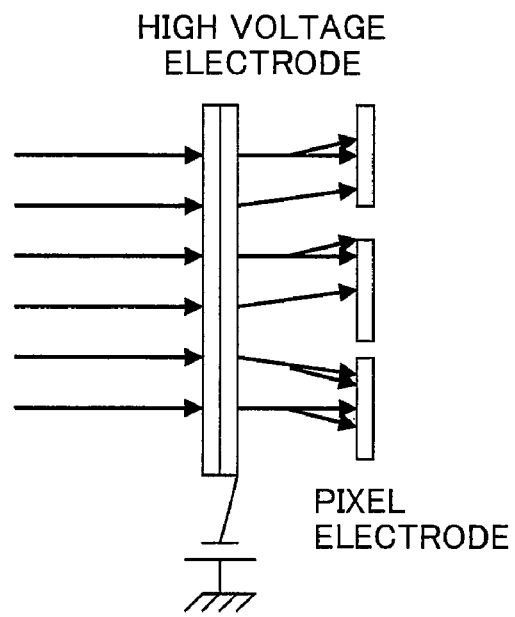
FIG. 38A is a schematic illustration showing a configuration of a detector used as X-ray detector 23.
Figure 38B:
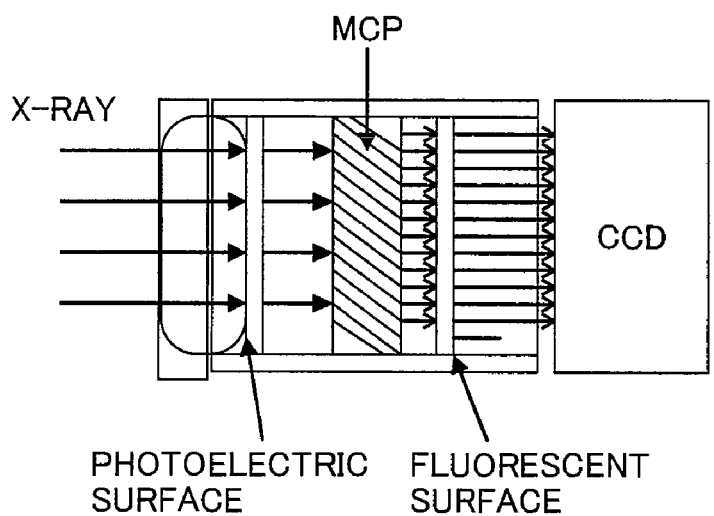
FIG. 38B is a schematic illustration showing a configuration of a detector used as X-ray detector 23.

FIGS. 38A and 38B are schematic illustrations showing configurations of detectors used as X-ray detector 23.

As X-ray detector 23, a charge accumulating type X-ray detector represented by a flat panel detector shown in FIG. 38A, or an image intensifier such as shown in FIG. 38B may be used. X-ray detector 23 records the position of incidence of X-ray by the function of converting incident X-ray to electrons by various methods and storing the same in a CCD (Charge Coupled Device) or a CMOS (Complementary Metal Oxide Semiconductor) device.

The time of charge accumulation is the exposure time of X-ray detector. Therefore, provided that the amount of X-ray irradiation in one exposure time is the same, the same output (image data) can be acquired no matter whether the X-ray is emitted continuously or the X-ray is emitted a number of times as pulses. Utilizing this characteristic, the method for inspection of X-ray inspecting apparatus 110 is realized.

Figure 39:
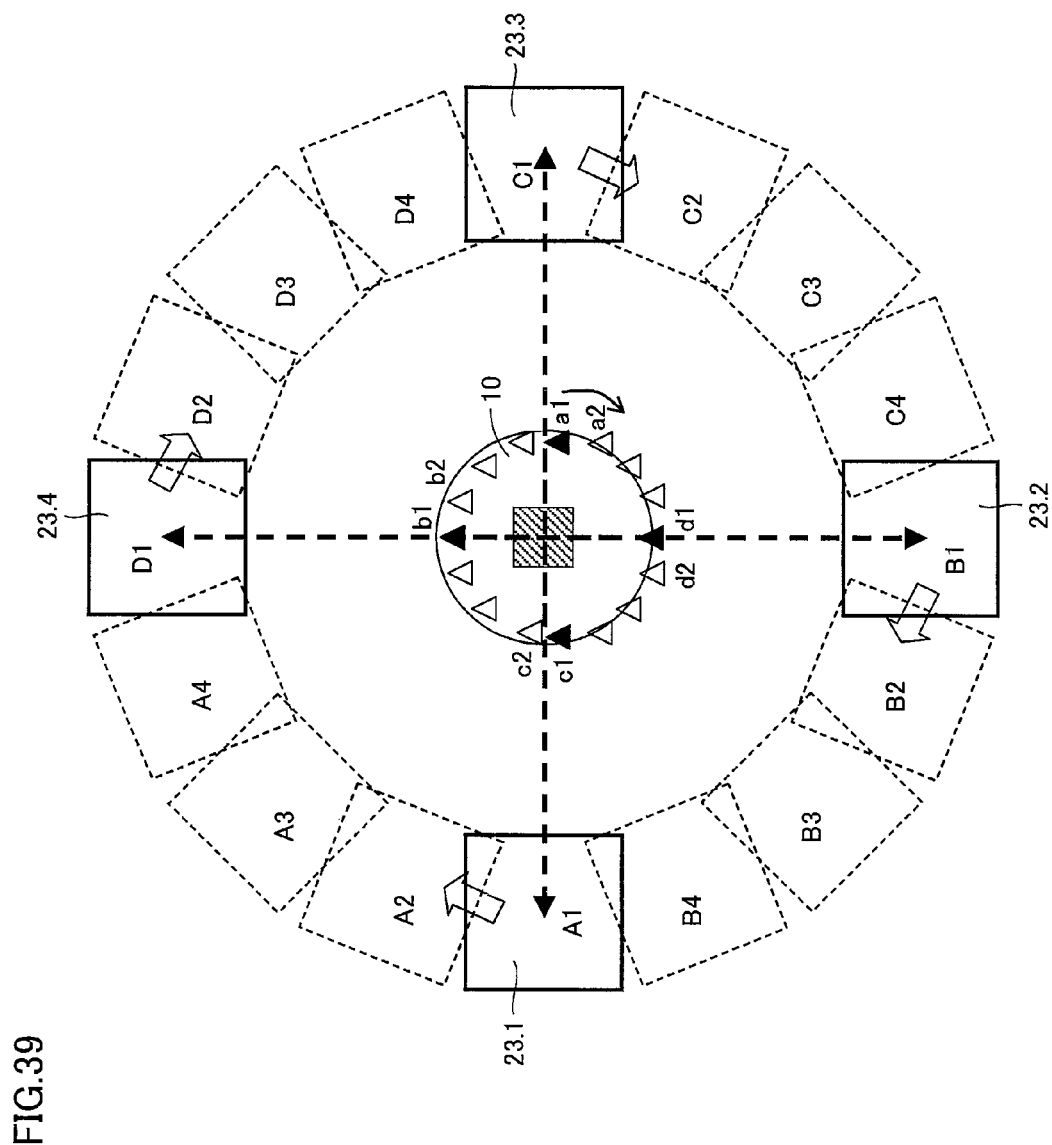
FIG. 39 is a top view showing movement trajectory of X-ray detector 23 and the scanning X-ray source, in the configuration of X-ray inspecting apparatus 110 shown in FIG. 37.

FIG. 39 is a top view showing a movement trajectory of X-ray detector 23 and the scanning X-ray source, in the configuration of X-ray inspecting apparatus 110 shown in FIG. 37.

The operation example shown in FIG. 39 corresponds to the configuration of FIG. 37 viewed from above, assuming that 16 X-ray fluoroscopic images are to be picked-up from different angles.

Shield 66 and X-ray detector driving mechanism 22 are not shown.

Referring to FIG. 39, positions to which X-ray detectors 23.1 to 23.4 move while picking-up images of one field of view will be denoted as A1 to A4, B1 to B4, C1 to C4 and D1 to D4, respectively. Further, X-ray focal point positions corresponding to the X-ray detector positions are denoted, for example by a1, a2, b1, b2, c, c2, d1, d2 and so on.

Since X-ray detector driving unit 22 is a circular sensor base, in FIG. 39, X-ray detectors 23 move always facing in the same direction with respect to the rotation axis of X-ray detector driving unit 22. If X-ray detector driving unit 22 is formed by two-axis robot arm, for example, and the iterative method or tomosynthesis is used as the method for reconstructing an image, the detectors may be kept in the same orientation with respect to the X-Y axes of the moving plane.

Figure 40:
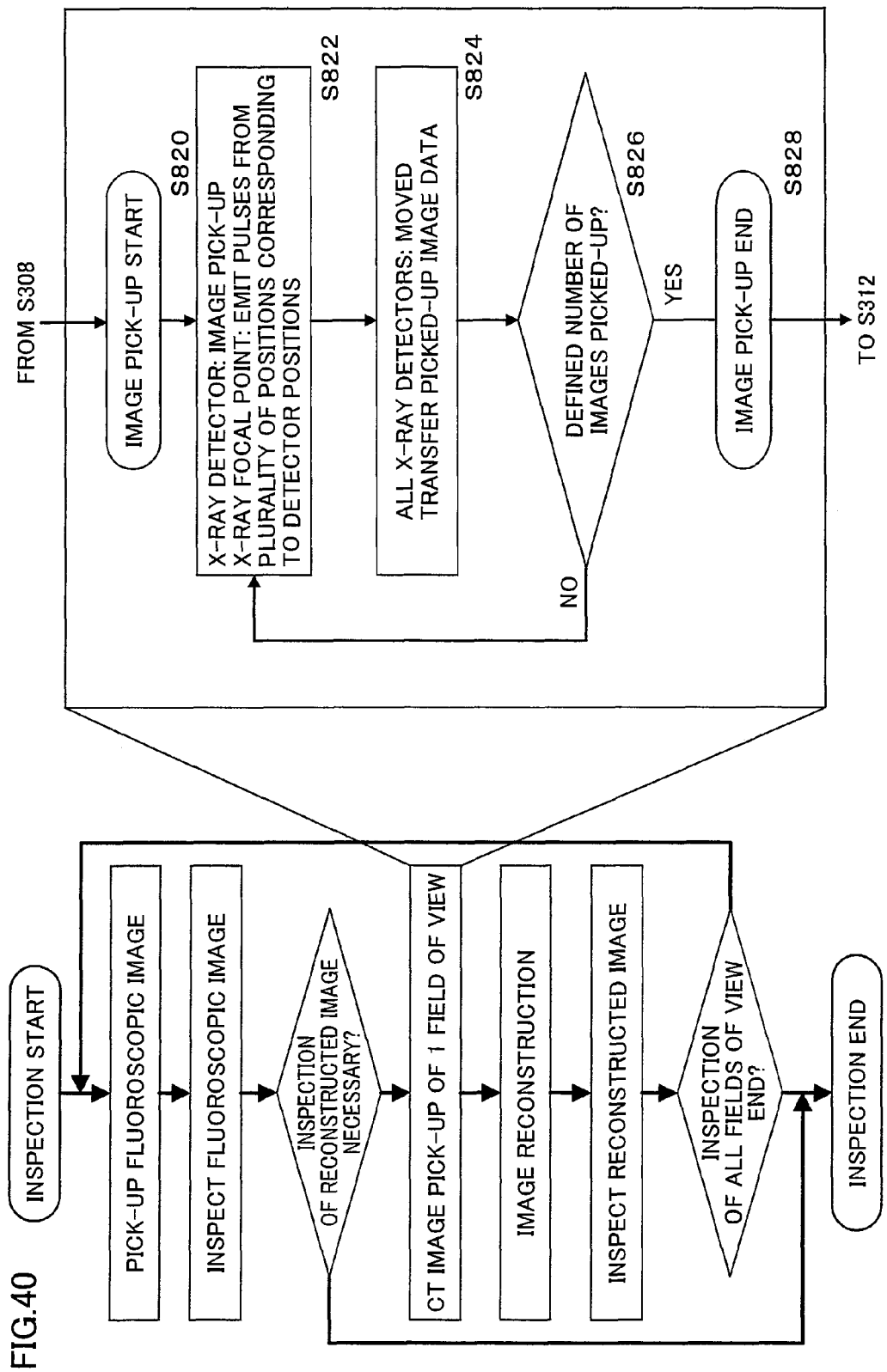
FIG. 40 is a flowchart of imaging of one field of view by the configuration of X-ray inspecting apparatus 110 shown in FIG. 37.

FIG. 40 is a flowchart of imaging of one field of view by the configuration of X-ray inspecting apparatus 110 shown in FIG. 37.

Before describing the operation shown in the flowchart, as a background, the following points should be noted.

1) In order to generate a reconstructed image, a plurality of X-ray fluoroscopic images picked-up from different angles are necessary.

2) The field of view is set on an axis of rotational movement of the X-ray detector.

3) Two or more (in the present example, four) X-ray detectors are used.

4) The X-ray detectors move on a circular orbit, with positional relation relative to each other kept unchanged.

5) At the time of image pick-up, X-ray detectors are stationary.

6) As the X-ray source, a scanning X-ray source capable of high speed movement of X-ray focal point is used.

7) On the X-ray source, shield 66 fixed in position is provided.

Referring to FIG. 40, if computing unit 70 determines that inspection by reconstructed image of a field of view is necessary and starts CT image pick-up of one field of view (S820), in accordance with an instruction from computing unit 70, all X-ray detectors 23.1 to 23.4 start exposure. At the same time, in accordance with an instruction from computing unit 70, the scanning X-ray source starts pulse emission from a plurality of portions corresponding to respective positions of X-ray detectors 23.1 to 23.4. When image pick-up (exposure) ends, computing unit 70 causes the X-ray source to stop emission (S822).

Thereafter, in accordance with an instruction from computing unit 70, all X-ray detectors 23.1 to 23.4 move on the circular orbit, with the rotation axis of sensor base 22.6 being the center. Here, X-ray detectors 23 transfer the just acquired image data through computing unit 70 to memory 90, and discharge charges, so that the detectors are ready for the next image pick-up (S824).

Thereafter, computing unit 70 determines whether the total number of picked-up images has reached the defined number, and repeats the process of steps S822 to 824 until the defined number is reached.

If it is determined by computing unit 70 that the defined number of images have been picked up, image pick-up operation ends, and the flow proceeds to the image reconstruction process (S312).

Figure 41:
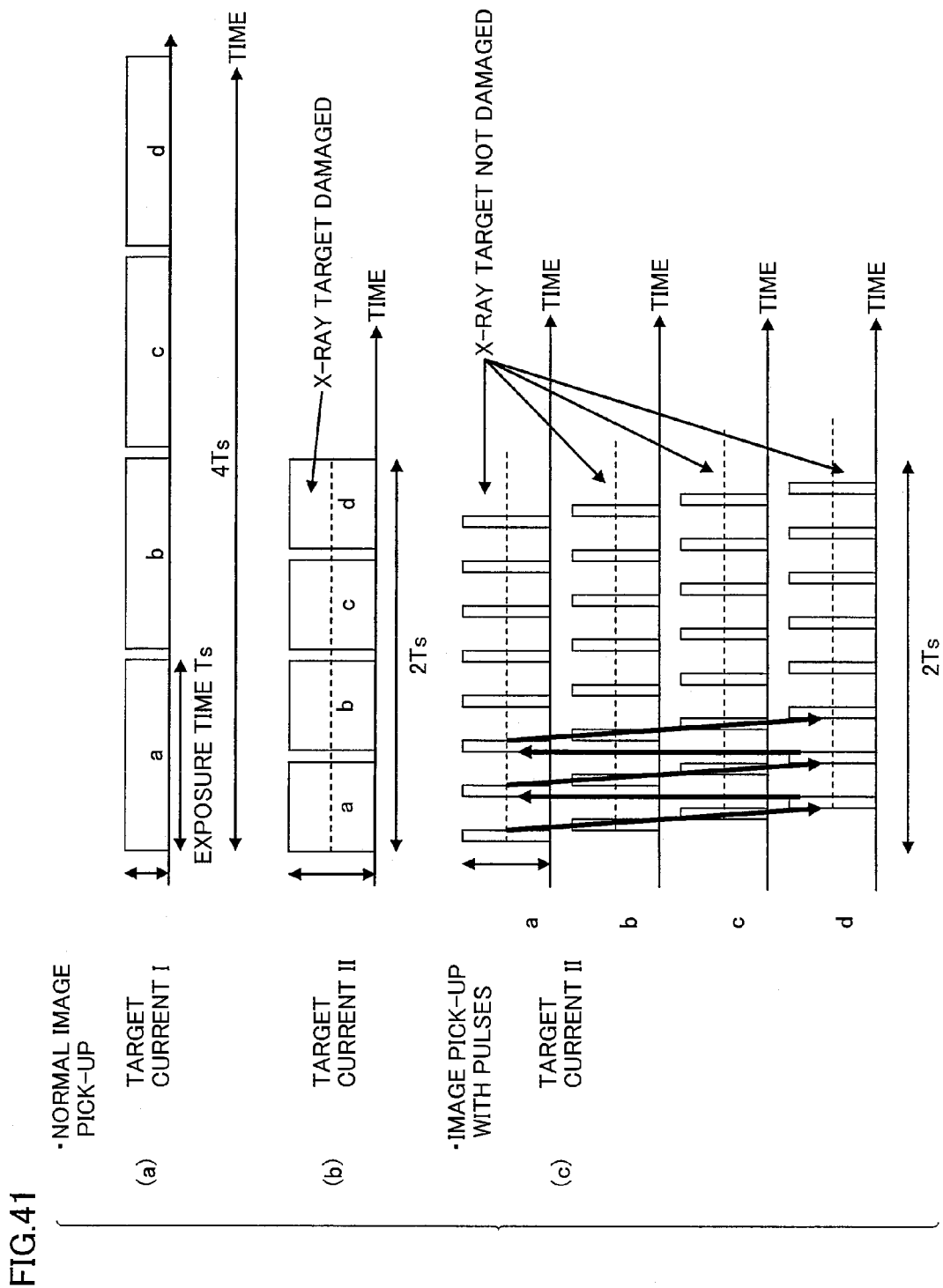
FIG. 41 is a timing chart representing operations of the scanning X-ray source when four X-ray detectors 23.1 to 23.4 are used.

FIG. 41 is a timing chart representing operations of the scanning X-ray source when four X-ray detectors 23.1 to 23.4 are used.

In the example shown in FIG. 41, the time necessary for moving the X-ray focal point position is negligibly shorter than the time necessary for exposure.

As shown in the timing chart (a), using the method for image pick-up described with reference to FIG. 34, the necessary exposure time for obtaining one fluoroscopic image having sufficient amount of information and the tolerable target current when equilibrium temperature is reached are represented by Ts and I, respectively.

As shown in the timing chart (b), the X-ray intensity is in proportion to the target current, and therefore, when the target current I is doubled, the time Ts necessary to acquire an image can be shortened to ½Ts. When a strong electron beams is used, however, a target would be damaged by temperature increase. Therefore, the use of the X-ray source in the manner as shown in the timing chart (b) is impossible. The target temperature increases when it is irradiated with the electron beam, and when irradiated for a prescribed time period, the temperature reaches the equilibrium temperature. The difficulty results from the fact that the temperature at this time is in proportion to the amount of current of the electron beam.

Therefore, as shown in the timing chart (c), the X-ray focal point position is moved at a significantly shorter time interval than the time for the target temperature to reach the equilibrium temperature. In FIG. 41, a means one of the focal point positions a1 to a4 corresponding to the current position of X-ray detector 23. The same applies to b, c and d. When the electron beam is applied as pulses as shown in the timing chart (c), image pick-up effectively utilizing a large current, which cannot be used in the manner of timing chart (b), becomes possible.

When the electron beam is driven in the manner as shown in the timing chart (c), if the target current at each X-ray focal point position at the moment of X-ray emission is 2I, the exposure time necessary for picking up the fluoroscopic image having the same amount of information as acquired by X-ray detectors 23.1 to 23.4 taking the time period of 4Ts in the example of timing chart (a) is 2Ts. The total exposure time of X-ray detectors 23.1 to 23.4 is the same as in the example of timing chart (b), while image pick-up is possible without causing any damage to the target.

Figure 42:
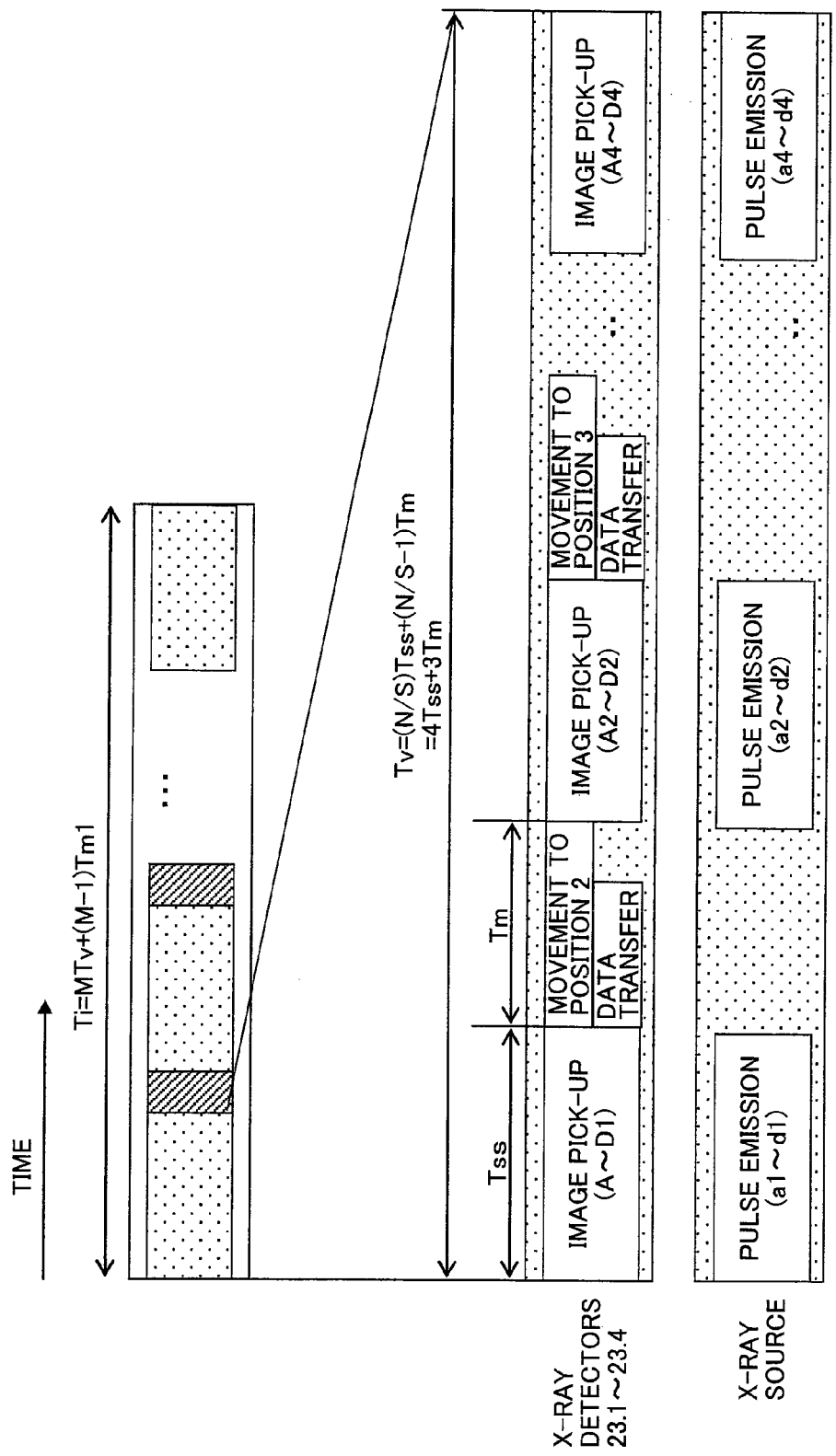
FIG. 42 is a timing chart of imaging of one field of view by X-ray inspecting apparatus 110 shown in FIG. 37.

FIG. 42 is a timing chart of imaging of one field of view by X-ray inspecting apparatus 110 shown in FIG. 37.

As shown in FIG. 42, the time for picking up one field of view can be represented by Equation (23). The number of images N to be picked up is an integer multiple of the number of detectors.

$$Tv=(N/S)Tss+(N/S-1)Tss \quad (23).$$

The signs represent as follows.

N: the number of picked-up images (integer multiple of the number of X-ray detectors)

S: the number of X-ray detectors

Tv: time necessary for picking-up one field of view

Tm: time for moving the moving mechanism (stage, X-ray detector)

Tss: time for image pick-up (exposure time of X-ray detector) for simultaneous exposures by S X-ray detectors.

Though the number N of picked-up images is set to the integer multiple of the number of X-ray detectors for simplicity of description, it is not necessarily limited to the integer multiple.

Assuming that the number of fluoroscopic images to be picked up necessary for reconstruction of the image is 16, and when the image pick-up method described with reference to FIGS. 37 to 41 is used, the time necessary for acquiring the necessary number of images, that is, 16 images, for reconstruction is 4Tss+3Tm. As to Tss, since the X-ray intensity can be increased, the relation of 4Ts>Tss holds. Therefore, as compared with the example using four detectors described with reference to FIG. 34, which took (16Ts+3Tm), the time for image pick-up can be reduced.

Figure 43A:
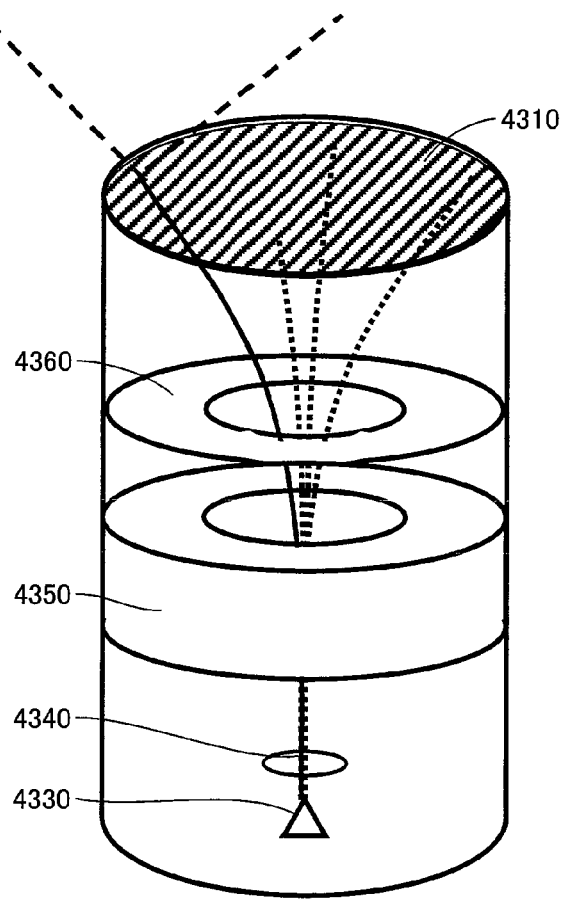
FIG. 43A is a schematic illustration showing a configuration of a scanning X-ray source.
Figure 43B:
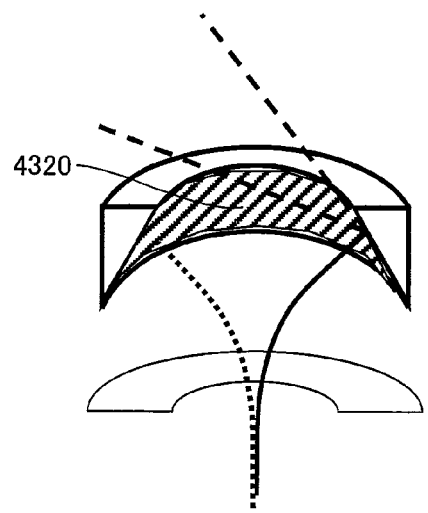
FIG. 43B is a schematic illustration showing a configuration of a scanning X-ray source.

FIGS. 43A and 43B are schematic illustrations showing configurations of the scanning X-ray source.

FIG. 43A shows an exemplary internal configuration of an X-ray source for transmission type target, and FIG. 43B shows an example of a reflection type target. As will be described in the following, such a configuration of a scanning X-ray source enables the operation of Embodiment 4.

In the scanning X-ray source, an electron beam emitted from an electron gun 4330 passes through a grid 4340, and thereafter, spot diameter of the electron beam is narrowed by a convergence lens 4350. Further, by an externally controlled deflector 4360, the electron beam is deflected in X direction and/or Y direction, and impinges on an arbitrary position on the X-ray target (electron beams impinging on targets 4310 and 4320 are generally referred to as target current).

Here, 99% of kinetic energy of the electron beam impinging on the X-ray target turn to heat, and approximately 1% serves as braking X-ray.

As described above, X-ray targets include transmission type (FIG. 43A) and reflection type (FIG. 43B) targets. The transmission type is typically formed by depositing tungsten on beryllium or aluminum.

In order to prevent exposure while the X-ray focal point is moving, the electron beam may be stopped when the position (X-ray focal point position) of the electron beam is changed. By way of example, the electron beam is turned ON/OFF by controlling a grid voltage of the electron gun.

Embodiment 5

In the foregoing, it has been described that when the field of view of an object of inspection is to be changed, the object of inspection is moved by the inspection object position control mechanism.

When a scanning X-ray source is used, however, it is possible to change the field of view without moving the object of inspection to a certain extent, by adjusting relative positional relation between X-ray focal point position 17 and X-ray detector 23.

In that case, the center of trajectories of focal points on the X-ray target when a plurality of images necessary for image reconstruction are picked up in one field of view comes off from the center of the target. Therefore, such CT image pick-up will be referred to as "eccentric CT image pick-up" in the present specification.

The X-ray inspecting apparatus in accordance with Embodiment 5 has a configuration that combines the eccentric CT image pick-up and the X-ray detector driving unit 22 as described in the modification of Embodiment 1.

Specifically, the inspection area is typically wider than the area of CT image reconstruction area, and therefore, it is necessary to divide the inspection area into a plurality of fields of view (reconstruction areas of one CT image pick-up). Generally, movement from one field of view to another is realized by mechanically moving the object of inspection using, for example, an X-Y stage. In the X-ray inspecting apparatus in accordance with Embodiment 5, the movement from one field of view to another is realized in a motionless manner by electronic movement of the X-ray focal point position, to increase the system speed.

By moving the X-ray focal point position through electric control using the scanning X-ray source, it becomes possible to move the position of image pick-up at high speed, eliminating mechanical movement. By arranging a plurality of X-ray detectors 23 at fixed positions in advance, the time for mechanical movement of X-ray detectors 23 is reduced. Since the movement of field of view is realized only by the movement of X-ray focal point position, the movement of field of view can be done at high speed.

Figure 44:
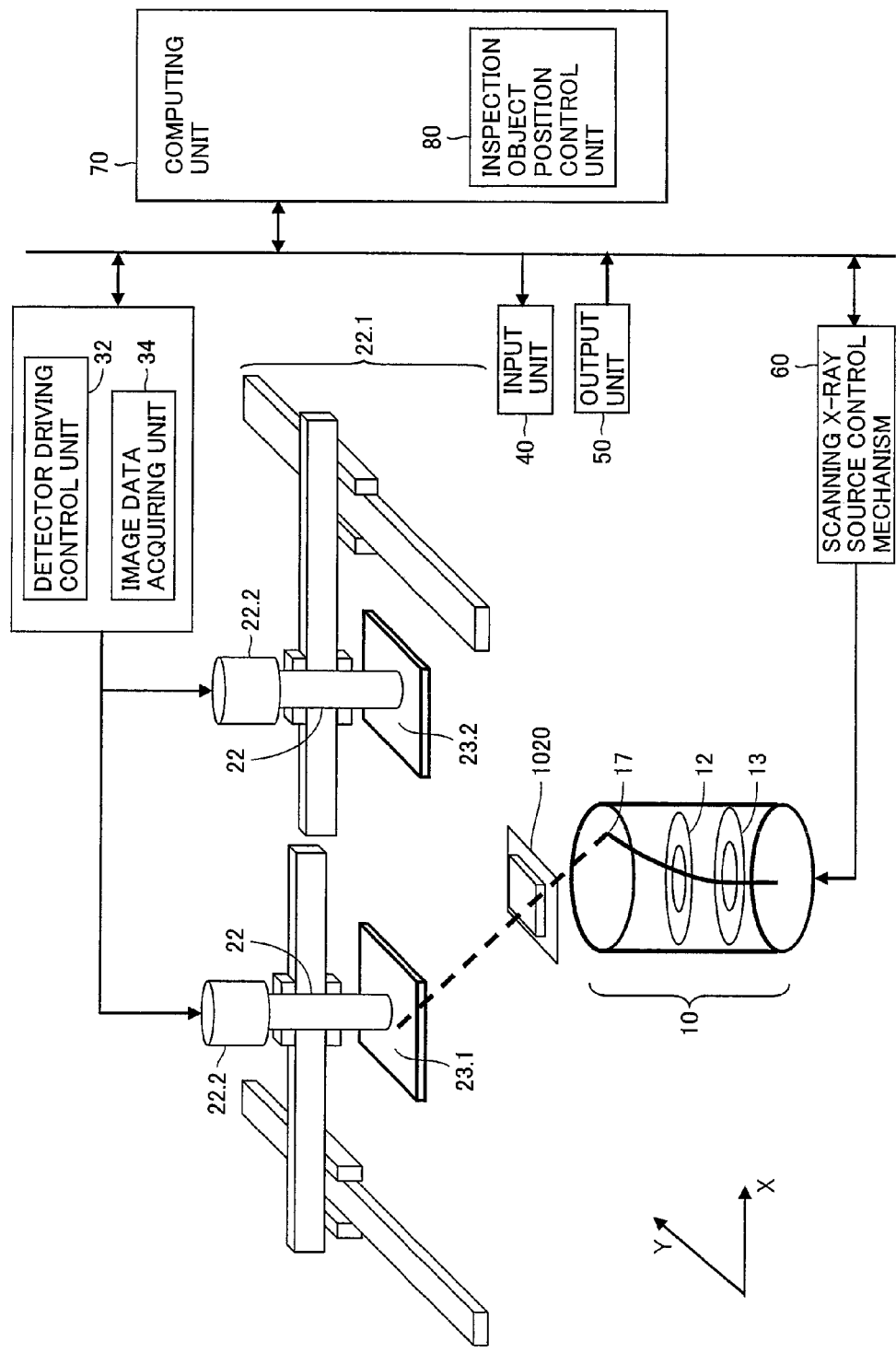
FIG. 44 is a block diagram showing a configuration of an X-ray inspecting apparatus 120 in accordance with Embodiment 5.

FIG. 44 is a block diagram showing a configuration of an X-ray inspecting apparatus 120 in accordance with Embodiment 5 as such.

It is noted that the configuration of X-ray inspecting apparatus 120 is the same as that of X-ray inspecting apparatus 100 described with reference to FIG. 10, except for the control related to the movement of X-ray detector 23 and the movement of X-ray focal point position 17 as will be described in the following. Therefore, description related to the configuration will not be repeated. As will be described in the following, the configuration for rotating X-ray detector 23 is unnecessary in the present embodiment, and X-ray detector 23 moves in the translational manner in the X-Y plane.

Figure 45:
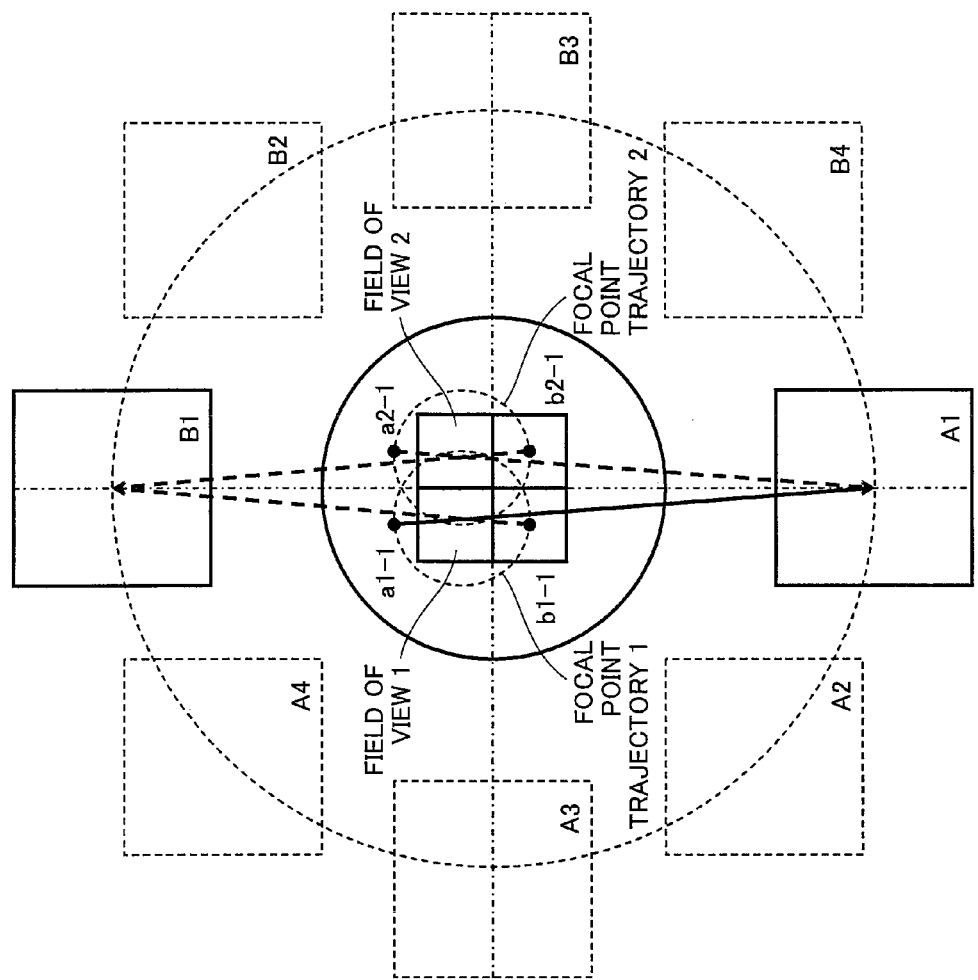
FIG. 45 shows an example of operation of an imaging system using a translational X-ray detector.

FIG. 45 shows an example of operation of an imaging system using a translational X-ray detector.

FIG. 45 shows an example in which four fields of view are reconstructed without mechanical movement of X-ray detector 23 or the object of inspection. FIG. 45 shows the configuration of FIG. 44 viewed from above, assuming image pick-up of 8 fluoroscopic images picked up from equal angles.

The operation example of FIG. 45 is suitable for the reconstruction method such as the iterative method or tomosynthesis. The reason for this is that by the iterative method or tomosynthesis, reconstruction is possible regardless of the direction of X-ray detector. In such an operation, it is unnecessary to rotate the X-ray detector. Therefore, the X-ray detector driving mechanism can be further simplified, and the speed of operation and maintainability of the mechanism can be improved.

To enable such an operation as shown in FIG. 45, it is necessary that the ranges in which X-ray detector 23.1 and X-ray detector 23.2 operate independently from each other are separated.

In FIG. 45, positions A1 and B1 represent initial positions of X-ray detector 23.1 and X-ray detector 23.2, respectively. Positions A1 to A4 and B1 to B4 are positions of X-ray detector 23.1 and X-ray detector 23.2 for acquiring the fluoroscopic images necessary for image reconstruction, respectively.

In the example of FIG. 45, X-ray detector 23.1 and X-ray detector 23.2 move at a constant distance, with the origin of imaging system being the center. As a result, when the imaging system is viewed from above, the detectors each have a semicircular trajectory. The movement of X-ray detectors, however, is not limited to a circular orbit.

In FIG. 45, focal point positions a1-1, a2-1, b1-1 and b2-1 are focal point positions on the X-ray target. Focal point position a1-1 represents a focal point corresponding to the position A1 of X-ray detector when an image of field of view 1 is picked up, and focal point position a2-1 represents a focal point corresponding to the position A1 of X-ray detector when an image of field of view 2 is picked up. When images of field of view 1 are picked up, corresponding to the positions A1 to A4 of the X-ray detector, the focal point is successively positioned on a circular orbit as represented by a dotted line on the target, from the focal point position a1-1 to a1-2, a1-3 and a1-4 (not shown). Similarly, corresponding to the positions A1 to A4 of the X-ray detector, the focal point is successively positioned on a circular orbit as represented by a dotted line on the target, from the focal point position a2-1 to a2-2, a2-3 and a2-4 (not shown). Focal point position b1-1 represents a focal point corresponding to the position B1 of X-ray detector when an image of field of view 1 is picked up, and focal point position b2-1 represents a focal point corresponding to the position B1 of X-ray detector when an image of field of view 2 is picked up. Similar to focal point positions a1-1 and a2-1, focal point positions b1-1 and b2-1 are also moved to other focal point positions on a circular orbit as represented by a dotted line on the target, corresponding to the positions B1 to B4 of the X-ray detector.

The overall flow of inspection involving movement of X-ray detector 23 and X-ray focal point position in the example of FIG. 45 is the same as that of FIG. 12.

It is noted, however, that in X-ray inspecting apparatus 120 of Embodiment 5, the time of movement of the field of view is reduced for the second and later fields of view. The reason for this is that simultaneously with the start of the last image pick-up for one field of view, the other X-ray detector is moved to the position of image pick-up for the next field of view. Here, in order to eliminate the necessity of moving the stage, only the X-ray focal point position is changed. Specifically, as shown in the operation example of FIG. 45, images are picked up with the angle of image pick-up changed. It is noted that image pick-up at not-equal angles as such possibly results in degradation of a reconstructed image. The degradation, however, can be reduced by using the iterative method.

Figure 46:
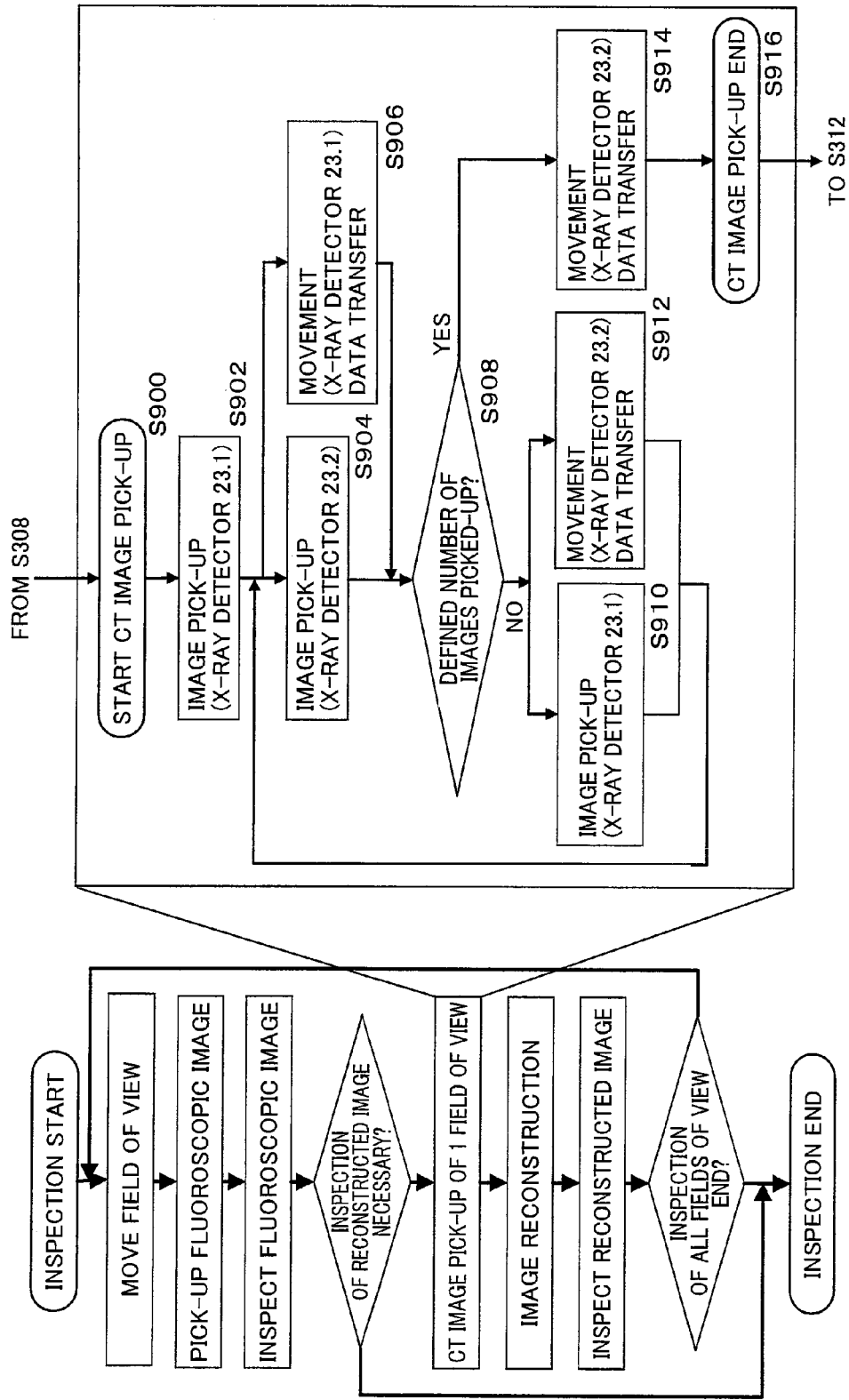
FIG. 46 is a flowchart of the inspection of one field of view by the imaging system shown in FIGS. 44 and 45.

FIG. 46 is a flowchart of the inspection of one field of view by the imaging system shown in FIGS. 44 and 45.

Figure 47:
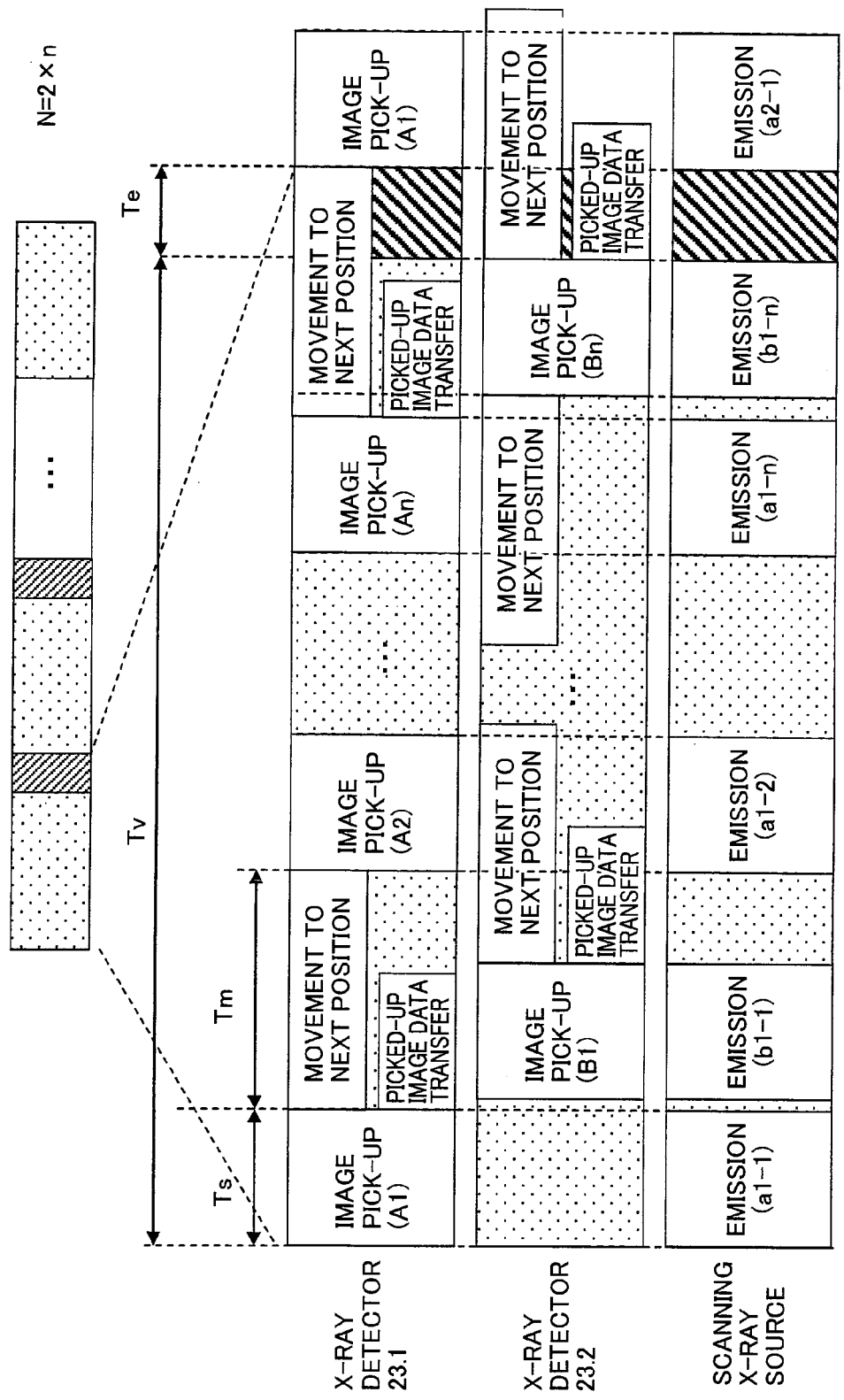
FIG. 47 is an inspection timing chart of the inspection of one field of view by the imaging system shown in FIGS. 44 and 45.

FIG. 47 is an inspection timing chart of the inspection of one field of view by the imaging system shown in FIGS. 44 and 45.

In the following, the inspection process of one field of view by X-ray inspecting apparatus 120 in accordance with Embodiment 5 will be described with reference to FIGS. 46 and 47.

It is assumed that before the start of CT image pick-up, the field of view (object of inspection) and X-ray detectors 23 are at the prescribed initial positions A1 and B1.

When CT image pick-up of one field of view starts (S900), first, computing unit 70 causes X-ray detector 23.1 to pick up an image of the object of inspection (S902). Specifically, computing unit 70 moves the X-ray focal point to the position a1-1 corresponding to X-ray detector 23.1 for image pick-up. Here, the operation of moving X-ray focal point is done electronically at very high speed, so that the required time therefor is negligible as compared with the exposure time or the time of mechanical movement. The time of image pick-up (detector exposure time) may be set in advance, or a desired time may be set by the user based on visual observation. The picked-up image data of the object of inspection is acquired by emitting X-ray from the X-ray source and thereby exposing the X-ray detector. The exposure time may be determined in advance considering the size of the object of inspection or the intensity of X-ray emitted from the X-ray source.

Next, computing unit 70 causes the image data acquired by X-ray detector 23.1 to be transferred to computing unit 70 (S906). The image data is transferred to memory 90 used by computing unit 70, by image acquisition control mechanism 30.

In parallel with the data transfer, computing unit 70 emits X-ray at focal point position b1-1 and the image of object of inspection is picked-up by X-ray detector 23.2 (S904) and, at the same time, X-ray detector 23.1 is moved to the next position of image pick-up (S906). Image pick-up by X-ray detector 23.2 is carried out in the similar manner as X-ray detector 23.1 described above. Here, to enable image pick-up by X-ray detector 23.2, X-ray focal point 17 must be moved. This movement, however, is done at a relatively high speed as compared with other operations. The next position (A2) of image pick-up by X-ray detector 23.1 must be determined before the inspection. Generally, the positions of image pick-up by the X-ray detectors can be determined when the number of images to be picked-up is determined from design information such as the CAD data.

If the defined number of images to be picked-up for one field of view is not yet reached (S910), computing unit 70 transfers the image data acquired by X-ray detector 23.2 to computing unit 70 (S912). In parallel with the data transfer, computing unit 70 emits X-ray at focal point position a1-2 and the image of object of inspection is picked-up by X-ray detector 23.1 (S910) and, at the same time, X-ray detector 23.2 is moved to the next position of image pick-up (S912). Here again, the next position of image pick-up (B2) must be determined before the inspection.

Thereafter, in a similar manner, the image pick-up by X-ray detector 23.2 and the transfer of the picked-up image data from X-ray detector 23.1 or the movement of X-ray detector 23.1 to the next position of image pick-up are performed in parallel, or the image pick-up by X-ray detector 23.1 and the transfer of the picked-up image data from X-ray detector 23.2 or the movement of X-ray detector 23.2 to the next position of the image pick-up are performed in parallel, repeatedly until the number of picked-up images reaches the defined number. In this regard, the operation is basically the same as the operation of Embodiment 1 described with reference to FIG. 14.

When the image pick-up for the defined number ends (S908), computing unit 70 transfers the picked-up image data from X-ray detector 23.2 and moves X-ray detector 23.2 to the next position of image pick-up (S914), and thus, the process of the image pick-up for one field of view ends (S916). Then, the process proceeds to S312.

The estimated time required for the CT image pick-up for one field of view in the example of FIG. 47 is as follows.

$$Tv=(N/S-1)Tm+STs.$$

The definitions of the times for respective processes are as follows.

Tm: time for moving the moving mechanism (X-ray detector)

Ts: time for image pick-up (exposure time of X-ray detector)

The time Tv of CT image pick-up for one field of view using S (for example, two) X-ray detectors 23 is the sum of N times the image pick-up time and N/S times the necessary time of the mechanical movement. It is noted, however, that Tv changes depending on the time required by each process step. In the following, calculation will be done assuming $Tm > Ts \gg Tf$ (time of moving X-ray focal point) (that the speed of movement of X-ray focal point is sufficiently high to be negligible as compared with other processes), considering general time of image pick-up.

Description will be made assuming that there are two X-ray detectors.

First, for the image pick-up by X-ray detector 23.1, it takes time Ts. Next, for moving the X-ray focal point, it takes time Tf, while X-ray detector 23.1 is moved at the same time to the next position A2 of the image pick-up. Since X-ray detector 23.2 has already been positioned at the prescribed position, the image pick-up can be done without any time consumed for moving. Thus, the image pick-up takes Ts. After the image pick-up by X-ray detector 23.2, X-ray detector 23.2 is moved. Next, the image pick-up is done by X-ray detector 23.1. By that time, however, the movement is not yet finished. The movement ends after Ts+Tm from the start of the image pick-up, and then, at position A2, the image pick-up is done by X-ray detector 23.1. Thereafter, the image pick-up is done by X-ray detector 23.2. Since the movement is not yet finished, the image pick-up starts after Ts+Tm. Since the first image pick-up by X-ray detector 23.2 started after Ts, one cycle of image pick-up takes Tm. There are (N/2−1) cycles each taking time Tm, and by adding the time Ts for the first image pick-up (A1) by X-ray detector 23.1, the time Tf of moving the X-ray focal point and the last image pick-up by X-ray detector 23.2, the time for CT image pick-up for one field of view is determined, which is given by Equation (24).

$$Tv=(N/2-1)Tm+2Ts \qquad (24).$$

The time for movement to the next field of view corresponds to the time for X-ray detector 23.1 to move to the image pick-up position of the next field of view minus the time Ts of image pick-up by X-ray detector 23.2. Thus, it is given by Equation (25).

$$Te=Tm-Ts \qquad (25).$$

Figure 48:
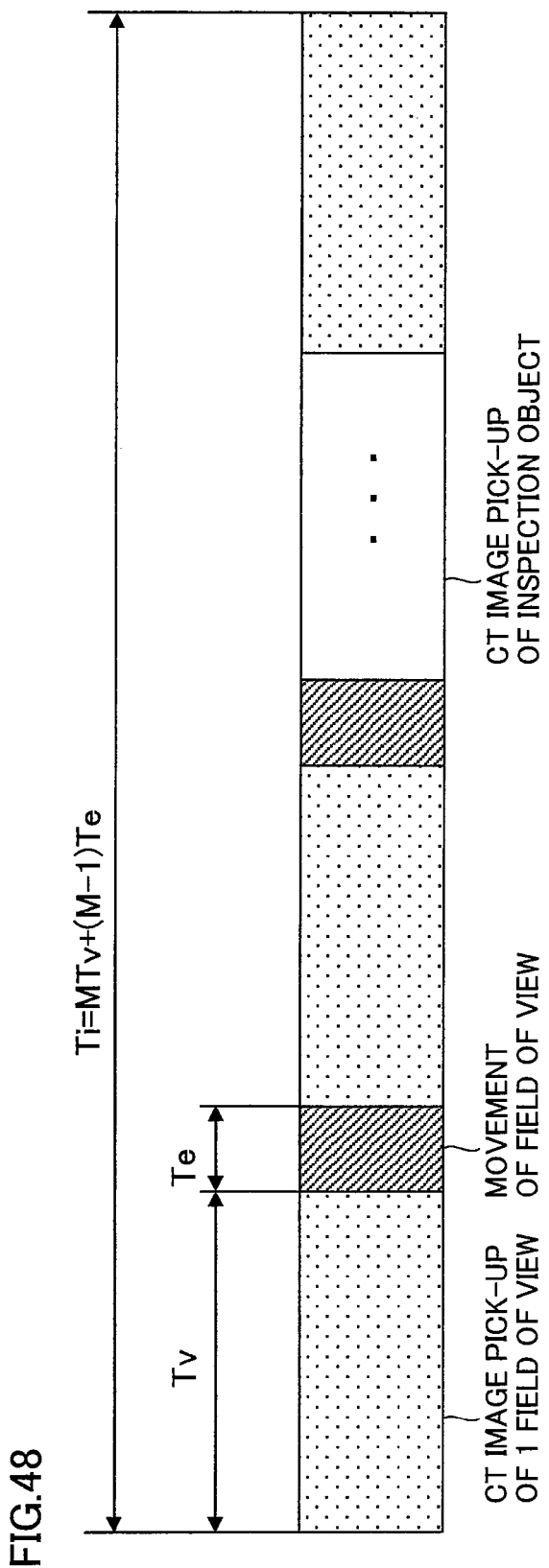
FIG. 48 is an inspection timing chart of the inspection of the overall inspection by the imaging system shown in FIGS. 44 and 45.

FIG. 48 is an inspection timing chart of the inspection of the overall inspection by the imaging system shown in FIGS. 44 and 45.

In FIG. 48, it is assumed that the object of inspection is divided into M (for example, four) fields of view, and N images are picked-up as CT images. Definitions of signs will be given below.

The CT image pick-up time Ti of the entire object of inspection is a sum of the time for image pick-up of M fields of view and the time of movement of field of view of (M−1) times, and hence, it is given by Equation (26) below.

$$Ti=MTv+(M-1)Te \qquad (26).$$

The signs represent as follows.

Ti: time necessary for picking up images of the entire object of inspection

Tv: time necessary for picking-up one field of view

Te: time necessary for moving field of view

In X-ray inspecting apparatus 120, the time Te for moving the field of view is substantially the difference between the time of movement Tm and the time of image pick-up Ts, and therefore, the time of movement can be significantly reduced.

Modification of Embodiment 5

Figure 49:
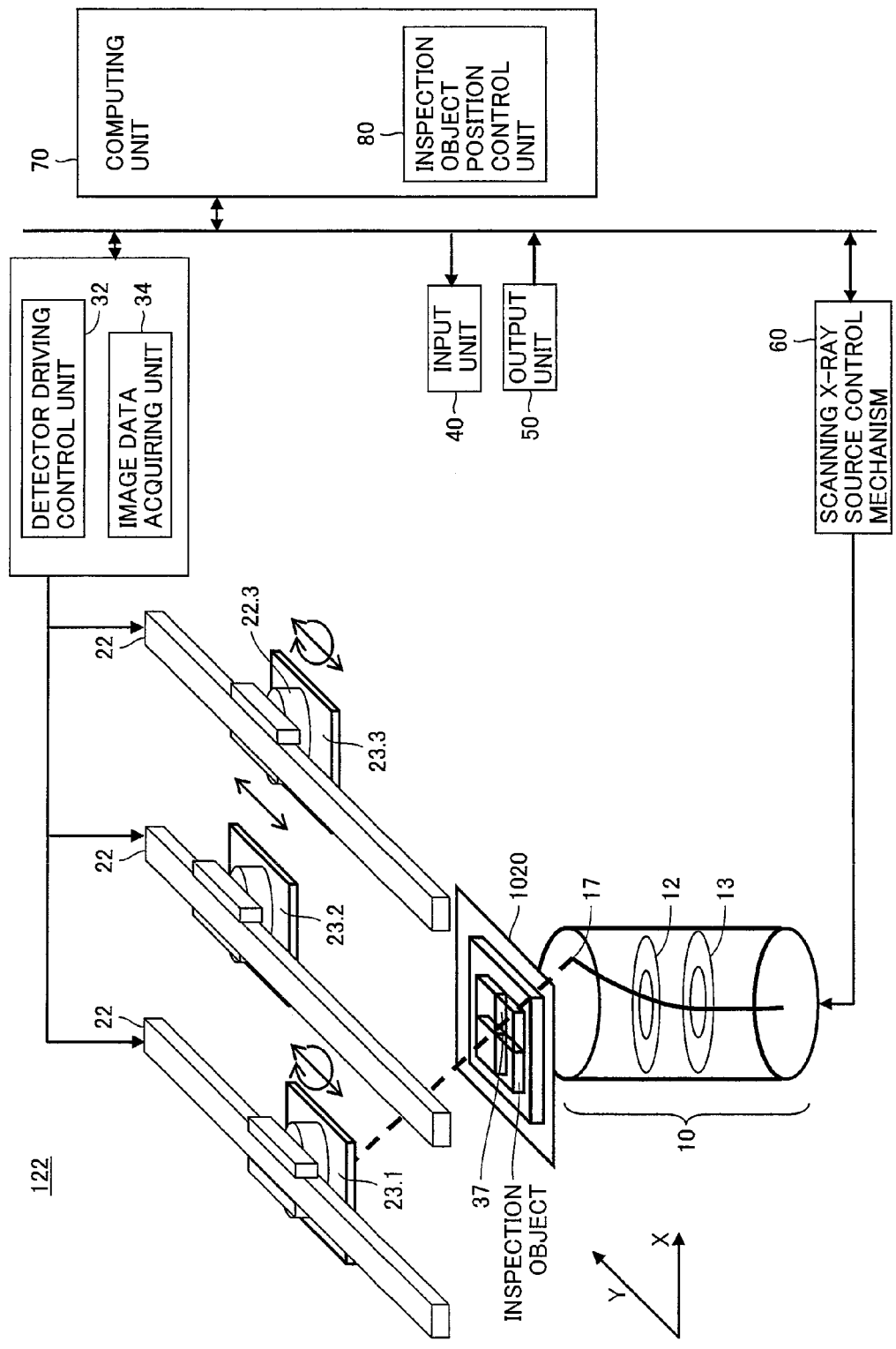
FIG. 49 illustrates a configuration of an X-ray inspecting apparatus 122 in accordance with a modification of Embodiment 5.

FIG. 49 illustrates a configuration of an X-ray inspecting apparatus 122 in accordance with a modification of Embodiment 5.

X-ray inspecting apparatus 122 uses a linear X-ray detector and a scanning X-ray source as X-ray source 10.

It is noted that the configuration of X-ray inspecting apparatus 122 is the same as that of X-ray inspecting apparatus 102 described with reference to FIG. 15, except for the control related to the movement of X-ray detector 23 and the movement of X-ray focal point position 17 as will be described in the following. Therefore, description related to the configuration will not be repeated. As will be described in the following, the configuration for rotating X-ray detector 23 is unnecessary in the present modification of the embodiment, and X-ray detector 23 moves in a translational manner in the X-Y plane.

Figure 50:
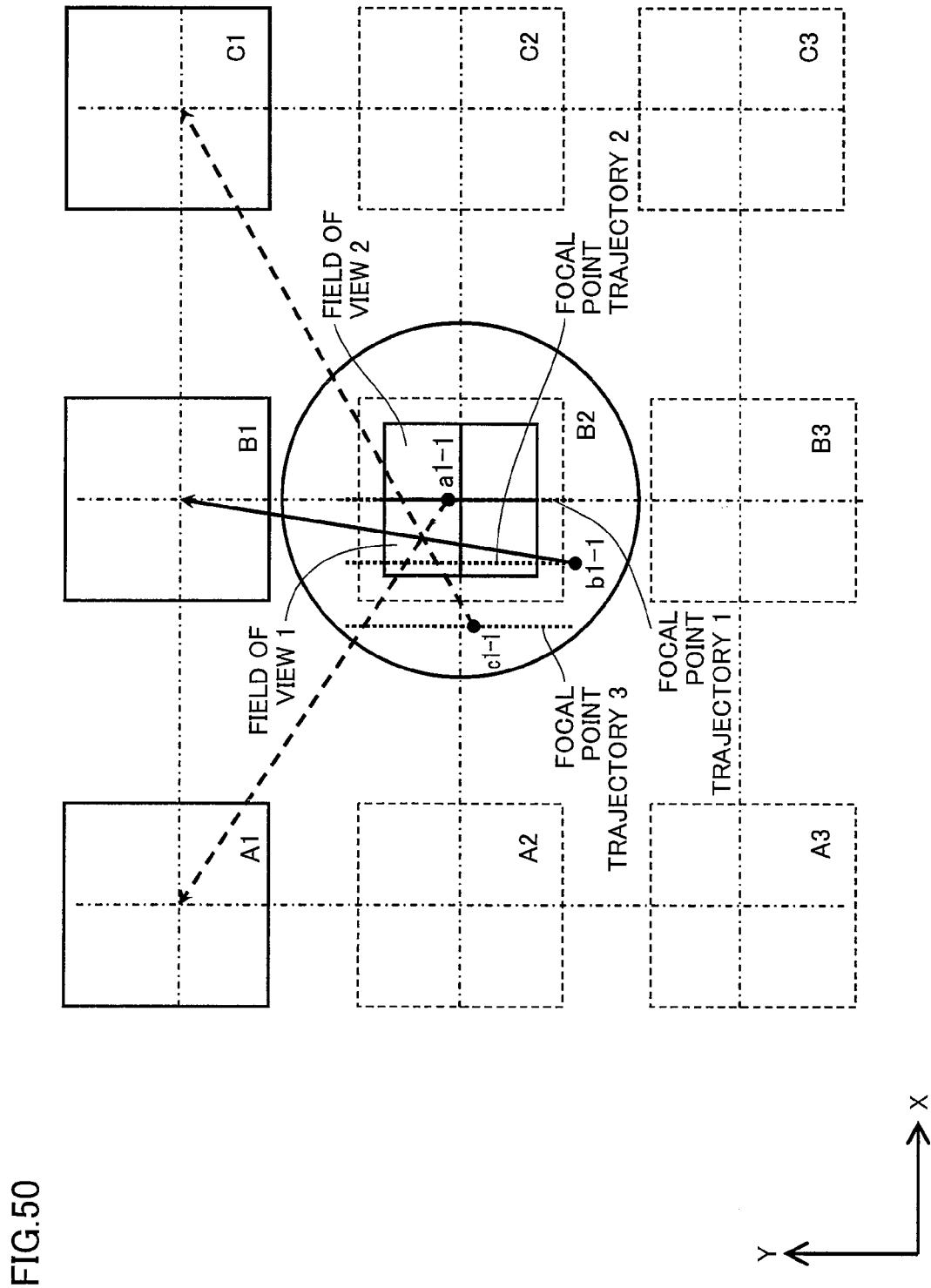
FIG. 50 shows an example of operation of an imaging system using a translational X-ray detector of X-ray inspecting apparatus 122.

FIG. 50 shows an example of operation of an imaging system using a translational X-ray detector of X-ray inspecting apparatus 122.

FIG. 50 shows a configuration of FIG. 49 viewed from above, assuming that nine X-ray fluoroscopic images are to be picked up at different distances of equal interval.

Positions A1 to A3, B1 to B3 and C1 to C3 of X-ray detectors represent positions of X-ray detectors 23.1, 23.2 and 23.3 for acquiring fluoroscopic images necessary for image reconstruction. Of the characters representing positions, the numerals represent the order of image pick-up. The image pick-up starts first at A1, and ends at A3. The order of the image pick-up, however, may be different from above.

The trajectory of the focal points on the target corresponding to positions A1 to A3 of X-ray detector is a line such as focal point trajectory 1; the trajectory of the focal points on the target corresponding to positions B1 to B3 of X-ray detector is a line such as focal point trajectory 2; and trajectory of the focal points on the target corresponding to positions C1 to C3 of X-ray detector is a line such as focal point trajectory 3.

Such an arrangement of X-ray detectors is also suitable for the reconstruction method such as the iterative method or the tomosynthesis. In such an operation, it is unnecessary to rotate the X-ray detector 23. Therefore, X-ray detector driving mechanism 22 can further be simplified, and the speed of the operation and the maintainability of the mechanism can be improved.

Figure 51:
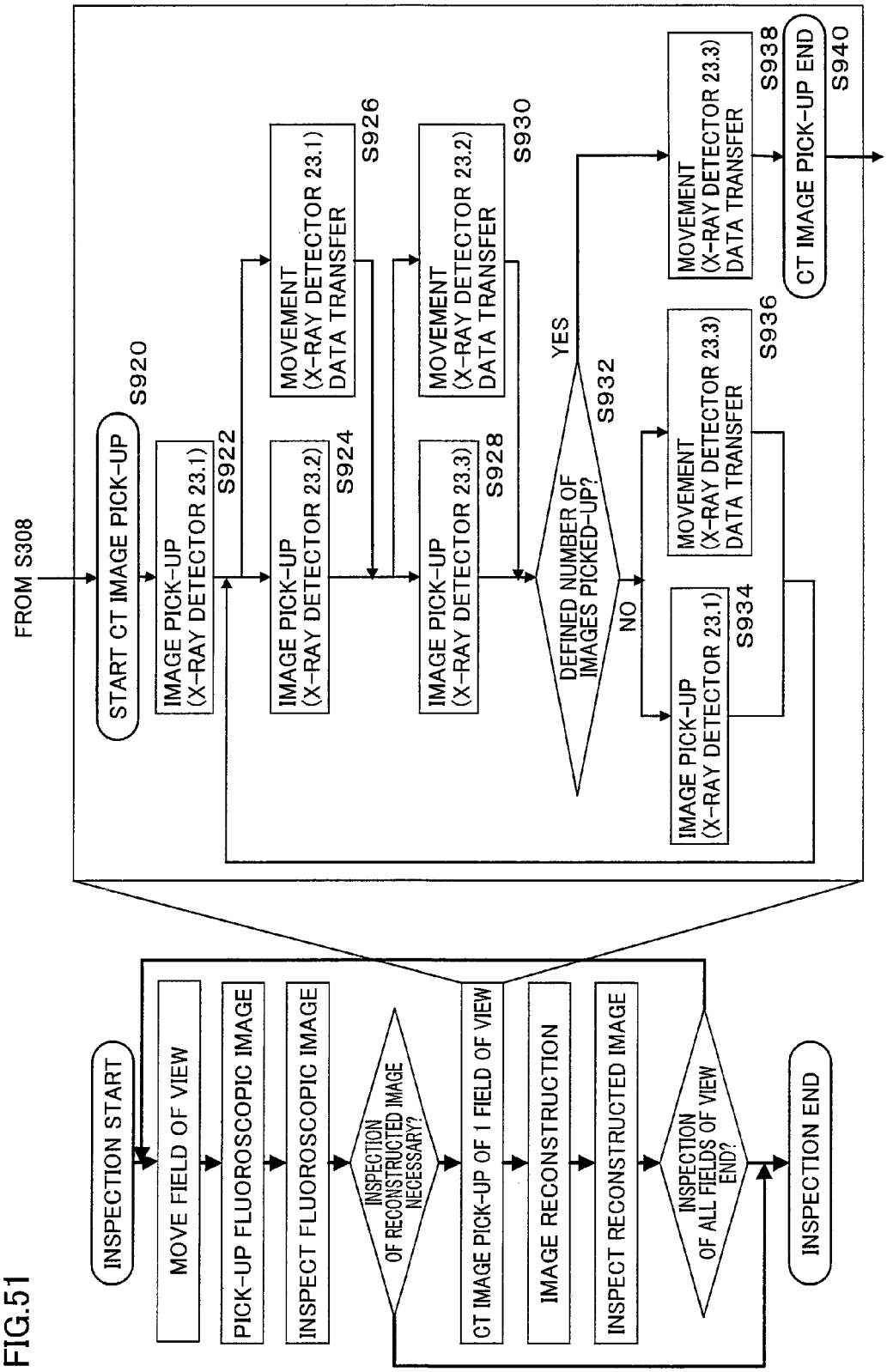
FIG. 51 is a flowchart of the inspection of one field of view by the imaging system using a linear detector shown in FIGS. 49 and 50.

FIG. 51 is a flowchart of the inspection of one field of view by the imaging system using the linear detector shown in FIGS. 49 and 50.

Figure 52:
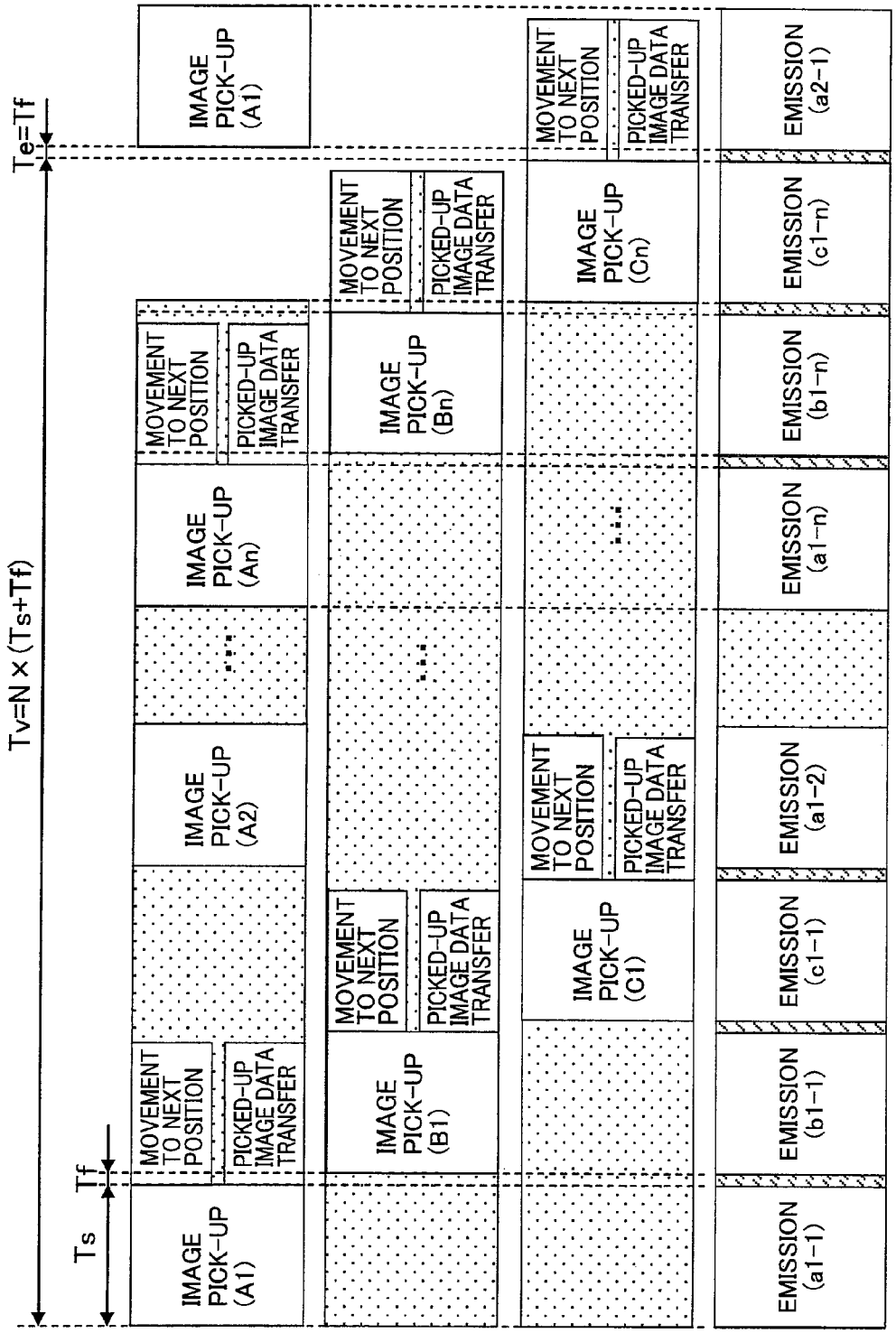
FIG. 52 is an inspection timing chart of the inspection of one field of view by the imaging system shown in FIGS. 49 and 50.

FIG. 52 is an inspection timing chart of the inspection of one field of view by the imaging system shown in FIGS. 49 and 50.

In the following, the inspection process of one field of view by X-ray inspecting apparatus 122 in accordance with the modification of Embodiment 5 will be described with reference to FIGS. 51 and 52.

It is assumed that before the start of the CT image pick-up, the field of view (object of inspection) and X-ray detectors 23 are at the prescribed initial positions A1, B1 and C1.

When the CT image pick-up of one field of view starts (S920), first, computing unit 70 causes X-ray detector 23.1 to pick up an image of the object of inspection (S922). Specifically, computing unit 70 moves the X-ray focal point to the position a1-1 corresponding to X-ray detector 23.1 for the image pick-up. Here, the operation of moving X-ray focal point is done electronically at very high speed, so that the required time therefor is negligible as compared with the exposure time or the time of the mechanical movement. The time of the image pick-up (detector exposure time) may be set in advance, or a desired time may be set by the user based on visual observation. The picked-up image data of the object of inspection is acquired by emitting X-ray from the X-ray source and thereby exposing the X-ray detector. The exposure time may be determined in advance considering the size of the object of inspection or the intensity of X-ray emitted from the X-ray source.

Next, computing unit 70 causes the image data acquired by X-ray detector 23.1 to be transferred to computing unit 70 (S926). The image data is transferred to memory 90 used by computing unit 70, by image acquisition control mechanism 30.

In parallel with the data transfer, computing unit 70 emits X-ray at focal point position b1-1 and the image of object of inspection is picked-up by X-ray detector 23.2 (S924) and, at the same time, X-ray detector 23.1 is moved to the next position (A2) of image pick-up (S906). The image pick-up by X-ray detector 23.2 is carried out in a similar manner as X-ray detector 23.1 described above. Here, to enable the image pick-up by X-ray detector 23.2, X-ray focal point 17 must be moved. This movement, however, is done at a relatively high speed as compared with other operations. The next position (A2) of image pick-up by X-ray detector 23.1 must be determined before the inspection. Generally, the positions of image pick-up by the X-ray detectors can be determined when the number of images to be picked-up is determined from design information such as the CAD data.

Next, computing unit 70 transfers the image data acquired by X-ray detector 23.2 to memory 90 used by computing unit 70 (S930).

In parallel with the data transfer, computing unit 70 emits X-ray at focal point position c1-1 and the image of object of inspection is picked-up by X-ray detector 23.3 (S928) and, at the same time, X-ray detector 23.2 is moved to the next position (B2) of image pick-up (S930). Image pick-up by X-ray detector 23.3 is carried out in a similar manner to that of X-ray detector 23.1 described above.

If the defined number of images to be picked-up for one field of view is not yet reached (S932), computing unit 70 transfers the image data acquired by X-ray detector 23.3 to memory 90 used by computing unit 70 (S936). In parallel with the data transfer, computing unit 70 emits X-ray at focal point positional-2 and the image of object of inspection is picked-up by X-ray detector 23.1 (S934) and, at the same time, X-ray detector 23.3 is moved to the next position (C2) of image pick-up (S936). Here again, the next position of image pick-up (C2) must be determined before the inspection.

Thereafter, in a similar manner, the image pick-up by X-ray detector 23.2 and the transfer of picked-up image data from X-ray detector 23.1 or the movement of X-ray detector 23.1 to the next position of the image pick-up are performed in parallel, or the image pick-up by X-ray detector 23.3 and the transfer of the picked-up image data from X-ray detector 23.2 or the movement of X-ray detector 23.2 to the next position of image pick-up are performed in parallel, or the image pick-up by X-ray detector 23.1 and the transfer of picked-up image data from X-ray detector 23.3 or the movement of X-ray detector 23.3 to the next position of the image pick-up are performed in parallel, repeatedly until the number of picked-up images reaches the defined number. In this regard, the operation is basically the same as the operation of Embodiment 1 described with reference to FIG. 14.

When image pick-up for the defined number ends (S932), computing unit 70 transfers the picked-up image data from X-ray detector 23.3 and moves X-ray detector 23.3 to the next position of the image pick-up (S938), and thus, the process of the image pick-up for one field of view ends (S940). Then, the process proceeds to S312.

The estimated time required for the CT image pick-up for one field of view using the linear detectors as in FIG. 52 is as follows.

The definitions of the times for respective processes are the same as above.

The time Tv of CT image pick-up for one field of view using S (for example, two) X-ray detectors 23 is a sum of N times the image pick-up time and N/S times the necessary time of mechanical movement. It is noted, however, that Tv changes depending on the time required by each process step. In the following, calculation will be done assuming 2Ts>Tm>>Tf (the speed of the movement of the X-ray focal point is sufficiently high to be negligible as compared with other processes), considering general time of image pick-up.

Description will be made assuming that there are three X-ray detectors.

First, for the image pick-up by X-ray detector 23.1, it takes time Ts. Next, for moving the X-ray focal point, it takes time Tf, while X-ray detector 23.1 is moved at the same time to the next position A2 of the image pick-up. Since X-ray detector 23.2 has already been positioned at the prescribed position, the image pick-up can be done without any time consumed for moving. Thus, the image pick-up takes Ts. After the image pick-up by X-ray detector 23.2, X-ray detector 23.2 is moved. Next, the image pick-up is done by X-ray detector 23.3. Since X-ray detector 23.3 has already been positioned at the prescribed position, the image pick-up can be done without any time consumed for moving. Thus, the image pick-up takes Ts.

Next, the image pick-up is done by X-ray detector 23.1. Since the movement has been finished, one cycle of the image pick-up takes 3Ts. Therefore, the time Tv for the image pick-up of one field of view is given by the following equation.

$$Tv=NTs.$$

Further, the time for the movement to the next field of view is only the time for moving the X-ray focal point, and therefore, $$Te=Tf.$$

Thus, image pick-up at a higher speed than a common image pick-up becomes possible.

Embodiment 6

When printed board with solder-mounted components are to be inspected with X-ray, it is the case that components that require inspection using reconstructed images such as a BGA and components for which inspection only with fluoroscopic image is sufficient exist together. Therefore, an X-ray inspecting apparatus capable of image pick-up in the following two methods is desired.

1) The apparatus is capable of picking-up images of a component from a plurality of directions, enabling image reconstruction for inspection.

2) The apparatus is capable of picking-up an image of the object placed directly above the X-ray source.

An arrangement of an X-ray detector suitable for the analytical method for the image reconstruction is on a circular orbit at a constant distance from a vertical axis of the object of inspection, and it is not good for inspection of the fluoroscopic image in the vertical direction. Therefore, an apparatus capable of fluoroscopic image pick-up and fluoroscopic image pick-up in the vertical direction must have a mechanism for moving the X-ray detector to the position for picking up fluoroscopic image by X-Y movement, or it must additionally have an X-ray detector dedicated for picking-up the fluoroscopic image.

If the mechanism for moving the X-ray detector to the position for picking up fluoroscopic image by X-Y movement is provided, such a mechanism must have a mechanical structure as simple as possible, from the viewpoint of attaining high moving accuracy and good maintainability. Providing an additional X-ray detector dedicated for picking up the fluoroscopic image leads to extra costs.

In view of the foregoing, the X-ray inspecting apparatus in accordance with Embodiment 6 has the following configuration.

i) Three X-ray detector moving mechanisms capable of moving the positions of X-ray detectors on a line independently from each other and three X-ray detectors (detectors) corresponding to the X-ray detector moving mechanisms are provided. Here, the number of X-ray detectors is at least two. It is desirable to provide three or more odd number of detectors, since, by providing odd number of X-ray detectors, it becomes possible to pick-up an image of the object of inspection from directly above, by the X-ray detector moving on the central rail. From the viewpoint of minimizing the number of detectors and the number of moving mechanisms considering costs, three is the desirable number.

ii) One of the three X-ray detector moving mechanisms is provided on a moving mechanism that can place the X-ray detector directly above the object of inspection and the X-ray source.

As described above, by providing odd number of X-ray detectors, it becomes possible to pick-up an image of the object of inspection from directly above, by the X-ray detector moving on the central rail. This is suitable for picking-up the fluoroscopic image for determination as to whether or not the inspection by the reconstructed image is necessary, in the operation in accordance with the flowchart described in the following.

iii) At the time of image pick-up, during exposure of the X-ray detector at the center, the X-ray detectors on opposite sides where exposure is not taking place, are moved to the next position of the image pick-up. During the exposure of the X-ray detectors at the opposite sides, the X-ray detector at the center not subjected to exposure is moved to the next position of the image pick-up.

iv) When two X-ray detectors are exposed at the same time, time-divisional irradiation of X-ray focal point (pulse irradiation) is done at a shorter time interval as compared with the time of exposure, at positions corresponding to the two X-ray detectors.

v) As a method for image reconstruction, the iterative method or image reconstruction by the tomosynthesis is used, whereby images picked up at positions not on the circular orbit (on a line) are used for reconstruction.

In the following, a configuration and operation of X-ray inspecting apparatus in accordance with Embodiment 6 will be described.

Figure 53:
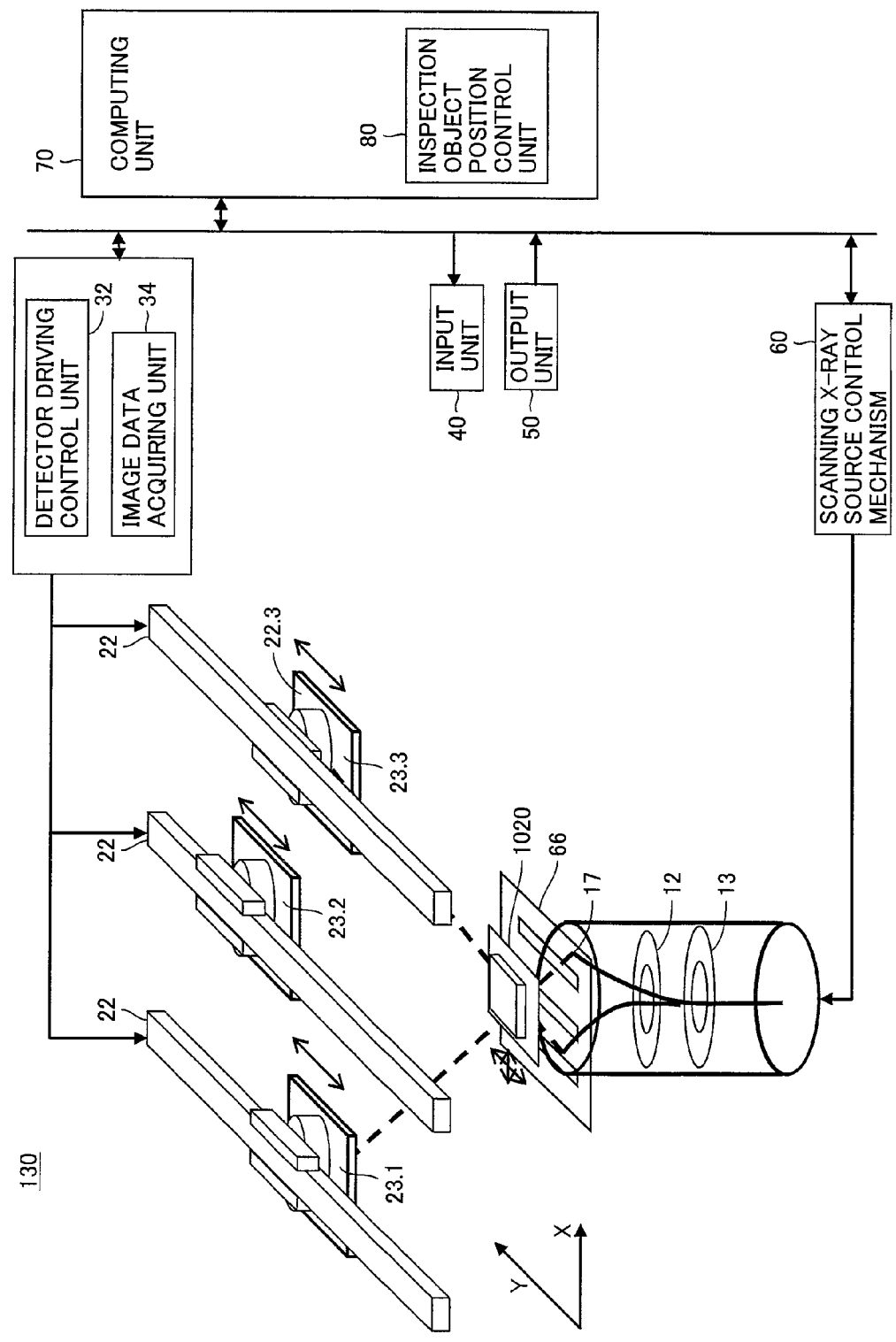
FIG. 53 illustrates a configuration of an X-ray inspecting apparatus 130 in accordance with Embodiment 6.

FIG. 53 illustrates a configuration of an X-ray inspecting apparatus 130 in accordance with Embodiment 6. X-ray inspecting apparatus 130 uses linear X-ray detectors and a scanning X-ray source as X-ray source 10. For one field of view, movement of the object of inspection is unnecessary during image pick-up.

Further, as will be described later, for pulse-wise operation of X-ray source 10, shield 66 similar to that shown in FIG. 21 is provided.

As in the example of FIG. 21, shield 66 is formed of such a material to have such a thickness that can sufficiently block X-ray, and preferably it is formed of lead. Since the X-ray detector moves linearly, each opening of the shield is formed to have a rectangular shape (or a slit). Further, the size of shield 66 is set such that X-ray from a focal point position corresponding to X-ray detector 23.1 does not enter X-ray detector 23.3. The size of the opening of shield 66 is set such that X-ray from the focal point position corresponding to X-ray detector 23.1 can sufficiently enter X-ray detector 23.1 but X-ray to X-ray detector 23.2 is blocked. The relations between the size of shield 66 and the size of openings described above are the same for other X-ray detectors 23.2 and 23.3.

Since shield 66 having slits appropriate for the area of inspection object, magnification and the size of X-ray detectors is provided, it becomes possible by X-ray detector 23 positioned on a line passing through the X-ray focal point and the object of inspection to acquire the X-ray fluoroscopic image from only a specific angle of the area of inspection object, even when a plurality of X-ray detectors are simultaneously subjected to exposure and X-rays are emitted from a plurality of positions.

The X-ray incident on shield 66 generates scattered rays, possibly inducing degradation of acquired images if all X-ray detectors 23 are subjected to exposure and pulse-wise irradiation for image pick-up at the same time. By way of example, if X-ray detectors 23.1, 23.2 and 23.3 are exposed simultaneously, scattered rays derived from the X-ray directed to X-ray detector 23.1 may have an influence on the image pick-up by X-ray detector 23.2. Therefore, operations of X-ray detectors 23 are adjusted such that exposure time for X-ray detectors 23.1 and 23.3 on opposite sides is made different from the exposure time of central X-ray detector 23.2, so that the influence of scattering rays is reduced in image pick-up, while the time for image pick-up is the same, as will be described later.

It is noted that the configuration of X-ray inspecting apparatus 130 is the same as that of X-ray inspecting apparatus 102 described with reference to FIG. 15, except for the control related to the movement of X-ray detector 23, the movement of X-ray focal point position 17 and the pulse-wise operation of X-ray source 10 as will be described in the following.

Therefore, description related to the configuration will not be repeated. As will be described in the following, a configuration for rotating X-ray detector 23 is unnecessary in the present modification of the embodiment, and X-ray detector 23 moves in a translational manner in the X-Y plane.

Figure 54:
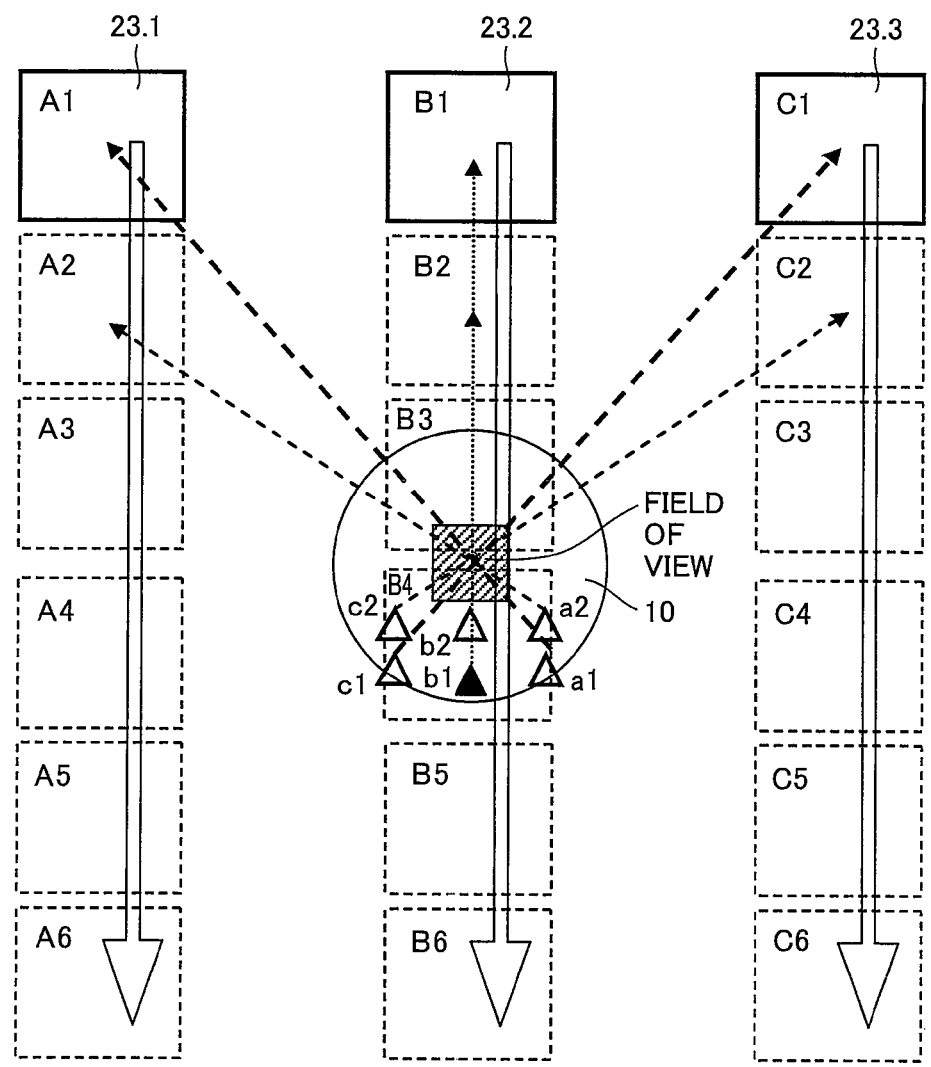
FIG. 54 is a top view showing movement trajectory of X-ray detector 23 and the scanning X-ray source, in the configuration of X-ray inspecting apparatus 130 shown in FIG. 53.

FIG. 54 is a top view showing movement trajectory of X-ray detector 23 and the scanning X-ray source, in the configuration of X-ray inspecting apparatus 130 shown in FIG. 53.

In the example of FIG. 54, X-ray detectors 23.1, 23.2 and 23.3 each have a mechanism allowing linear movement on a rail.

X-ray source 10 is a scanning X-ray source, as described above. Further, the position of the image pick-up of X-ray detector 23 is not limited to the arrangement of FIG. 54, and the number of images to be picked up is not limited to 18. The number of images enabling the inspection may be designated. The designated number of images to be picked up may be calculated from design information such as the CAD data, or may be determined by visual observation by the operator.

In FIG. 54, positions A1 to A6, B1 to B6 and C1 to C6 represent positions of X-ray detectors 23.1, 23.2 and 23.3 that acquire fluoroscopic images necessary for image reconstruction, respectively. The numbers 1 to 6 appended to the positions represent the order of image pick-up, and image is picked up first at position A1 and at A6 at the end.

Further, positions a1, a2, b1, b2, c1 and c2 represent focal point positions on the X-ray target, which correspond to the X-ray detector positions A1, A2, B1, B2, C1 and C2, respectively.

As described above, in the present embodiment, X-ray detectors 23.1 and 23.3 on opposite sides move in synchronization. X-ray detector 23.2 at the center moves independently.

In the operation example shown in FIG. 54, X-ray detector 23 does not rotate but moves in a translational manner in the X-Y plane. Such an operation example is suitable for the reconstruction method such as the iterative method or the tomosynthesis. The reason for this is that by the iterative method or the tomosynthesis, the reconstruction is possible regardless of the direction of the X-ray detector.

In such an operation, it is unnecessary to rotate the X-ray detector. Therefore, the X-ray detector driving mechanism can further be simplified, and the speed of operation and maintainability of the mechanism can be improved.

Figure 55:
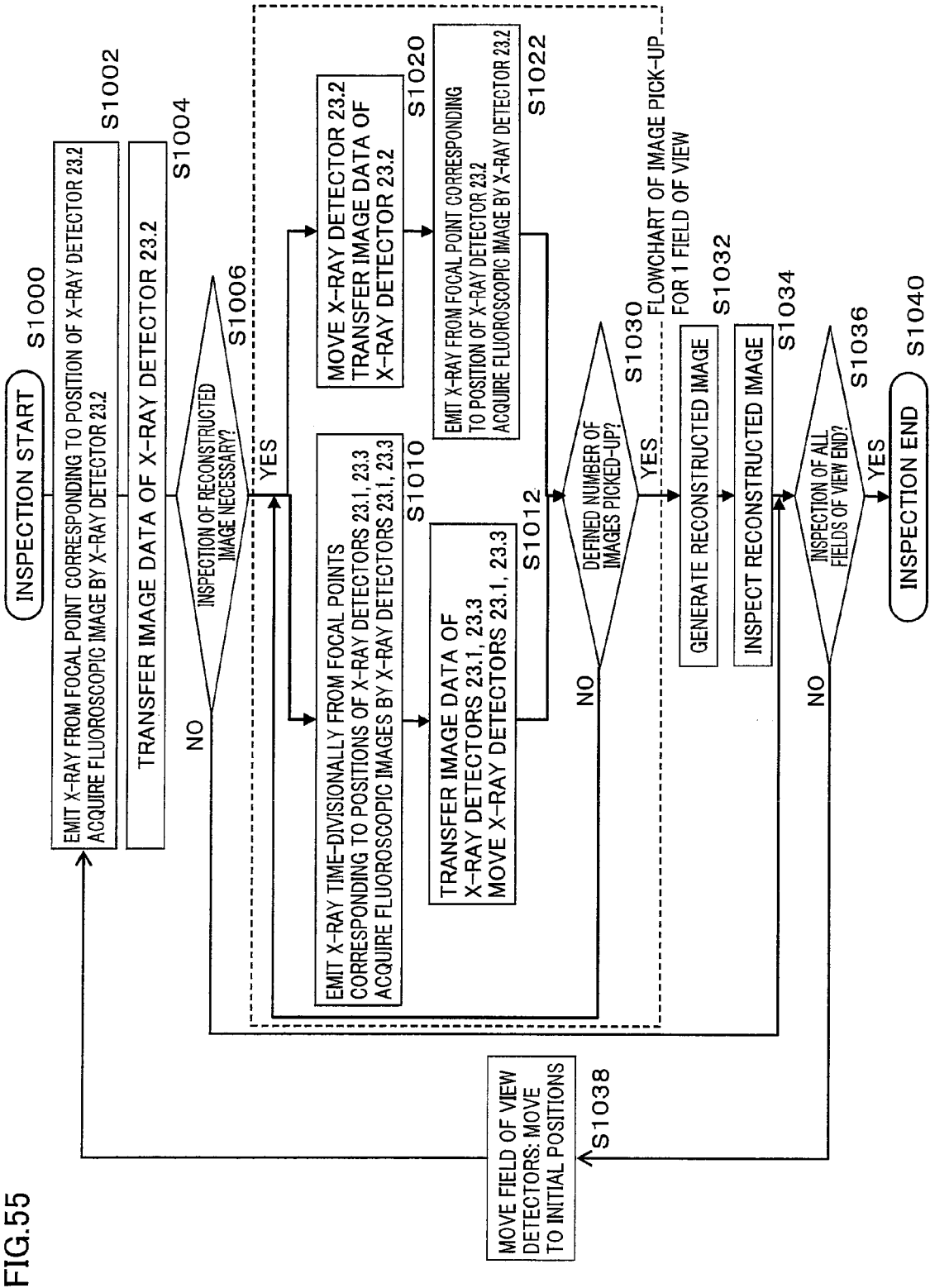
FIG. 55 is a flow chart of inspection of the imaging system using the linear detectors shown in FIGS. 53 and 54.

FIG. 55 is a flow chart of inspection of the imaging system using the linear detectors shown in FIGS. 53 and 54.

Figure 56:
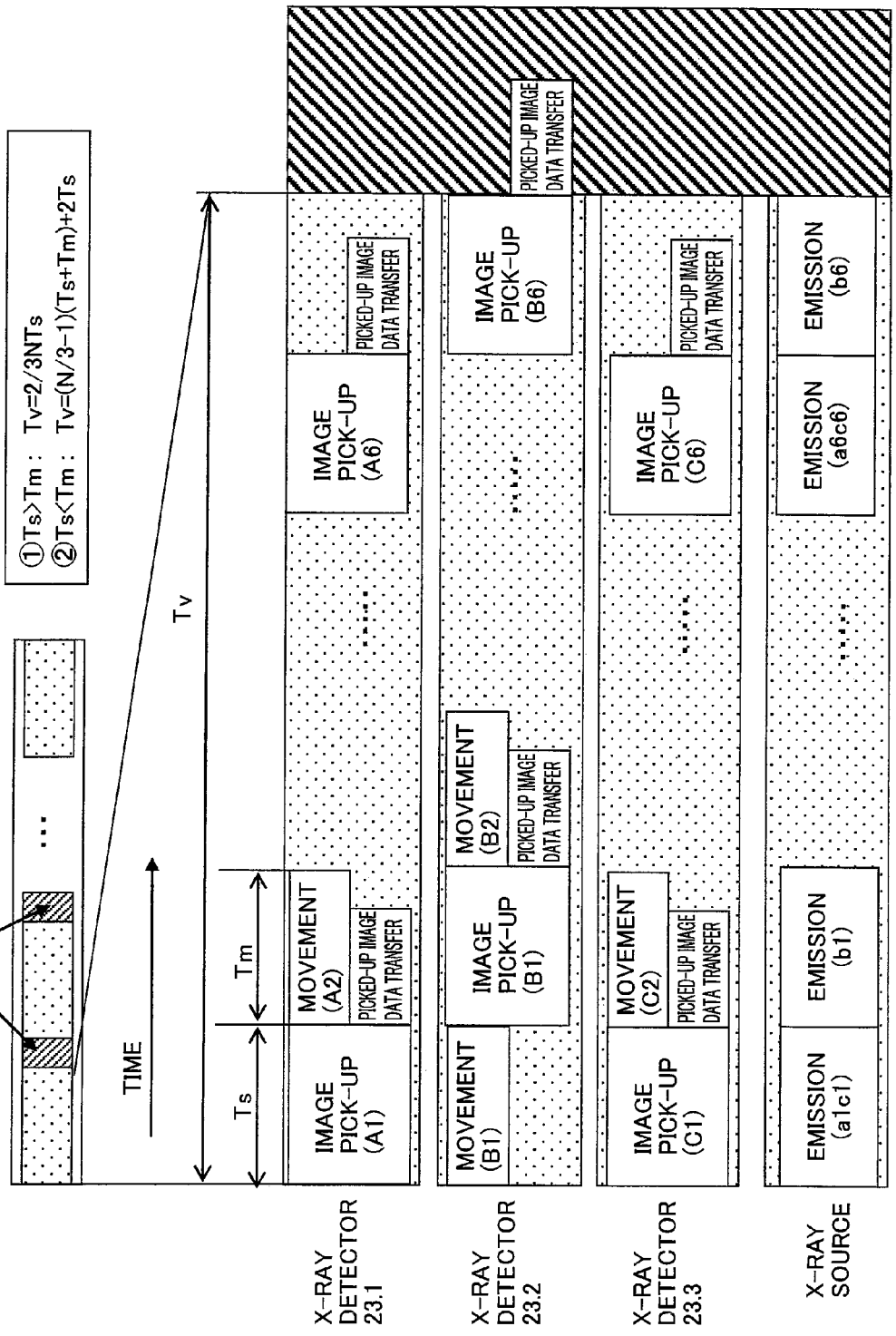
FIG. 56 is an inspection timing chart of imaging of one field of view by the imaging system shown in FIGS. 53 and 54.
Figure 57:
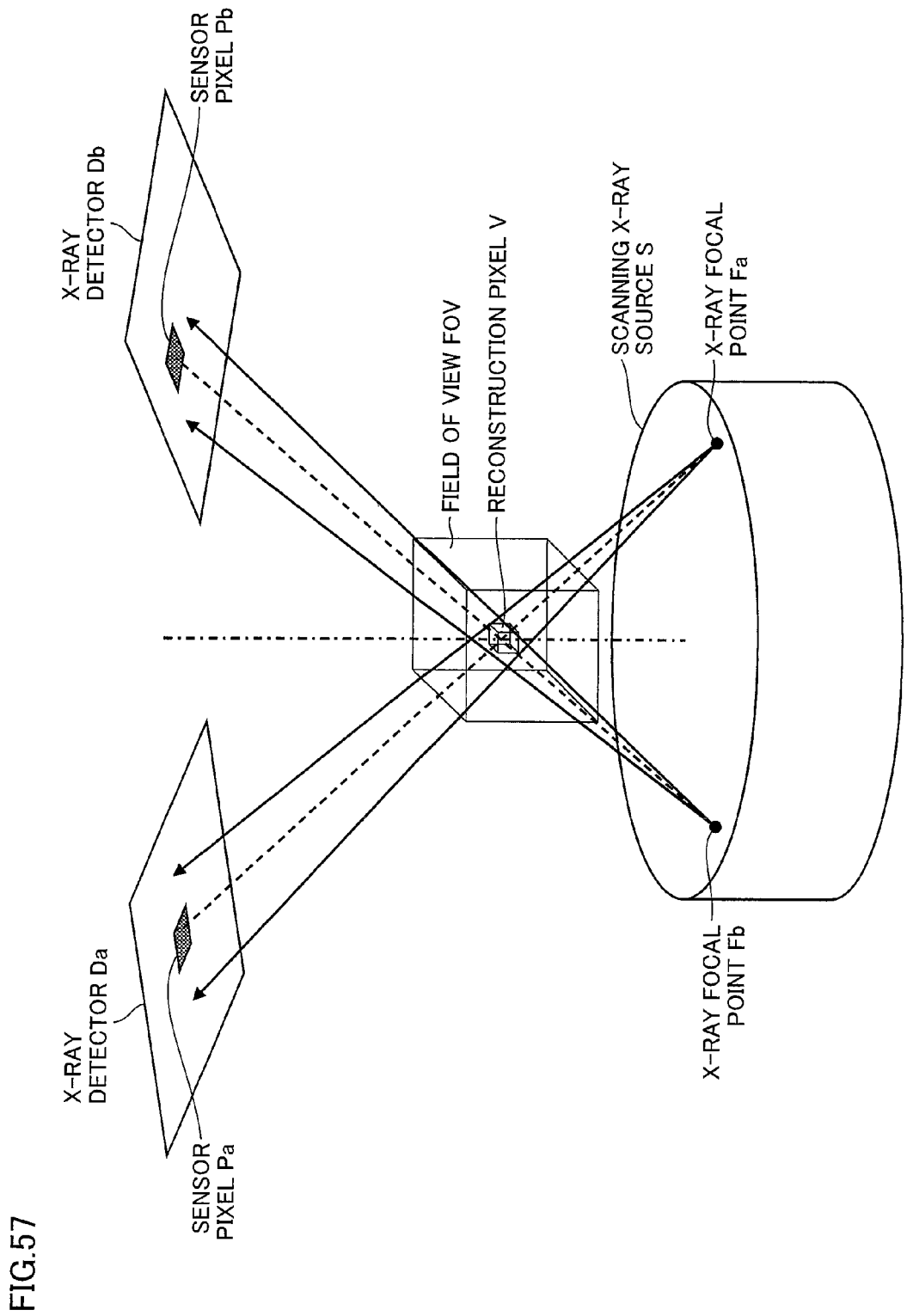
FIG. 57 illustrates a method for image reconstruction.
Figure 58:
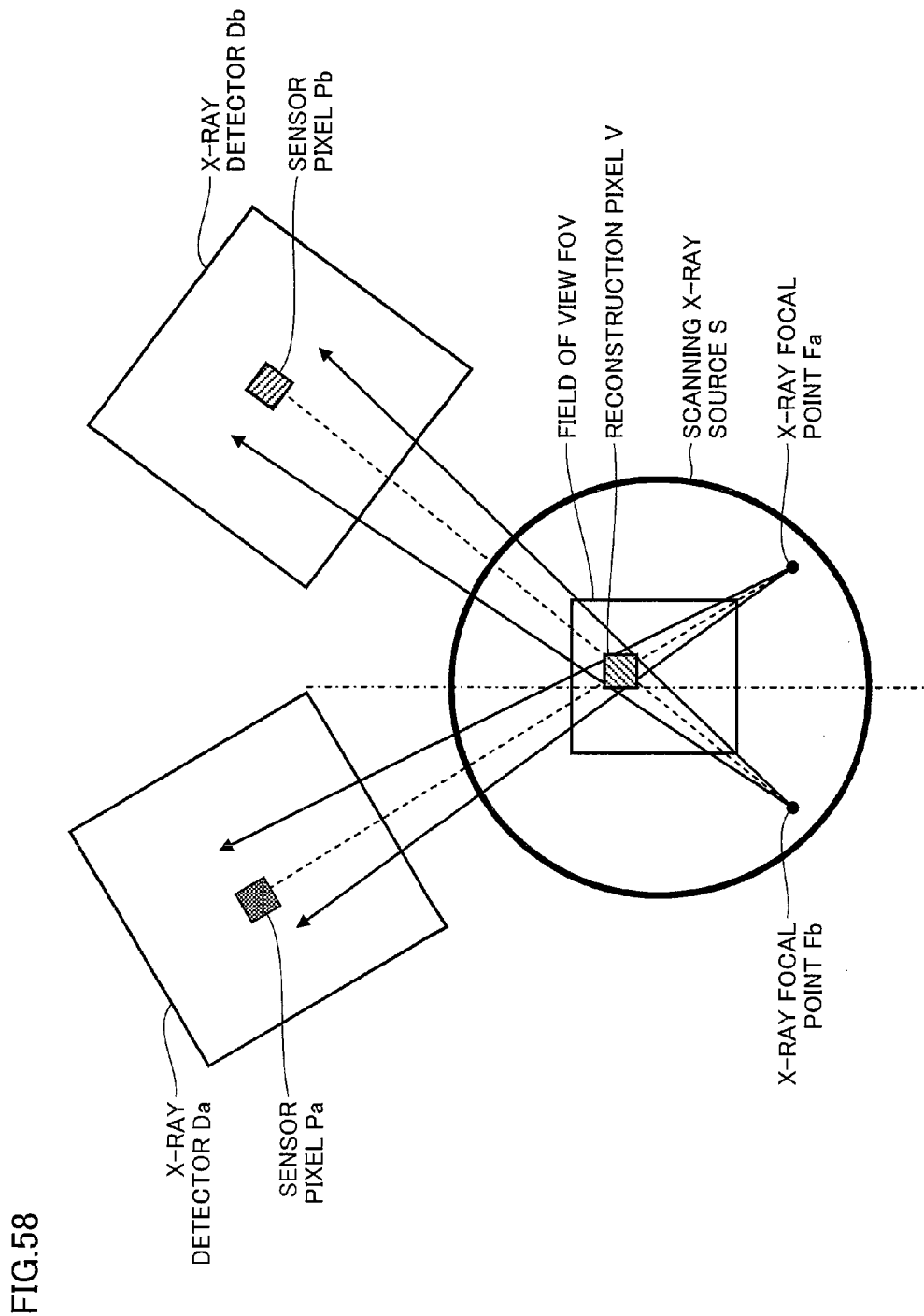
FIG. 58 shows arrangement of reconstruction pixel V as the object of operation of reconstruction in the field of view FOV, X-ray focal points Fa and Fb and X-ray detectors Da and Db, viewed from above.
Figure 59:
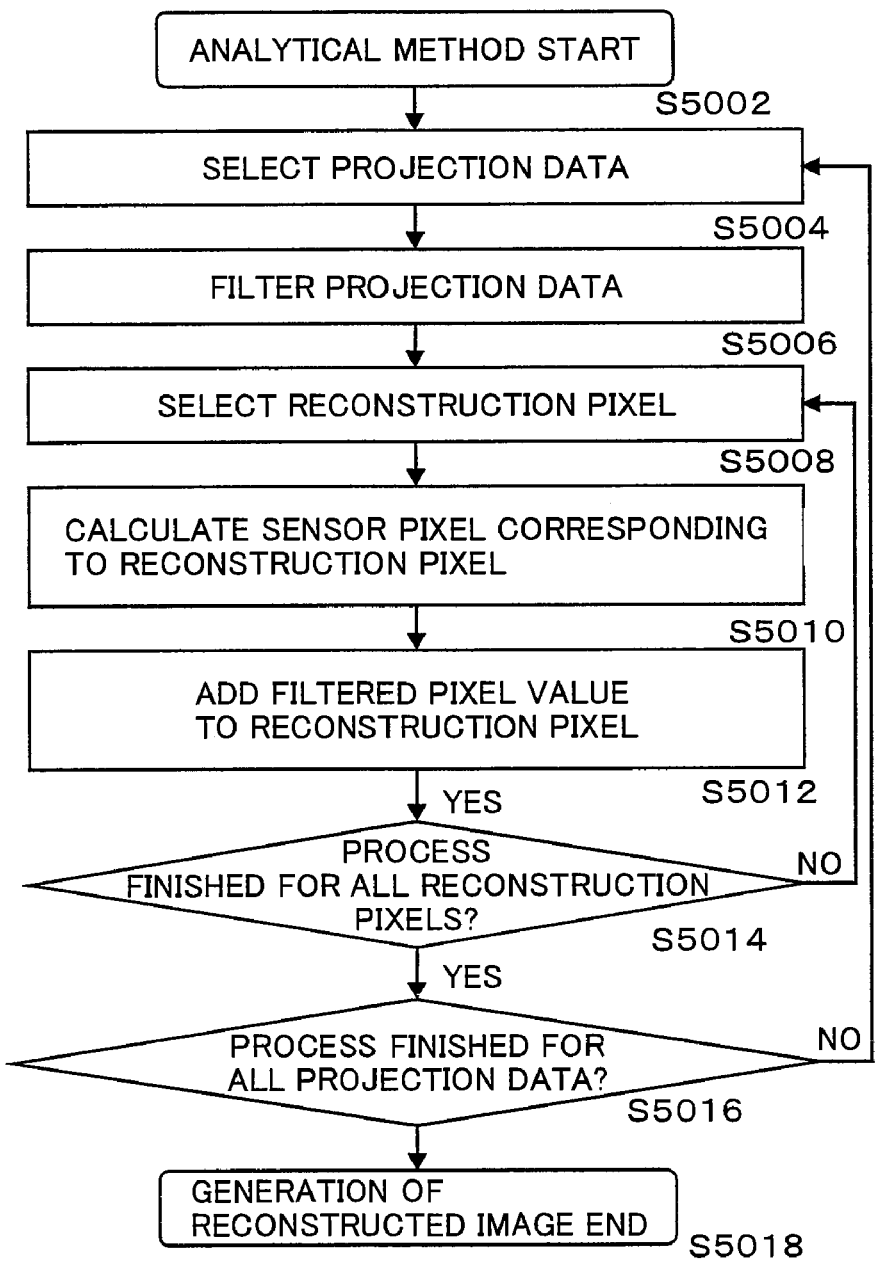
FIG. 59 is a flowchart representing the process steps of filtered back-projection method.
Figure 60:
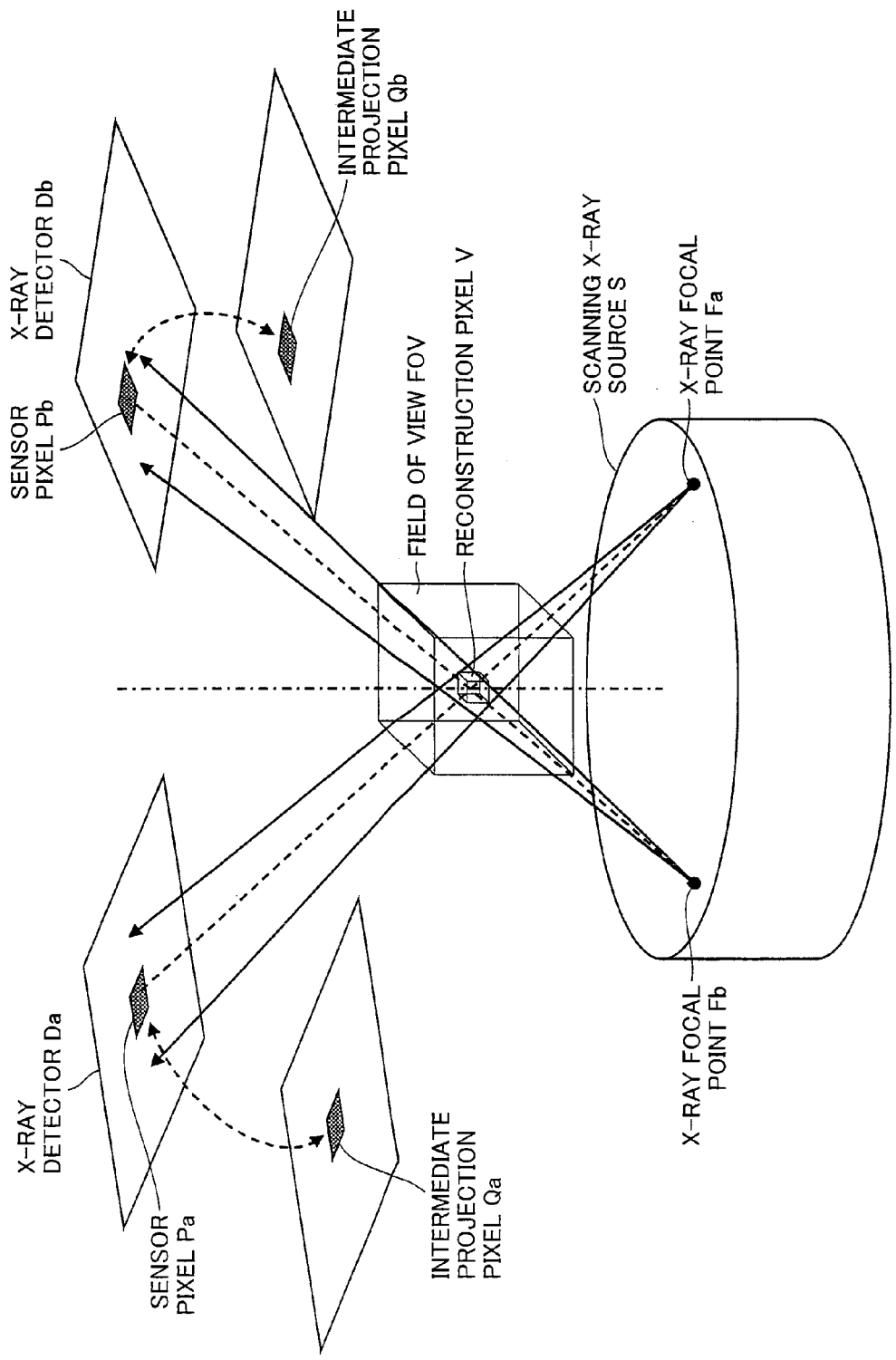
FIG. 60 is a schematic illustration showing the concept of processing by the iterative method, using a scanning X-ray source.
Figure 61:
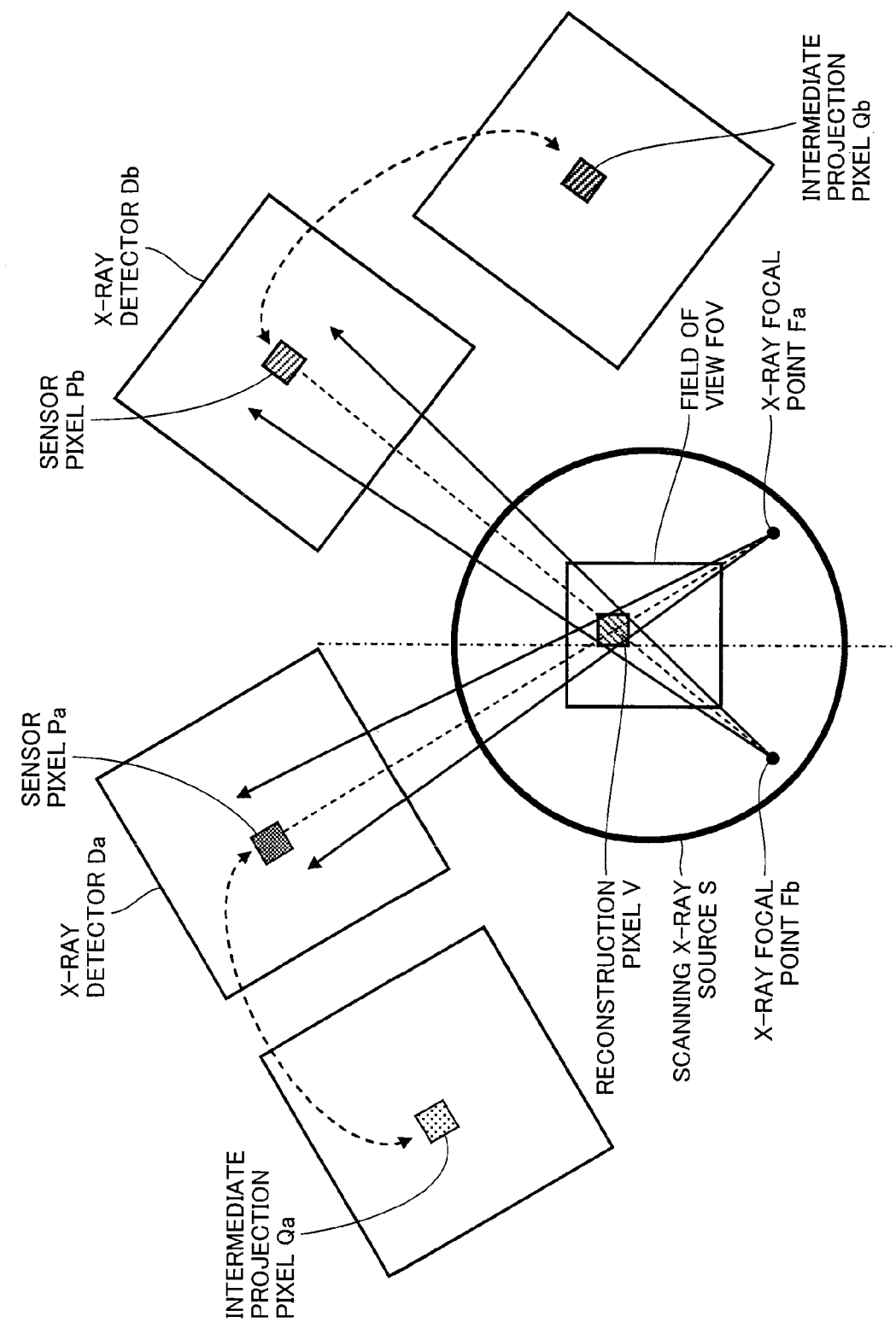
FIG. 61 is an illustration showing the concept of FIG. 60 viewed from above.
Figure 62:
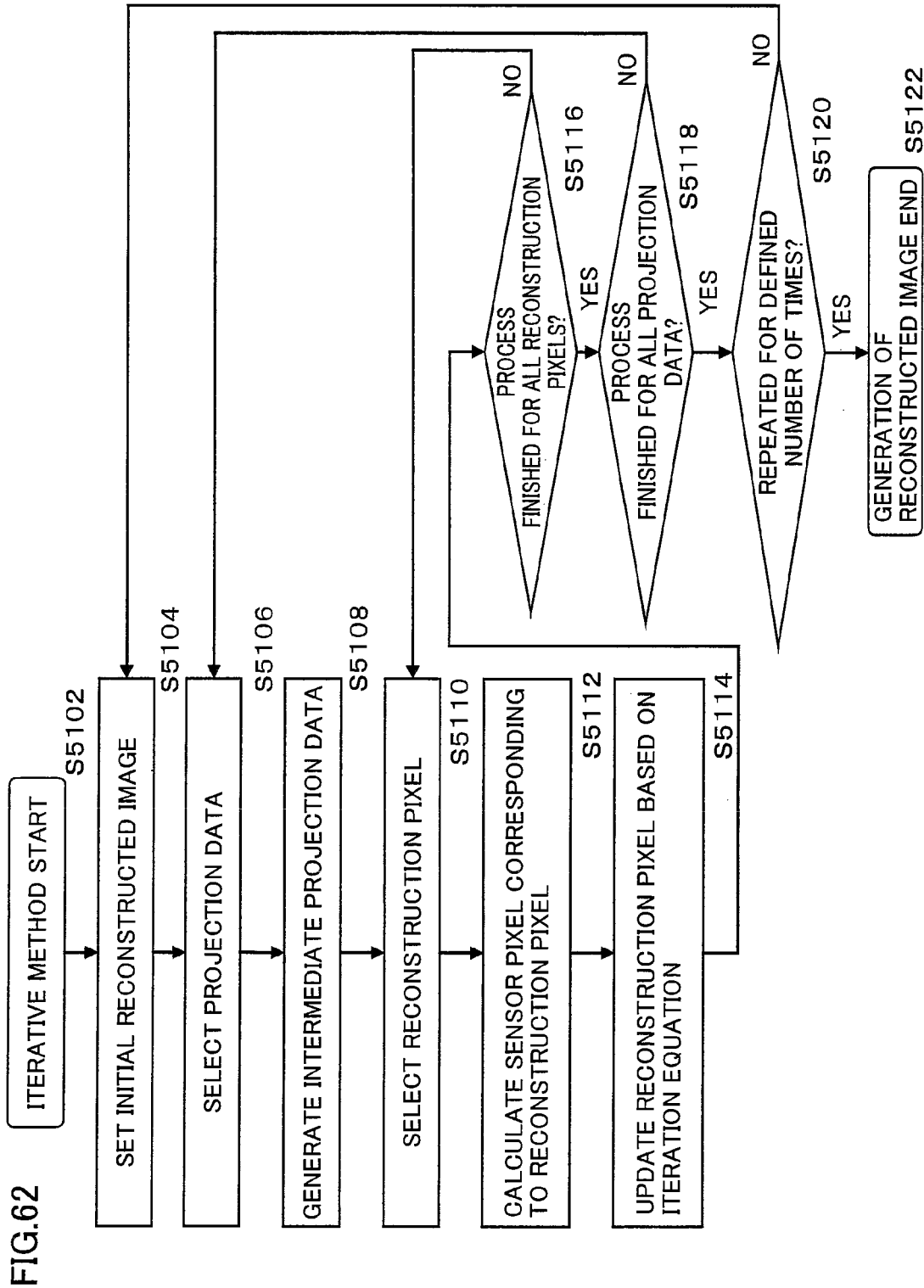
FIG. 62 is a flowchart representing the process steps of the iterative method.

FIG. 56 is an inspection timing chart of imaging of one field of view by the imaging system shown in FIGS. 53 and 54.

In the following, referring to FIGS. 55 and 56, the inspection process of X-ray inspecting apparatus 130 in accordance with a modification of Embodiment 6 will be described.

Referring to FIG. 55, before starting the inspection, it is assumed that the inspection object position control mechanism places the portion to be inspected (field of view) of the object of inspection on a vertical axis passing through the X-ray target of X-ray source 10, in accordance with an instruction from inspection object position control unit 80 of computing unit 70, and then, the inspection starts with the image pick-up by X-ray detector 23.2. Specifically, in order to acquire a fluoroscopic image, the stage on which the object of inspection is placed is moved to a prescribed position, and X-ray detector 23.2 is moved to the initial position (a middle position between B3 and B4), respectively. Further, X-ray detectors 23.1 and 23.3 are moved to initial positions A1 and C1, respectively. Generally, for inspection, an optical camera (not shown) is provided for specifying the position of detection and, therefore, it is possible to determine the position based on the position of the optical camera. Alternatively, the position may be automatically determined based on the CAD data of the object of inspection, or the position may be determined based on the visual observation by the operator.

When the inspection process starts (S1000), immediately after the start of inspection, computing unit 70 picks up an image with X-ray detector 23.2 positioned directly above the X-ray focal point (S1002). The acquired image data is transferred to memory 90 used by computing unit 70 (S1004), and from the X-ray fluoroscopic image acquired in this manner, acceptance/rejection determining unit 78 of computing unit 70 determines necessity of inspection based on the image reconstruction of the corresponding portion (S1006). Various method for determining the necessity (acceptance/rejection determination) have been proposed and described above. Therefore, details will not be repeated here. Therefore, details will not be repeated here.

If the inspection by the reconstructed image is unnecessary and if it is determined that inspection has been done on all fields of view (S1036), computing unit 70 ends the inspection (S1040).

If the inspection by the reconstructed image is necessary, then, computing unit 70 instructs the CT image pick-up for one field of view.

Referring to FIGS. 55 and 56, in the CT image pick-up for one field of view, images of a field of view in the inspection area (the reconstruction area or an area similar to the scope of the image pick-up for the fluoroscopic image described above) are picked-up from a plurality of directions.

Computing unit 70 moves the X-ray focal point to positions corresponding to X-ray detectors 23.1 and 23.3 on the opposite sides in a time-divisional manner and emits X-ray, whereby images are picked up by X-ray detectors 23.1 and 23.3 (S1010). In parallel with the image pick-up operation, computing unit 70 moves X-ray detector 23.2 to the next position (B1) of image pick-up (S1020). At this time point, only the movement of X-ray detector 23.2 takes place, and the acquired data is not transferred.

Thereafter, computing unit 70 transfers the data acquired by X-ray detectors 23.1 and 23.3 to memory 90, for example, for the reconstruction process at 3D image reconstructing unit 78 (S1012). In parallel therewith, computing unit 70 moves the X-ray focal point to a position corresponding to X-ray detector 23.2, emits X-ray, and an image is picked up by X-ray detector 23.2 (S1022).

If it is determined that the defined number of images for one field of view has not yet been picked up (S1030), computing unit 70 returns the process to steps S1010 and S1020.

If the number has reached the defined number, computing unit 70 ends the CT image pick-up for one field of view (S1030), and the process proceeds to S1032.

Though the determination as to whether the defined number has been reached is made after data transfer in the flowchart, it is preferred that the determination of the number of picked up images is made simultaneously with the data transfer. The reason for this is that the data transfer takes time of about 200 ms, for example, and therefore, the movement to the next position of the image pick-up is delayed. This leads to generation of delay at every image pick-up operation. In order to reduce the delay time and to speed-up the operations, it is preferable to make determination related to the defined number and to move the object of inspection and the X-ray detector simultaneously.

Next, 3D image reconstructing unit 76 of computing unit 70 generates a reconstructed image from the images picked-up from a plurality of directions at step S1032.

Thereafter, acceptance/rejection determining unit 78 of computing unit 70 determines acceptance/rejection based on the reconstructed image (S1034). Here again, the methods for determining acceptance/rejection are well known, and the method for determining acceptance/rejection suitable for the item to be inspected may be used. Therefore, detailed description will not be repeated here.

Further, computing unit 70 determines whether or not inspection of all fields of view is finished (S1036). If the inspection is not yet finished, the field of view is moved to the next position, X-ray detectors are returned to respective initial positions (S1038), and the process returns to step S1002. If the inspection of all fields of view is finished, computing unit 70 ends the present inspection (S1040).

Though the inspection is done using the fluoroscopic image and the reconstructed image in the example of FIG. 55, it is also possible to perform the inspection using only the reconstructed image, not using the fluoroscopic image. Generally, however, acceptance/rejection determination based on fluoroscopic image is done before the inspection by the reconstructed image, to make shorter the overall inspection time, since the reconstruction process takes relatively long time.

As shown in FIG. 56, during simultaneous exposure at X-ray detectors 23.1 and 23.3, X-ray detector 23.2 is moved to an image pick-up position allowing acquisition of an image necessary for image reconstruction. When image pick-up by X-ray detectors 23.1 and 23.3 and movement of X-ray detector 23.2 end, image pick-up by X-ray detector 23.2 starts, and X-ray detectors 23.1 and 23.3 are moved to the next position of image pick-up. By repeating these operations, a plurality of fluoroscopic images from different angles necessary for the image reconstruction can be picked-up without down time of X-ray source 10 and without moving the object of inspection.

The time Tv for image pick-up of one field of view can be represented by the following equations.

When $Ts > Tm: Tv = 2/3 NTs$

When $Ts < Tm: Tv = (N/3 - 1)(Ts + Tm) + 2Ts$.

By way of example, the time necessary for picking up 18 images is 12Ts if Ts>Tm, and 7Ts+5Tm if Ts<Tm. Thus, the time for image pick-up can significantly be reduced.

Because of the configuration as described above, at least one of or combination of the following effects can be attained by X-ray inspecting apparatus 130 in accordance with Embodiment 6.

1) X-ray detectors 23 operate independently from each other, so that down time of X-ray source 10 among the X-ray detectors 23 can be reduced.

2) The target current is increased and a plurality of X-ray detectors 23 are subjected to exposure simultaneously, whereby the highly intense X-ray can efficiently be utilized.

3) The operation of X-ray detector is limited to linear operation, so that the mechanism for moving X-ray detector 23 can be simplified and the speed of the movement can be increased.

4) Rectangular images picked up by X-ray detectors 23 moving in the same direction (moving in a translational manner) are reconstructed by the iterative image reconstructing algorithm, whereby a reconstructed image of wide scope can be obtained.

5) By a configuration having odd number of X-ray detectors, for example, three X-ray detectors with one passing directly above X-ray source 10, the apparatus can be used for picking-up both fluoroscopic images and images for reconstruction.

6) Further, if three X-ray detectors 23 are provided, by shifting the timing of exposure by the central X-ray detector and by two X-ray detectors on opposite sides, degradation of images caused by scattered X-rays to the X-ray detectors on opposite sides when an image is picked-up by the central detector and scattered X-rays to the central X-ray detector when images are picked up by the detectors on opposite sides can be avoided. Similar effects can be attained if five or more odd number of X-ray detectors are provided, by shifting the timing of exposure between the central and every other X-ray detectors and the remaining X-ray detectors.

The embodiments as have been described here are mere examples and should not be interpreted as restrictive. The scope of the present invention is determined by each of the claims with appropriate consideration of the written description of the embodiments and embraces modifications within the meaning of and equivalent to, the languages in the claims.

The invention claimed is:

1. An X-ray inspecting apparatus, forming images of X-ray transmitted through an area of inspection of an object on a plurality of detection surfaces, for executing a process of reconstructing an image of the area of inspection, comprising:
    a plurality of X-ray detectors smaller in number than the detection surfaces, configured to pick-up images on said plurality of detection surfaces;
    a detector driving unit configured to drive some of said plurality of X-ray detectors and remaining ones of said plurality of X-ray detectors independently from each other;
    an X-ray output unit configured to output X-ray such that the X-ray transmitted through said area of inspection enters said plurality of X-ray detectors moved to a plurality of image pick-up positions as said detection surfaces; and
    a control unit configured to control an operation of said X-ray inspecting apparatus; wherein
    said control unit includes:
        an image acquisition control unit configured to control timing of exposure by each of said X-ray detectors and said detector driving unit,
        an X-ray output control unit configured to control said X-ray output unit, and
        an image reconstruction processing unit configured to reconstruct image data of said area of inspection, based on data of intensity distribution of X-ray transmitted through said area of inspection, picked-up at said plurality of detection surfaces; and
    said image acquisition control unit and said X-ray output control unit configured to execute, in parallel,
        a process of image pick-up by said some of said plurality of X-ray detectors at a first position among said plurality of image pick-up positions, and a process of moving said remaining ones of said plurality of X-ray detectors to a second position different from said first position among said plurality of image pick-up positions.

2. The X-ray inspecting apparatus according to claim 1, wherein
    said image acquisition control unit and said X-ray output control unit cause,
    for performing image pick-up of one area of inspection of said object, at a preset number of said image pick-up positions for said image data reconstruction separately in a number of times,
    said some of said plurality of X-ray detectors to execute
        a process of image pick-up at said first position and a process of moving to a next first position different from said first position after the image pick-up, and
    cause said remaining ones of said plurality of X-ray detectors to execute
    in parallel with said process of image pick-up at said first position by said some, a process of moving to said second position corresponding to next image pick-up different from said first position, from the next first position and from previous said second position, and in parallel with said process of moving said some to the next first position, a process of image pick-up at said second position.

3. The X-ray detector according to claim 1, wherein
    said X-ray output control unit includes an originating point setting unit configured to set, for said plurality of detection surfaces, each originating position of emission of said X-ray such that said X-ray passes through said area of inspection and is incident on each of said detection surfaces; and
    said X-ray output unit is configured to move an X-ray focal point position of X-ray source to each said originating position and generate said X-ray.

4. The X-ray inspecting apparatus according to claim 3, wherein
    said X-ray output unit is configured to move said X-ray focal point position by deflecting an electron beam to be incident on a target surface of a continuous surface of the X-ray source.

5. The X-ray inspecting apparatus according to claim 1, wherein said detector driving unit includes a uniaxial driving unit configured to move some of said plurality of X-ray detectors in a direction along a prescribed axis.

6. The X-ray inspecting apparatus according to claim 5, wherein
    said uniaxial driving unit is configured to move said plurality of X-ray detectors in a translational manner in a prescribed plane.

7. The X-ray inspecting apparatus according to claim 5, wherein
    said detection surfaces of said plurality of X-ray detectors each has a rectangular shape; and
    said detector driving unit includes a rotating unit configured to rotate said plurality of X-ray detectors such that one end of said detection surface of said plurality of X-ray detectors intersects a direction toward said X-ray output unit at each said image pick-up position.

8. The X-ray inspecting apparatus according to claim 5, wherein
    the image reconstruction processing unit is configured to reconstruct image data of said area of inspection by an iterative method or an analytical method.

9. An X-ray inspecting apparatus according to claim 1, wherein said X-ray output unit is configured to generate, to a plurality of X-ray detectors simultaneously in a state of image pick-up among the plurality of X-ray detectors arranged at said image pick-up positions, X-rays from a plurality of corresponding X-ray focal point positions,
    said X-ray inspecting apparatus further comprising
    a shielding member configured to allow passage of X-rays from said X-ray output unit, from a corresponding X-ray focal point position through said area of inspection to each of said detection surfaces of each of said X-ray detectors simultaneously in a state of image pick-up, and block an X-ray from a not-corresponding X-ray focal point position.

10. The X-ray inspecting apparatus according to claim 9, wherein said X-ray output unit is configured to move said X-ray focal point position by deflecting an electron beam to be incident on a target surface of a continuous surface of the X-ray source; and said X-ray output control unit is configured to control said X-ray output unit such that said X-ray enters each of said plurality of X-ray detectors simultaneously in a state of image pick-up in a time-divisional manner.

11. An X-ray inspecting apparatus, forming images of X-ray transmitted through an area of inspection of an object on a plurality of detection surfaces, for executing a process of reconstructing an image of the area of inspection, comprising:

a plurality of X-ray detectors smaller in number than the detection surfaces, configured to pick-up images on said plurality of detection surfaces;

a translational driving unit configured to move said plurality of X-ray detectors in a translational manner in a prescribed plane;

an X-ray output unit configured to output X-ray such that the X-ray transmitted through said area of inspection enters said plurality of X-ray detectors moved to a plurality of image pick-up positions as said detection surfaces, said X-ray output unit is further configured to generate, to a plurality of X-ray detectors simultaneously in a state of image pick-up among the plurality of X-ray detectors arranged at said image pick-up positions, X-rays from a plurality of corresponding X-ray focal point positions;

a shielding member configured to allow passage of X-rays from said X-ray output unit, from a corresponding X-ray focal point position through said area of inspection to each of said detection surfaces of each of said X-ray detectors simultaneously in a state of image pick-up, and block an X-ray from a not-corresponding X-ray focal point position; and a control unit configured to control an operation of said X-ray inspecting apparatus; wherein said control unit includes:

an image acquisition control unit configured to control timing of exposure by each of said X-ray detectors and said translational driving unit, an X-ray output control unit configured to control said X-ray output unit, and an image reconstruction processing unit configured to reconstruct image data of said area of inspection, based on data of intensity distribution of the X-ray transmitted through said area of inspection, picked-up at said plurality of detection surfaces.

12. The X-ray inspecting apparatus according to claim 1, wherein said detector driving unit includes a two-axis driving unit configured to move said plurality of X-ray detectors independently along directions of prescribed two axes.

13. A method to be performed by an X-ray inspecting apparatus for X-ray inspection, picking-up images of X-rays transmitted through an area of inspection of an object by X-ray detectors corresponding to a plurality of detection surfaces, for executing a process of reconstructing an image of said area of inspection, wherein said X-ray inspecting apparatus includes an X-ray output unit and a control unit, said control unit is configured to control an operation of said X-ray inspecting apparatus, the method comprising the steps of:

moving each of said X-ray detectors independently to an image pick-up position to be said detection surface;

outputting, by said X-ray output unit, an X-ray such that the X-ray transmitted through said area of inspection enters said plurality of X-ray detectors moved to a plurality of said image pick-up positions respectively;

controlling, by said control unit, timing of exposure;

executing, in parallel, by said control unit, a process of image pick-up by said some of said plurality of X-ray detectors at a first position among said plurality of image pick-up positions, and a process of moving remaining ones, different from said some, of said plurality of X-ray detectors, to a second position different from said first position among said plurality of image pick-up positions; and reconstructing, by said control unit, image data of said area of inspection, based on data of intensity distribution of X-ray transmitted through said area of inspection, picked-up at said plurality of detection surfaces.

14. The method for X-ray inspection according to claim 13, wherein said step of executing includes, for performing image pick-up of one area of inspection of said object, at a preset number of said image pick-up positions for said image data reconstruction separately in a number of times, the step of causing said some of said plurality of X-ray detectors to execute a process of image pick-up at said first position and a process of moving to a next first position different from said first position after the image pick-up, and in parallel with said process of image pick-up at said first position by said some, causing said remaining ones of said plurality of X-ray detectors to execute a process of moving to said second position corresponding to next image pick-up different from said first position, from the next first position and from previous said second position, and in parallel with said process of moving said some to the next first position, a process of image pick-up at said second position.

15. The method for X-ray inspection according to claim 13, wherein said step of outputting X-ray includes the step of moving said X-ray focal point position by deflecting an electron beam to be incident on a target surface of a continuous surface of the X-ray source.

* * * * *